US007670771B2

(12) United States Patent
Leppert et al.

(10) Patent No.: US 7,670,771 B2
(45) Date of Patent: Mar. 2, 2010

(54) MUTANT SODIUM CHANNEL $Na_v1.7$ NUCLEIC ACID METHODS

(75) Inventors: Mark F. Leppert, Salt Lake City, UT (US); Nanda A. Singh, Heber City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 400 days.

(21) Appl. No.: 10/585,717

(22) PCT Filed: Jan. 21, 2005

(86) PCT No.: PCT/US2005/002059

§ 371 (c)(1),
(2), (4) Date: Mar. 14, 2007

(87) PCT Pub. No.: WO2005/069969

PCT Pub. Date: Aug. 4, 2005

(65) Prior Publication Data

US 2007/0275384 A1 Nov. 29, 2007

Related U.S. Application Data

(60) Provisional application No. 60/538,149, filed on Jan. 21, 2004.

(51) Int. Cl.
*C12Q 1/68* (2006.01)
(52) U.S. Cl. ......................................................... 435/6
(58) Field of Classification Search ........................ None
See application file for complete search history.

(56) References Cited

U.S. PATENT DOCUMENTS

| 6,060,271 | A | 5/2000 | Walewski et al. |
| 6,110,672 | A | 8/2000 | Mandel et al. |
| 6,673,549 | B1 | 1/2004 | Furness et al. |
| 2003/0194751 | A1 | 10/2003 | Dubin et al. |

FOREIGN PATENT DOCUMENTS

| AU | 2005207002 | 1/2005 |
| CA | 2553745 | 1/2005 |
| EP | 05711840 | 1/2005 |
| JP | 2006-551331 | 1/2005 |
| WO | WO 96/14077 | 5/1996 |
| WO | WO 02/083945 | 10/2002 |
| WO | PCT/US05/02059 | 1/2005 |

OTHER PUBLICATIONS

Agnew WS, Levinson SR, Brabson JS, Raftery MA. Purification of the tetrodotoxin-binding component associated with the voltage-sensitive sodium channel from Electrophorus electricus electroplax membranes. Proc Natl Acad Sci U S A. Jun. 1978;75(6):2606-10.
Agnew WS, Moore AC, Levinson SR, Raftery MA. Identification of a large molecular weight peptide associated with a tetrodotoxin binding protein from the electroplax of Electrophorus electricus. Biochem Biophys Res Commun. Feb. 12, 1980;92(3):860-6.
Alberts, et al., eds., "Molecular Biology of the Cell: Chapter 11: Membrane Transport" 534-535, Garland Pub., New York, N.Y. (1994).
Andersen OS, Koeppe RE 2nd. Molecular determinants of channel function. Physiol Rev. Oct. 1992;72(4 Suppl):S89-158.
Annegers JF, Hauser WA, Shirts SB, Kurland LT. Factors prognostic of unprovoked seizures after febrile convulsions.N Engl J Med. Feb. 26, 1987;316(9):493-8.
Catterall WA. Molecular properties of voltage-sensitive sodium channels. Annu Rev Biochem. 1986;55:953-85.
Catterall WA. Cellular and molecular biology of voltage-gated sodium channels. Physiol Rev. Oct. 1992;72(4 Suppl):S15-48.
Catterall WA. Structure and function of voltage-gated ion channels. u Rev Biochem. 1995;64:493-531.
Catterall WA. From ionic currents to molecular mechanisms: the structure and function of voltage-gated sodium channels. Neuron. Apr. 2000;26(1):13-25.
Escayg A, MacDonald BT, Meisler MH, Baulac S, Huberfeld G, An-Gourfinkel I, Brice A, LeGuern E, Moulard B, Chaigne D, Buresi C, Malafosse A. Mutations of SCN1A, encoding a neuronal sodium channel, in two families with GEFS+2. Nat Genet. Apr. 2000;24(4):343-5.
Felts PA, Yokoyama S, Dib-Hajj S, Black JA, Waxman SG. Sodium channel alpha-subunit mRNAs I, II, III, NaG, Na6 and hNE (PN1): different expression patterns in developing rat nervous system. Brain Res Mol Brain Res. Apr. 1997;45(1):71-82.
Fujiwara T, Sugawara T, Mazaki-Miyazaki E, Takahashi Y, Fukushima K, Watanabe M, Hara K, Morikawa T, Yagi K, Yamakawa K, Inoue Y. Mutations of sodium channel alpha subunit type 1 (SCN1A) in intractable childhood epilepsies with frequent generalized tonic-clonic seizures. Brain. Mar. 2003;126(Pt 3):531-46.
Goldin AL, Barchi RL, Caldwell JH, Hofmann F, Howe JR, Hunter JC, Kallen RG, Mandel G, Meisler MH, Netter YB, Noda M, Tamkun MM, Waxman SG, Wood JN, Catterall WA, Nomenclature of voltage-gated sodium channels. Neuron. Nov. 2000;28(2):365-8.
Goldin AL. Resurgence of sodium channel research. Annu Rev Physiol. 2001;63:871-94.
Hartshorne RP, Catterall WA. The sodium channel from rat brain. Purification and subunit composition. Biol Chem. Feb. 10, 1984;259(3):1667-75.

(Continued)

*Primary Examiner*—Michael Pak
(74) *Attorney, Agent, or Firm*—Ballard Spahr Andrews & Ingersoll, LLP

(57) ABSTRACT

Described are mutant $Na_v1.7$ sodium channel alpha-subunits and nucleic acid sequences encoding such mutants. Further described are methods for characterizing a nucleic acid sequence that encodes a $Na_v1$ sodium channel alpha-subunit, methods for determining a $Na_v1.7$ haplotype, methods for determining a subject's predisposition to a neurologic disorder associated with a sodium channel mutation, and methods of identifying a compound that modulates mutant $Na_v1.7$ sodium channels. Other materials, compositions, articles, devices, and methods relating to mutant $Na_v1.7$ sodium channels are also described herein.

14 Claims, 4 Drawing Sheets

OTHER PUBLICATIONS

Kraner SD, Tanaka JC, Barchi RL. Purification and functional reconstitution of the voltage-sensitive sodium channel from rabbit T-tubular membranes.J Biol Chem. May 25, 1985;260(10):6341-7.

Lossin C, Rhodes TH, Desai RR, Vanoye CG, Wang D, Carniciu S, Devinsky O, George AL Jr. Epilepsy-associated dysfunction in the voltage-gated neuronal sodium channel SCN1A. J Neurosci. Dec. 10, 2003;23(36):11289-95.

Nabbout R, Gennaro E, Dalla Bernardina B, Dulac O, Madia F, Bertini E, Capovilla G, Chiron C, Cristofori G, Elia M, Fontana E, Gaggero R, Granata T, Guerrini R, Loi M, La Selva L, Lispi ML, Matricardi A, Romeo A, Tzolas V, Valseriati D, Veggiotti P, Vigevano F, Vallee L, Dagna Bricarelli F, Bianchi A, Zara F. Spectrum of SCN1A mutations in severe myoclonic epilepsy of infancy. Neurology. Jun. 24, 2003;60(12):1961-7.

National Institutes of Health Grant No. R01NS032666.

Peiffer A, Thompson J, Charlier C, Otterud B, Varvil T, Pappas C, Barnitz C, Gruenthal K, Kuhn R, Leppert M. A locus for febrile seizures (FEB3) maps to chromosome 2q23-24. Ann Neurol. Oct. 1999;46(4):671-8.

Sangameswaran L, Fish LM, Koch BD, Rabert DK, Delgado SG, Ilnicka M, Jakeman LB, Novakovic S, Wong K, Sze P, Tzoumaka E, Stewart GR, Herman RC, Chan H, Eglen RM, Hunter JC. A novel tetrodotoxin-sensitive, voltage-gated sodium channel expressed in rat and human dorsal root ganglia. J Biol Chem. Jun. 6, 1997;272(23):14805-9.

Singh R, Scheffer IE, Crossland K, Berkovic SF. Generalized epilepsy with febrile seizures plus: a common childhood-onset genetic epilepsy syndrome. Ann Neural. Jan. 1999;45(1):75-81.

Sugawara T, Tsurubuchi Y, Agarwala KL, Ito M, Fukuma G, Mazaki-Miyazaki E, Nagafuji H, Noda M, Imoto K, Wada K, Mitsudome A, Kaneko S, Montal M, Nagata K, Hirose S, Yamakawa K. A missense mutation of the Na+ channel alpha II subunit gene Na(v)1.2 in a patient with febrile and afebrile seizures causes channel dysfunction. Proc Natl Acad Sci U S A. May 22, 2001;98(11):6384-9.

Tanaka JC, Eccleston JF, Barchi RL. Cation selectivity characteristics of the reconstituted voltage-dependent sodium channel purified from rat skeletal muscle sarcolemma. J Biol Chem. Jun. 25, 1983;258(12):7519-26.

Toledo-Aral JJ, Moss BL, He ZJ, Koszowski AG, Whisenand T, Levinson SR, Wolf JJ, Silos-Santiago I, Halegoua S, Mandel G. Identification of PN1, a predominant voltage-dependent sodium channel expressed principally in peripheral neurons.Proc Natl Acad Sci U S A. Feb. 18, 1997;94(4):1527-32.

Vijayaragavan K, Boutjdir M, Chahine M. Modulation of Nav1.7 and Nav1.8 peripheral nerve sodium channels by protein kinase A and protein kinase C. J Neurophysiol. Apr. 2004;91(4):1556-69.

Wallace RH, Scheffer IE, Barnett S, Richards M, Dibbens L, Desai RR, Lerman-Sagie T, Lev D, Mazarib A, Brand N, Ben-Zeev B, Goikhman I, Singh R, Kremmidiotis G, Gardner A, Sutherland GR, George AL Jr, Mulley JC, Berkovic SF. Neuronal sodium-channel alpha1-subunit mutations in generalized epilepsy with febrile seizures plus. Am J Hum Genet. Apr. 2001;68(4):859-65. Epub Mar. 13, 2001.

Database NCBI "Variation associated with SCN9A" Aug. 7, 2003 Database accession No. rs7589743.

Database NCBI "Variation associated with SCN9A" Aug. 7, 2003 Database accession No. rs6432901.

Hong et al., "Painful diabetic neuropathy: evidence for altered expression and function of sodium channels," *S. Neurosci. Abstract Viewer and Itinerary* Planer, Nov. 2003 p. 657.5.

Sorensen et al., "$Na_v1.7$/Pn1 sodium channel upregulation and accumulation at demyelinated sites in painful human tooth pulp," *S. Neurosci. Abstract Viewer and Itinerary Planer*, Nov. 2003 p. 175.13.

MUTANT SODIUM CHANNEL NA$_v$1.7 NUCLEIC ACID METHODS

CROSS REFERENCE TO RELATED APPLICATIONS

This application claims benefit of priority to U.S. Provisional Application No. 60/538,149, filed Jan. 21, 2004. U.S. Provisional Application No. 60/538,149 is incorporated by reference herein in its entirety.

ACKNOWLEDGEMENTS

This invention was made with government support under federal grant R01-NS-32666 awarded by the National Institutes of Health. The Government has certain rights to this invention.

BACKGROUND

Voltage-gated sodium channels are transmembrane proteins that mediate regenerative inward currents that are responsible for the initial depolarization of action potentials in excitable cells, such as neurons and muscle. Sodium channels are typically a complex of various subunits, the principle one being the alpha-subunit. The alpha-subunit is the pore-forming subunit, and it alone is sufficient for all known sodium channel function. However, in certain sodium channels, smaller, auxiliary subunits called beta-subunits are known to associate with the larger alpha-subunit and are believed to modulate some of the functions of the alpha-subunit. (See Kraner, et al. (1985) J Biol Chem 260:6341-6347; Tanaka, et al. (1983) J Biol Chem 258:7519-7526; Hartshorne, et al. (1984) J Biol Chem 259:1667-1675; Catterall, (1992) Physiol Rev 72:S14-S48; Anderson, et al. (1992) Physiol Rev 72:S89-S158.) A review of sodium channels is presented in Catterall, (1995) Ann Rev Biochem 64:493-531.

The primary structures of sodium channel alpha-subunits from a variety of tissues (brain, peripheral nerve, skeletal muscle, and cardiac muscle) and organisms jellyfish, squid, eel, rat, human) have been identified, and their amino acid sequences show individual regions which have been conserved over a long evolutionary period (see Alberts, et al., eds., "Molecular Biology of the Cell" 534-535, Garland Pub., New York, N.Y. (1994)). From these studies it is known that the alpha-subunit of a sodium channel is a large glycoprotein containing four homologous domains (labeled I-IV in FIG. 1) connected by intracellular loops. The N-terminus of the alpha-subunit extends intracellularly at domain I (i.e., DI) and the C-terminus of the alpha-subunit extends intracellularly at domain IV (i.e., DIV). In the plasma membrane, the four domains orient in such a way as to create a central pore whose structural constituents determine the selectivity and conductance properties of the sodium channel.

Each domain of the sodium channel alpha-subunit contains six transmembrane alpha-helices or segments (labeled 1-6 in FIG. 1). Five of these transmembrane segments are hydrophobic, whereas one segment is positively charged with several lysine or arginine residues. This highly charged segment is the fourth transmembrane segment in each domain. Extracellular loops connect segment 1 (i.e., S1) to segment 2 (i.e., S2) and segment 3 (i.e., S3) to segment 4 (i.e., S4). Intracellular loops connect S2 to S3 and S4 to segment 5 (i.e., S5). An extracellular re-enterant loop connects S5 to segment 6 (i.e., S6). (See Agnew, et al. (1978) Proc Natl Acad Sci USA 75:2606-2610; Agnew, et al. (1980) Biochem Biophys Res Comm 92:860-866; Catterall, (1986) Ann Rev Biochem 55:953-985; Catterall, (1992) Physiol Rev 72:S14-S48.)

Voltage-gated sodium channels can be named according to a standardized form of nomenclature outlined in Goldin, et al. (2000) Neuron 28:365-368. According to that system, voltage-gated sodium channels are grouped into one family from which nine mammalian isoforms and have been identified and expressed. These nine isoforms are given the names Na$_v$1.1 through Na$_v$1.9. Also, splice variants of the various isoforms are distinguished by the use of lower case letters following the numbers (e.g., "Na$_v$1.1a").

Because of the important role sodium channels play in the transmission of action potentials in excitable cells like neurons and muscle, sodium channels have been implicated in many sensory, motor, and neurologic disorders. Accordingly, sodium channels have been the focus of much scientific research. However, while a great deal has been learned about sodium channels, there remains a need for further understanding of the functioning of sodium channels, and means to diagnose, predict, prevent, and treat diseases, disorders, and conditions that result from variations and abnormalities of sodium channels. These and other objects and advantages of the materials, compositions, articles, devices, and methods described herein, as well as additional inventive features, will be apparent from the following disclosure.

SUMMARY

In accordance with the purposes of the disclosed materials, compositions, articles, devices, and methods, as embodied and broadly described herein, the disclosed subject matter, in one aspect, relates to a method of characterizing a nucleic acid sequence that encodes a Na$_v$1.7 sodium channel alpha-subunit, wherein the method comprises the step of identifying mutations at one or more sites in regions of the nucleic acid sequence that encode an intracellular N-terminal region, an extracellular loop in domain I, an intracellular loop between domains I and II, an intracellular loop between domains II and III, an intramembrane region of domain II, or any combination thereof, such identified nucleotides indicating the character of the nucleic acid sequence.

In another aspect, the disclosed subject matter relates to a method for determining a Na$_v$1.7 haplotype in a human subject, wherein the method comprises identifying one or more nucleotides encoding amino acid residues 62, 149, 641, 655, 739, 1123, or any combination thereof, wherein the nucleotide or nucleotides indicate the haplotype.

In yet another aspect, the disclosed subject matter relates to a method for determining a subject's predisposition to a neurologic disorder associated with a sodium channel mutation comprising comparing the subject's Na$_v$1.7 haplotype with one or more reference haplotypes that correlate with the neurologic disorder, a similar haplotype in the subject's Na$_v$1.7 haplotype as compared to the reference haplotype or haplotypes indicating a predisposition to the neurologic disorder.

In a still further aspect, described herein is a method of identifying a compound that modulates mutant Na$_v$1.7 sodium channels, wherein the method comprises contacting with a test compound a cell containing a mutant Na$_v$1.7 nucleic acid that encodes a mutant Na$_v$1.7 sodium channel comprising one or more mutations at residue 62, residue 149, residue 641, residue 655, residue 739, or residue 1123, detecting Na$_v$1.7 sodium channel activity, and comparing the Na$_v$1.7 sodium channel activity in the contacted cell with the amount of Na$_v$1.7 sodium channel activity in a control cell, wherein the control cell is not contacted by the test compound, an increased or decreased Na$_v$1.7 sodium channel activity in the test cell as compared to the control cell indicating a compound that modulates mutant $Na_v1.7$ sodium channels.

Also, described herein are isolated nucleic acids comprising nucleotide sequences encoding mutant $Na_v1.7$ sodium channel alpha-subunits, expression vectors made from such nucleic acids, cultured cells comprising such vectors, and methods of making mutant $Na_v1.7$ sodium channel alpha-subunits comprising culturing such cells under conditions allowing expression of the polypeptide encoded by the nucleic acids, wherein the polypeptide comprises a mutant $Na_v1.7$ sodium channel alpha-subunit. Further, described herein are isolated polypeptides comprising mutant $Na_v1.7$ sodium channel alpha-subunits and fragments thereof as well as purified antibodies that bind to epitopes of such mutant $Na_v1.7$ sodium channel alpha-subunits.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF DRAWINGS

The accompanying drawings, which are incorporated in and constitute a part of this specification, illustrate several aspects described below.

DETAILED DESCRIPTION

Figure 1:
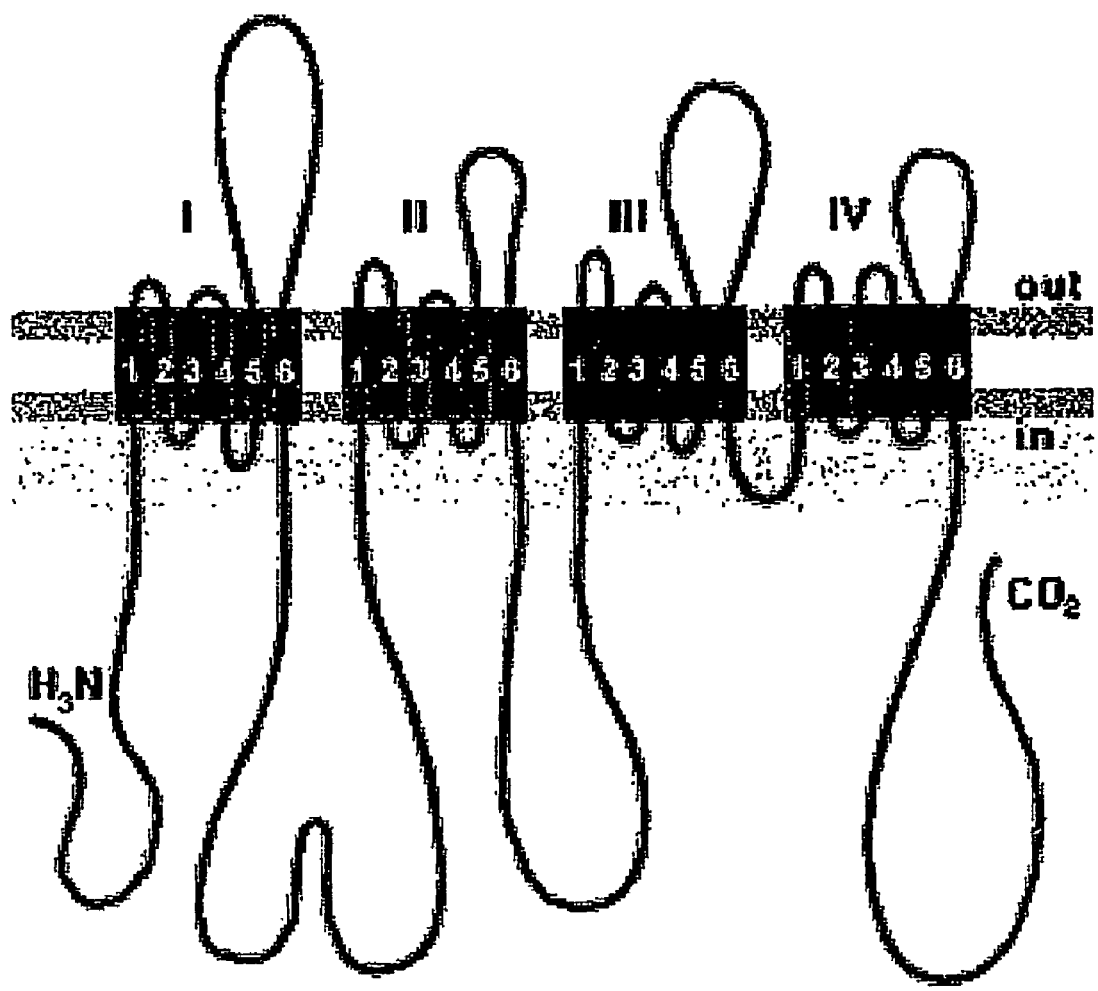
FIG. 1 is a diagram of the secondary structure of a sodium channel alpha-subunit. Not shown is the pore region in each of the four domains, which consists of an inward loop between transmembrane regions 5 and 6.

The materials, compositions, articles, devices, and methods described herein may be understood more readily by reference to the following detailed description of specific aspects of the disclosed subject matter, and methods and the Examples included therein and to the Figures and their previous and following description.

Before the present materials, compositions, articles, devices, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Disclosed herein are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a $Na_v1.7$ sodium channel is disclosed and a number of modifications that can be made to a number of amino acid residues or nucleotides, including those related to the mutant $Na_v1.7$ sodium channel are discussed, each and every combination and permutation that are possible are specifically contemplated unless specifically indicated to the contrary. Thus, if a class of substituents A, B, and C are disclosed as well as a class of substituents D, E, and F and an example of a combination molecule, A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

Throughout this specification, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

Definitions

In this specification and in the claims that follow, reference will be made to a number of terms, which shall be defined to have the following meanings:

As used in the specification and the appended claims, the singular forms "a," "an," and "the" include plural referents unless the context clearly dictates otherwise. Thus, for example, reference to "a nucleotide" includes mixtures of two or more such nucleotides, reference to "an amino acid" includes mixtures of two or more such amino acids, reference to "the sodium channel" includes mixtures of two or more such sodium channels, and the like.

"Optional" or "optionally" means that the subsequently described event or circumstance can or cannot occur, and that the description includes instances where the event or circumstance occurs and instances where it does not. For example, the phrase "the array can optionally comprise the most commonly found allele at a second . . . position" means that the most commonly found allele at a second position may or may not be present in the array and that the description includes both arrays without the most commonly found allele at the second position and arrays where there is the most commonly found allele at the second position.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

"Subject," as used herein, means an individual. In one aspect, the subject is a mammal such as a primate, and, in another aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, etc.).

"$Na_v1.7$," as used herein, refers to an isoform of a sodium channel known in the art by names such as NaS, hNE-Na, and PN1. The traditional gene symbol for a $Na_v1.7$ sodium channel is SCN9A, and thus the term $Na_v1.7$, as used herein, is synonymous with the term SCN9A. There are a variety of sequences related to the $Na_v1.7$ gene having the following Genbank Accession Numbers: NM 002977 (human), U35238 (rabbit), X82835 (human), U79568 (rat), and AF000368 (rat), these nucleic acid sequences, the polypeptides encoded by them, and other nucleic acid and polypeptide sequences are herein incorporated by reference in their entireties as well as for individual subsequences contained therein.

There are a variety of compositions disclosed herein that are amino acid based, including for example $Na_v1.7$ sodium channel alpha-subunits. Thus, as used herein, "amino acid," means the typically encountered twenty amino acids which make up polypeptides. In addition, it further includes less typical constituents which are both naturally occurring, such as, but not limited to formylmethionine and selenocysteine, analogs of typically found amino acids, and mimetics of amino acids or amino acid functionalities. Non-limiting examples of these and other molecules are discussed herein.

As used herein, the terms "peptide" and "polypeptide" refer to a class of compounds composed of amino acids chemically bound together. Non-limiting examples of these and other molecules are discussed herein. In general, the amino acids are chemically bound together via amide linkages (CONH); however, the amino acids may be bound together by other chemical bonds known in the art. For example, the amino acids may be bound by amine linkages. Peptide as used herein includes oligomers of amino acids and small and large peptides, including polypeptides and proteins.

There are a variety of compositions disclosed herein that are nucleic acid based, including for example the nucleic acids that encode, for example, $Na_v1.7$ sodium channel alpha-subunits. Thus, as used herein, "nucleic acid" means a molecule made up of, for example, nucleotides, nucleotide analogs, or nucleotide substitutes. Non-limiting examples of these and other molecules are discussed herein. A nucleic acid can be double stranded or single stranded. It is understood that, for example, when a vector is expressed in a cell the expressed mRNA will typically be made up of A, C, G, and U. Likewise, it is understood that if, for example, an antisense molecule is introduced into a cell or cell environment through, for example, exogenous delivery, it is advantageous that the antisense molecule be made up of nucleotide analogs that reduce the degradation of the antisense molecule in the cellular environment.

As used herein, "nucleotide" is a molecule that contains a base moiety, a sugar moiety and a phosphate moiety. Nucleotides can be linked together through their phosphate moieties and sugar moieties creating an internucleoside linkage. The base moiety of a nucleotide can be adenine-9-yl (A), cytosine-1-yl (C), guanine-9-yl (G), uracil-1-yl (U), and thymin-1-yl (T). The sugar moiety of a nucleotide is a ribose or a deoxyribose. The phosphate moiety of a nucleotide is pentavalent phosphate. A non-limiting example of a nucleotide would be 3'-AMP (3'-adenosine monophosphate) or 5'-GMP (5'-guanosine monophosphate).

"Nucleotide analog," as used herein, is a nucleotide which contains some type of modification to either the base, sugar, or phosphate moieties. Modifications to nucleotides are well known in the art and would include for example, 5-methyl-cytosine (5-me-C), 5-hydroxymethyl cytosine, xanthine, hypoxanthine, and 2-aminoadenine as well as modifications at the sugar or phosphate moieties.

"Nucleotide substitutes," as used herein, are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety (Letsinger, et al. (1989) Proc Natl Acad Sci USA, 86:6553-6556.)

A "Watson-Crick interaction" is at least one interaction with the Watson-Crick face of a nucleotide, nucleotide analog, or nucleotide substitute. The Watson-Crick face of a nucleotide, nucleotide analog, or nucleotide substitute includes the C2, N1, and C6 positions of a purine based nucleotide, nucleotide analog, or nucleotide substitute and the C2, N3, C4 positions of a pyrimidine based nucleotide, nucleotide analog, or nucleotide substitute.

A "Hoogsteen interaction" is the interaction that takes place on the Hoogsteen face of a nucleotide or nucleotide analog, which is exposed in the major groove of duplex DNA. The Hoogsteen face includes the N7 position and reactive groups ($NH_2$ or O) at the C6 position of purine nucleotides.

"Deletion," as used herein, refers to a change in an amino acid or nucleotide sequence in which one or more amino acid or nucleotide residues, respectively, are absent relative to the reference sequence.

"Insertion" or "addition," as used herein, refers to a change in an amino acid or nucleotide sequence resulting in the addition of one or more amino acid or nucleotide residues, respectively, as compared to the reference sequence.

"Substitution," as used herein, refers to the replacement of one or more amino acids or nucleotides by one or more different amino acids or nucleotides, respectively, in a reference sequence.

"Isolated," as used herein refers to material, such as a nucleic acid or a polypeptide, which is: (1) substantially or essentially free from components which normally accompany or interact with it as found in its naturally occurring environment. Although, the isolated material optionally comprises material not found with the material in its natural environment; or (2) if the material is in its natural environment, the material has been synthetically (non-naturally) altered by deliberate human intervention to a composition and/or placed at a locus in the cell (e.g., genome or subcellular organelle) not native to a material found in that environment. The alteration to yield the synthetic material can be performed on the material within or removed from its natural state.

Characterizing Mutant $Na_v1.7$ Nucleic Acid Sequences

It has been found that, in certain neurologic disorders, specific sites in the $Na_v1.7$ gene are mutated, i.e., the nucleotide at a specific position or at specific positions differs from that observed in the most commonly found $Na_v1.7$ gene sequence. Accordingly, disclosed herein are methods of characterizing mutant nucleic acid sequences that encode a $Na_v1.7$ sodium channel alpha-subunit and the use of such nucleic acids to diagnose and treat disease states and neurologic disorders, such as seizures.

In one aspect, disclosed herein is a method of characterizing a nucleic acid sequence that encodes a $Na_v1.7$ sodium channel alpha-subunit, comprising the step of identifying mutations at one or more sites in regions of the nucleic acid sequence that encode various regions of the $Na_v1.7$ sodium channel alpha-subunit. While mutations can be present in any region of the $Na_v1.7$ nucleic acid sequence, specific regions of the nucleic acid sequence where mutations can be identified include, but are not limited to, those regions that encode an intracellular N-terminal region, an extracellular loop in domain I, an intracellular loop between domains I and II, an intracellular loop between domains II and III, an intramembrane region of domain II, or any combination thereof. Such identified nucleotides can indicate the character of the nucleic acid sequence.

The terms "mutation" and "mutant," as used herein, mean that, at one or more specific positions in a nucleic acid or amino acid sequence, a nucleotide or amino acid that differs from the most commonly found nucleotide or amino acid can be identified. A mutation includes deletions, additions, insertions, and substitutions in the nucleotide or amino acid sequence. For example, in one particular mutant $Na_v1.7$ nucleic acid sequence disclosed herein, position 184 of the nucleic acid sequence contains a substitution; that is, the most commonly found nucleotide at position 184 of the $Na_v1.7$ gene is A, whereas in the mutant $Na_v1.7$ nucleic acid sequence, the nucleotide found at position 184, i.e., the mutated site, is G. One of skill in the art can analyze position 184 and determine which of the two amino acids (A or G) is present. As another example, in one particular mutant $Na_v1.7$ sodium channel alpha-subunit disclosed herein, position 62 of the amino acid sequence contains a substitution; that is, the most commonly found amino acid at position 62 of the $Na_v1.7$ amino acid sequence is isoleucine, whereas in the mutant $Na_v1.7$ amino acid sequence, the amino acid found at position 62, i.e., the mutated site, is valine. Also, one of skill in the art can analyze position 62 of the amino acid sequence and determine which of the two amino acids (isoleucine or valine) is present. Further, as used herein, "mutant" also includes combinations of mutations at more than one position in the $Na_v1.7$ nucleic acid or amino acid sequence. Mutations may provide functional differences in the genetic sequence, through changes in the encoded polypeptide, changes in mRNA stability, binding of transcriptional and translation factors to the DNA or RNA, and the like. The mutations can also be used as single nucleotide or single amino acid mutations to detect genetic linkage to phenotypic variation in activity and expression of sodium channels.

As utilized herein, the "character" of the $Na_v1.7$ nucleic acid sequence can be the combination of nucleotides present at mutated sites that make up the $Na_v1.7$ sodium channel alpha-subunit haplotype as well as the biological activity associated with a particular mutation or combination of mutations.

In one specific aspect, a mutation can be present in the nucleic acid region encoding the intracellular N-terminus region of the $Na_v1.7$ sodium channel alpha-subunit. For example, such a mutation can be at the site that encodes amino acid residue 62. The mutated site can be at position 184 of the $Na_v1.7$ nucleic acid sequence. In one particular aspect, the mutation can encode a valine at amino acid residue 62.

In another aspect, a mutation can be present in the nucleic acid region encoding the extracellular loop of domain I of the $Na_v1.7$ sodium channel alpha-subunit. For example, such a mutation can be at the site that encodes amino acid residue 149. The mutated site can be at position 446 of the $Na_v1.7$ nucleic acid sequence. In one specific aspect, the mutation can encode a glutamine at amino acid residue 149.

In yet another aspect, mutations can be present in the nucleic acid region encoding the intracellular loop between domains I and II of the $Na_v1.7$ sodium channel alpha-subunit. For example, such mutations can be at sites that encode amino acid residue 641 and/or amino acid residue 655. The mutated sites can be at positions 1921 and/or 1964 of the $Na_v1.7$ nucleic acid sequence. In one specific aspect, the mutation can encode a tyrosine at amino acid residue 641. In another aspect, the mutation can encode an arginine at amino acid residue 655.

In a further aspect, a mutation can be present in the nucleic acid region encoding the intramembrane region of domain II of the $Na_v1.7$ sodium channel alpha-subunit. For example, such a mutation can be at the site that encodes amino acid residue 739. The mutated site can be at position 2215 of the $Na_v1.7$ nucleic acid sequence. In one specific aspect, the mutation can encode a valine at amino acid residue 739.

In still another aspect, a mutation can be present in the nucleic acid region encoding the intracellular loop between domains II and III of the $Na_v1.7$ sodium channel alpha-subunit. For example, such a mutation can be at the site that encodes amino acid residue 1123. The mutated site can be at position 3369 of the $Na_v1.7$ nucleic acid sequence. In one specific aspect, the mutation can encode a phenylalanine at amino acid residue 1123.

Mutations can also be present in more than one region of the nucleic acid sequence, such as in regions that encode an intracellular N-terminal region and an extracellular loop in domain I; an intracellular N-terminal region and an intracellular loop between domains I and II; an intracellular N-terminal region and an intracellular loop between domains II and III; an intracellular N-terminal region and an intramembrane region of domain II; an extracellular loop in domain I and an intracellular loop between domains I and II; an extracellular loop in domain I and an intracellular loop between domains II and III; an extracellular loop in domain I and an intramembrane region of domain II; an intracellular loop between domains I and II and an intracellular loop between domains II and III; an intracellular loop between domains I and II and an intramembrane region of domain II; and an intracellular loop between domains II and III and an intramembrane region of domain II.

Some of the mutations that can be identified by the methods disclosed herein include, but are not limited to, mutations at positions 184, 446, 1921, 1964, 2215, 3369, or any combination thereof, of the Na$_v$1.7 nucleic acid sequence. Any individual mutation can be analyzed at any of these positions, or combinations of mutant variants at more than one position can be identified and analyzed by the methods disclosed herein.

A number of methods are available for analyzing nucleic acids for the presence of a specific sequence. For all of the methods described herein, genomic DNA can be extracted from a sample and this sample can be from any organism and can be, but is not limited to, peripheral blood, bone marrow specimens, primary tumors, embedded tissue sections, frozen tissue sections, cell preparations, cytological preparations, exfoliate samples (e.g., sputum), fine needle aspirations, amnion cells, fresh tissue, dry tissue, and cultured cells or tissue. Such samples can be obtained directly from a subject, commercially obtained or obtained via other means. Thus, the methods described herein can be utilized to analyze a nucleic acid sample that comprises genomic DNA, amplified DNA (such as a PCR product), cDNA, cRNA, a restriction fragment or any other desired nucleic acid sample. When one performs one of the herein described methods on genomic DNA, typically the genomic DNA will be treated in a manner to reduce viscosity of the DNA and allow better contact of a primer or probe with the target region of the genomic DNA. Such reduction in viscosity can be achieved by any desired methods, which are known to the skilled artisan, such as DNase treatment or shearing of the genomic DNA, preferably lightly.

If sufficient DNA is available, genomic DNA can be used directly. Alternatively, the region of interest is cloned into a suitable vector and grown in sufficient quantity for analysis. The nucleic acid may be amplified by conventional techniques, such as the polymerase chain reaction (PCR), to provide sufficient amounts for analysis. A variety of PCR techniques are familiar to those skilled in the art. For a review of PCR technology, see the publication entitled "PCR Methods and Applications" (1991, Cold Spring Harbor Laboratory Press), which is incorporated herein by reference in its entirety for amplification methods. In each of these PCR procedures, PCR primers on either side of the nucleic acid sequences to be amplified are added to a suitably prepared nucleic acid sample along with dNTPs and a thermostable polymerase such as Taq polymerase, Pfu polymerase, or Vent polymerase. The nucleic acid in the sample is denatured and the PCR primers are specifically hybridized to complementary nucleic acid sequences in the sample. The hybridized primers are extended. Thereafter, another cycle of denaturation, hybridization, and extension is initiated. The cycles are repeated multiple times to produce an amplified fragment containing the nucleic acid sequence between the primer sites. PCR has further been described in several patents including U.S. Pat. Nos. 4,683,195, 4,683,202, and 4,965,188. Each of these publications is incorporated herein by reference in its entirety for PCR methods. One of skill in the art would know how to design and synthesize primers flanking any of the nucleic acid sequences disclosed herein.

For example, the disclosed method provides primers GTCCCGCCCATTGCCTGACAC (SEQ ID NO: 20) and TTCTGGTCATGATATGGTTATTCAC (SEQ ID NO: 21), which can be utilized to amplify the region of the Na$_v$1.7 nucleic acid sequence comprising nucleotide position 184 in order to identify a mutation at this site. The disclosed method also provides primers TGATAGATGCGTTGATGACATTGG (SEQ ID NO: 22) and TTCATAAATGCAGTAACTTCCTGG (SEQ ID NO: 23), which can be utilized to amplify the region of the Na$_v$1.7 nucleic acid sequence comprising nucleotide position 446 in order to identify a mutation at this site.

Also, the disclosed method provides primers TGTTTCTTTTAAGTCAGTACAGAG (SEQ ID NO: 24) and AGAGCCATTCACAAGACCAGAG (SEQ ID NO: 25), which can be utilized to amplify the region of the Na$_v$1.7 nucleic acid sequence comprising nucleotide position 1921 in order to identify a mutation at this site. Additionally, the disclosed method provides primers ACTCAGAAAGGCAGAGAGGTG (SEQ ID NO: 26) and TTGCCATGTTATCAATGTCTGTG (SEQ ID NO: 27), which can be utilized to amplify the region of the Na$_v$1.7 nucleic acid sequence comprising nucleotide position 1964 in order to identify a mutation at this site. Further, the disclosed method provides primers GACTGATTTGTATCTGGTTAGGAG (SEQ ID NO: 28) and GCAATGTAATTAGGAAGGTGTGAG (SEQ ID NO: 29), which can be utilized to amplify the region of the Na$_v$1.7 nucleic acid sequence comprising nucleotide position 2215 in order to identify a mutation at this site. For example, the disclosed method provides primers TTTGAATGAACTCTAAATGAACTACC (SEQ ID NO: 30) and TAAGTATTAGGCGTTAAGACAAACC (SEQ ID NO: 31), which can be utilized to amplify the region of the Na$_v$1.7 nucleic acid sequence comprising nucleotide position 3369 in order to identify a mutation at this site. One of skill in the art would know how to design primers accordingly to amplify any region of the Na$_v$1.7 nucleic acid sequence for the purposes of identifying a mutation at any nucleotide position throughout the Na$_v$1.7 sodium channel alpha-subunit sequence. Amplification may also be used to determine whether a mutation is present by using a primer that is specific for the mutation.

Various methods are known in the art that utilize oligonucleotide ligation as a means of detecting mutations, for examples see Riley, et al. (1990) Nucleic Acids Res 18:2887-2890; and Delahunty, et al. (1996) Am J Hum Genet. 58:1239-1246, which are incorporated herein by reference in their entirety for methods of detecting mutations. Such methods include single base chain extension (SBCE), oligonucleotide ligation assay (OLA) and cleavage reaction/signal release (Invader methods, Third Wave Technologies).

LCR and Gap LCR are exponential amplification techniques. Both depend on DNA ligase to join adjacent primers annealed to a DNA molecule. In Ligase Chain Reaction (LCR), probe pairs are used which include two primary (first and second) and two secondary (third and fourth) probes, all of which are employed in molar excess to target. The first probe hybridizes to a first segment of the target strand and the second probe hybridizes to a second segment of the target strand, the first and second segments being contiguous so that the primary probes abut one another in 5'-phosphate-3'-hydroxyl relationship, and so that a ligase can covalently fuse or ligate the two probes into a fused product. In addition, a third (secondary) probe can hybridize to a portion of the first probe and a fourth (secondary) probe can hybridize to a portion of the second probe in a similar abutting fashion. Of course, if the target is initially double stranded, the secondary probes also will hybridize to the target complement in the first instance. Once the ligated strand of primary probes is separated from the target strand, it will hybridize with the third and fourth probes, which can be ligated to form a complementary, secondary ligated product. It is important to realize that the ligated products are functionally equivalent to either the target or its complement. By repeated cycles of hybridization and ligation, amplification of the target sequence is achieved. A method for multiplex LCR has also been described (WO 9320227, which is incorporated herein by reference in its entirety for the methods taught therein). Gap LCR (GLCR) is a version of LCR where the probes are not adjacent but are separated by 2 to 3 bases.

A method for typing single nucleotide mutations in DNA, labeled Genetic Bit Analysis (GBA), has been described in Nikiforov, et al. (1994) Nucleic Acid Res 22:4167-4175. In this method, specific fragments of genomic DNA containing the mutated site(s) are first amplified by the polymerase chain reaction (PCR) using one regular and one phosphorothioate-modified primer. The double-stranded PCR product is rendered single-stranded by treatment with the enzyme T7 gene 6 exonuclease, and captured onto individual wells of a 96 well polystyrene plate by hybridization to an immobilized oligonucleotide primer. This primer is designed to hybridize to the single-stranded target DNA immediately adjacent from the mutated site of interest. Using the Klenow fragment of E. coli DNA polymerase I or the modified T7 DNA polymerase (Sequenase), the 3' end of the capture oligonucleotide is extended by one base using a mixture of one biotin-labeled, one fluorescein-labeled, and two unlabeled dideoxynucleoside triphosphates. Antibody conjugates of alkaline phosphatase and horseradish peroxidase are then used to determine the nature of the extended base in an ELISA format. Additionally, minisequencing with immobilized primers has been utilized for detection of mutations in PCR products (see Pastinen, et al. (1997) Genome Res 7:606-614).

The effect of phosphorothioate bonds on the hydrolytic activity of the 5'->3' double-strand-specific T7 gene 6 exonuclease is used in order to improve upon GBA. The use of phosphorothioate primers and exonuclease hydrolysis for the preparation of single-stranded PCR products and their detection by solid-phase hybridization can be used. (See Nikiforov, et al. (1994) PCR Methods and Applications 3:285-291.) Double-stranded DNA substrates containing one phosphorothioate residue at the 5' end were found to be hydrolyzed by this enzyme as efficiently as unmodified ones. The enzyme activity was, however, completely inhibited by the presence of four phosphorothioates. On the basis of these results, a method for the conversion of double-stranded PCR products into full-length, single-stranded DNA fragments was developed. In this method, one of the PCR primers contains four phosphorothioates at its 5' end, and the opposite strand primer is unmodified. Following the amplification, the double-stranded product is treated with T7 gene 6 exonuclease. The phosphorothioated strand is protected from the action of this enzyme, whereas the opposite strand is hydrolyzed. When the phosphorothioated PCR primer is 5' biotinylated, the single-stranded PCR product can be easily detected calorimetrically after hybridization to an oligonucleotide probe immobilized on a microtiter plate. A simple and efficient method for the immobilization of relatively short oligonucleotides to microtiter plates with a hydrophilic surface in the presence of salt can be used.

DNA analysis based on template hybridization (or hybridization plus enzymatic processing) to an array of surface-bound oligonucleotides is well suited for high density, parallel, low cost and automatable processing (Ives, et al. (1996) Proc SPIE-Int Soc Opt Eng 2680 (Ultrasensitive Biochemical Diagnostics) 258-269). Direct fluorescence detection of labeled DNA provides the benefits of linearity, large dynamic range, multianalyte detection, processing simplicity and safe handling at reasonable cost. The Molecular Tool Corporation has applied a proprietary enzymatic method of solid phase genotyping to DNA processing in 96-well plates and glass microscope slides. Detecting the fluor-labeled GBA dideoxynucleotides requires a detection limit of approximately 100 mols/$\mu m^2$. Commercially available plate readers detect about 1000 mols/$\mu m^2$, and an experimental setup with an argon laser and thermoelectrically-cooled CCD can detect approximately 1 order of magnitude less signal. The current limit is due to glass fluorescence. Dideoxynucleotides labeled with fluorescein, eosin, tetramethylrhodamine, Lissamine and Texas Red have been characterized, and photobleaching, quenching and indirect detection with fluorogenic substrates have been investigated.

Other amplification techniques that can be used in the context of the present invention include, but are not limited to, Q-beta amplification as described in European Patent Application No 4544610, strand displacement amplification as described in EP 684 315A and, target mediated amplification as described in PCT Publication WO 9322461, the disclosures of which are incorporated herein by reference in their entirety for the methods taught therein.

Allele specific amplification can also be utilized for biallelic markers. Discrimination between the two alleles of a biallelic marker can also be achieved by allele specific amplification, a selective strategy, whereby one of the alleles is amplified without amplification of the other allele. For allele specific amplification, at least one member of the pair of primers is sufficiently complementary with a region of a reference sequence (i.e., $Na_v1.7$) comprising the polymorphic base of a biallelic marker of the present invention to hybridize therewith. Such primers are able to discriminate between the two alleles of a biallelic marker. This can be accomplished by placing the mutated base at the 3' end of one of the amplification primers. Such allele specific primers tend to selectively prime an amplification or sequencing reaction so long as they are used with a nucleic acid sample that contains one of the two alleles present at a biallelic marker because the extension forms from the 3' end of the primer, a mismatch at or near this position has an inhibitory effect on amplification. Therefore, under appropriate amplification conditions, these primers only direct amplification on their complementary allele. Determining the precise location of the mismatch and the corresponding assay conditions are well with the ordinary skill in the art.

A detectable label may be included in an amplification reaction. Suitable labels include fluorochromes, e.g., fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g., 32 P, 35 S, 3H; etc. The label may be a two stage system, where the amplified DNA is conjugated to biotin, haptens, etc. having a high affinity binding partner, e.g., avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid, e.g., amplified or cloned fragment, can be analyzed by one of a number of methods known in the art. The nucleic acid can be sequenced by dideoxy or other methods. Hybridization with the variant sequence can also be used to determine its presence, by Southern blots, dot blots, etc. The hybridization pattern of a control (reference) and variant sequence to an array of oligonucleotide probes immobilized on a solid support, as described in U.S. Pat. No. 5,445,934 and WO 95/35505, which are incorporated herein by reference in their entirety for the methods, may also be used as a means of detecting the presence of variant sequences. Single strand conformational polymorphism (SSCP) analysis, denaturing gradient gel electrophoresis (DGGE), mismatch cleavage detection, and heteroduplex analysis in gel matrices are used to detect conformational changes created by DNA sequence variation as alterations in electrophoretic mobility. Alternatively, where a mutation creates or destroys a recognition site for a restriction endonuclease (restriction fragment length polymorphism, RFLP), the sample is digested with that endonuclease, and the products size fractionated to determine whether the fragment was digested. Fractionation is performed by gel or capillary electrophoresis, particularly acrylamide or agarose gels.

The disclosed materials, compositions, and methods also provide the use of the nucleic acid sequences described herein in methods using a mobile solid support to analyze mutations. See, for example, WO 01/48244, which is incorporated herein by reference in its entirety for the methods taught therein.

The method of performing a Luminex FlowMetrix-based SNP analysis involves differential hybridization of a PCR product to two differently-colored FACS-analyzable beads. The FlowMetrix system currently consists of uniformly-sized 5 micron polystyrene-divinylbenzene beads stained in eight concentrations of two dyes (orange and red). The matrix of the two dyes in eight concentrations allows for 64 differently-colored beads that can each be differentiated by a FACScalibur suitably modified with the Luminex PC computer board. In the Luminex SNP analysis, covalently-linked to a bead is a short (approximately 18-20 bases) "target" oligodeoxynucleotide (oligo). The nucleotide positioned at the center of the target oligo encodes the polymorphic base. A pair of beads are synthesized; each bead of the pair has attached to it one of the polymorphic oligonucleotides. A PCR of the region of DNA surrounding the to-be analyzed SNP is performed to generate a PCR product. Conditions are established that allow hybridization of the PCR product preferentially to the bead on which is encoded the precise complement. In one format ("without competitor"), the PCR product itself incorporates a flourescein dye and it is the gain of the flourescein stain on the bead, as measured during the FACScalibur run, that indicates hybridization. In a second format ("with competitor,") the beads are hybridized with a competitor to the PCR product. The competitor itself in this case is labeled with flourescein. And it is the loss of the flourescein by displacement by unlabeled PCR product that indicates successful hybridization.

Isolated $Na_v1.7$ Nucleic Acid Sequences

The nucleic acid sequences disclosed herein can be isolated by methods known in the art and described herein. In one aspect, disclosed herein are isolated nucleic acids comprising nucleotide sequences encoding mutant $Na_v1.7$ sodium channel alpha-subunits. For example, in one aspect, disclosed herein is an isolated nucleic acid sequence comprising a nucleotide sequence encoding the amino acid sequence of SEQ ID NO: 2. In another aspect, disclosed herein is an isolated nucleic acid sequence comprising a nucleotide sequence encoding the amino acid sequence of SEQ ID NO: 3. In yet another aspect, disclosed herein is an isolated nucleic acid sequence comprising a nucleotide sequence encoding the amino acid sequence of SEQ ID NO: 4. In a further aspect, disclosed herein is an isolated nucleic acid sequence comprising a nucleotide sequence encoding the amino acid sequence of SEQ ID NO: 5. In a still further aspect, disclosed herein is an isolated nucleic acid sequence comprising a nucleotide sequence encoding the amino acid sequence of SEQ ID NO: 6. In one aspect, disclosed herein is an isolated nucleic acid sequence comprising a nucleotide sequence encoding the amino acid sequence of SEQ ID NO: 7.

Also, disclosed herein is an isolated nucleic acid comprising a nucleotide sequence encoding at least 5 contiguous residues of the $Na_v1.7$ sodium channel alpha-subunit. For example, in one aspect, disclosed herein is an isolated nucleic acid comprising a nucleotide sequence encoding at least 5 contiguous residues of the amino acid sequence of SEQ ID NO: 2, wherein one of the amino acid residues comprises a valine in a position that corresponds to position 62 in SEQ ID NO: 2. In another aspect, disclosed herein is an isolated nucleic acid comprising a nucleotide sequence encoding at least 5 contiguous residues of the amino acid sequence of SEQ ID NO: 3, wherein one of the amino acid residues comprises a glutamine in a position that corresponds to position 149 in SEQ ID NO: 3. In yet another aspect, disclosed herein is an isolated nucleic acid comprising a nucleotide sequence encoding at least 5 contiguous residues of the amino acid sequence of SEQ ID NO: 4, wherein one of the amino acid residues comprises a tyrosine in a position that corresponds to position 641 in SEQ ID NO: 4. In a further aspect, disclosed herein is an isolated nucleic acid comprising a nucleotide sequence encoding at least 5 contiguous residues of the amino acid sequence of SEQ ID NO: 5, wherein one of the amino acid residues comprises a arginine in a position that corresponds to position 655 in SEQ ID NO: 5. In a still further aspect, disclosed herein is an isolated nucleic acid comprising a nucleotide sequence encoding at least 5 contiguous residues of the amino acid sequence of SEQ ID NO: 6, wherein one of the amino acid residues comprises a valine in a position that corresponds to position 739 in SEQ ID NO: 6. In one aspect, disclosed herein is an isolated nucleic acid comprising a nucleotide sequence encoding at least 5 contiguous residues of the amino acid sequence of SEQ ID NO: 7, wherein one of the amino acid residues comprises a phenylalanine in a position that corresponds to position 1123 in SEQ ID NO: 7.

Reference Nucleic Acid Sequences

Reference sequences of the $Na_v1.7$ gene comprising the most commonly found allele are provided herein. As utilized herein, "reference sequence" refers to a nucleic acid sequence that encodes a $Na_v1.7$ sodium channel alpha-subunit or fragment thereof comprising a specific nucleotide at a particular position(s) in the $Na_v1.7$ nucleic acid sequence. Optionally, the reference sequence comprises the most commonly found nucleotide or allele at the particular position or positions. This reference sequence can be a full-length $Na_v1.7$ nucleic acid sequence or fragments thereof. An example of a full-length human $Na_v1.7$ nucleic acid sequence is provided herein as SEQ ID NO: 1.

The term "wild-type" may also be used to refer to the reference sequence comprising the most commonly found allele. It will be understood by one of skill in the art that the designation as "wild-type" is merely a convenient label for a common allele and should not be construed as conferring any particular property on that form of the sequence.

Alternatively, one of skill in the art can utilize a reference sequence or a fragment thereof comprising a nucleotide or allele that is not the most commonly found nucleotide or allele at a specific nucleotide position(s) in the $Na_v1.7$ nucleic acid sequence or can utilize a reference sequence that comprises alternative nucleotides at a specific position(s). An example of a full-length $Na_v1.7$ nucleic acid sequence that comprises such an alternative nucleotide at position 184 is provided herein as SEQ ID NO: 8. Therefore, when utilizing this reference sequence or a fragment thereof, the nucleotide at position 184 can be A or G. Other examples of full-length $Na_v1.7$ reference sequences that comprise such alternative nucleotides at positions 446, 1921, 1964, 2215, and 3369 are provided herein as SEQ ID NO's: 9, 10, 11, 12, and 13, respectively. Therefore, when utilizing these reference sequences or fragments thereof, respectively, the nucleotide at position 446 can be C or A, the nucleotide at position 1921 can be A or T, the nucleotide at position 1964 can be position A or G, the nucleotide at position 2215 can be A or T, and the nucleotide at position 3369 can be G or T.

In one aspect, the reference sequence can comprise a fragment of the $Na_v1.7$ nucleic acid sequence. For example, disclosed herein is a reference sequence comprising the nucleotide sequence GCCCTTCATCTATGG (SEQ ID NO: 14), corresponding to nucleotides 177 to 191 of the $Na_v1.7$ gene sequence. This reference sequence has an "A" at position 184, which is the most commonly found nucleotide at this position. Therefore, one of skill in the art can compare this reference sequence to a test sequence and determine if the most commonly found nucleotide (A) is present at position 184 of the test sequence or if another nucleotide (G) is present at position 184 of the test sequence. Also provided are nucleotide sequence corresponding to any fragment of SEQ ID NO: 14 that includes the A at position 184 or the corresponding sequence with a G at position 184.

As another example, disclosed herein is a reference sequence comprising the nucleotide sequence AACCCGCCGGACTGG (SEQ ID NO: 15), corresponding to nucleotides 439 to 453 of the $Na_v1.7$ gene sequence. This reference sequence has a "C" at position 446, which is the most commonly found nucleotide at this position. Therefore, one of skill in the art can compare this reference sequence to a test sequence and determine if the most commonly found nucleotide (C) is present at position 446 of the test sequence or if another nucleotide (A) is present at position 446 of the test sequence. Also provided are nucleotide sequence corresponding to any fragment of SEQ ID NO: 15 that includes the C at position 446 or the corresponding sequence with a A at position 446.

Also, disclosed herein is a reference sequence comprising the nucleotide sequence GCTCCCCAATGGACA (SEQ ID NO: 16), corresponding to nucleotides 1914 to 1928 of the $Na_v1.7$ gene sequence. This reference sequence has an "A" at position 1921, which is the most commonly found nucleotide at this position. Therefore, one of skill in the art can compare this reference sequence to a test sequence and determine if the most commonly found nucleotide (A) is present at position 1921 of the test sequence or if another nucleotide (G) is present at position 1921 of the test sequence. Also provided are nucleotide sequence corresponding to any fragment of SEQ ID NO: 16 that includes the A at position 1921 or the corresponding sequence with a G at position 1921.

Further, disclosed herein is a reference sequence comprising the nucleotide sequence ATACACAAGAAAAGG (SEQ ID NO: 17), corresponding to nucleotides 1956 to 1971 of the $Na_v1.7$ gene sequence. This reference sequence has an "A" at position 1964, which is the most commonly found nucleotide at this position. Therefore, one of skill in the art can compare this reference sequence to a test sequence and determine if the most commonly found nucleotide (A) is present at position 1964 of the test sequence or if another nucleotide (G) is present at position 1964 of the test sequence. Also provided are nucleotide sequence corresponding to any fragment of SEQ ID NO: 17 that includes the A at position 1964 or the corresponding sequence with a G at position 1964.

In yet another example, disclosed herein is a reference sequence comprising the nucleotide sequence TCTTGCAATTACCAT (SEQ ID NO: 18), corresponding to nucleotides 2208 to 2222 of the $Na_v1.7$ gene sequence. This reference sequence has an "A" at position 2215, which is the most commonly found nucleotide at this position. Therefore, one of skill in the art can compare this reference sequence to a test sequence and determine if the most commonly found nucleotide (A) is present at position 2215 of the test sequence or if another nucleotide (G) is present at position 2215 of the test sequence. Also provided are nucleotide sequence corresponding to any fragment of SEQ ID NO: 18 that includes the A at position 2215 or the corresponding sequence with a G at position 2215.

In still another example, disclosed herein is a reference sequence comprising the nucleotide sequence ACCCTTTGCCTGGAG (SEQ ID NO: 19), corresponding to nucleotides 3362 to 3376 of the $Na_v1.7$ gene sequence. This reference sequence has a "G" at position 3369, which is the most commonly found nucleotide at this position. Therefore, one of skill in the art can compare this reference sequence to a test sequence and determine if the most commonly found nucleotide (G) is present at position 3369 of the test sequence or if another nucleotide (T) is present at position 3369 of the test sequence. Also provided are nucleotide sequence corresponding to any fragment of SEQ ID NO: 19 that includes the G at position 3369 or the corresponding sequence with a T at position 3369.

Probes and Printers

Nucleic acids of interest comprising the mutations provided herein can be utilized as probes or primers. The complementary sequences of the $Na_v1.7$ nucleic acid sequences disclosed herein are also provided. For the most part, the nucleic acid fragments will be of at least about 15 nucleotides, usually at least about 20 nucleotides, often at least about 50 nucleotides. Such fragments are useful as primers for PCR, hybridization screening, etc. Larger nucleic acid fragments, for example, greater than about 100 nucleotides are useful for production of promoter fragments, motifs, etc. For use in amplification reactions, such as PCR, a pair of primers will be used. The exact composition of primer sequences is not critical to the invention, but for most applications the primers will hybridize to the subject sequence under stringent conditions, as known in the art.

"Probes," as used herein, are molecules capable of interacting with a target nucleic acid, typically in a sequence specific manner, for example, through hybridization. The hybridization of nucleic acids is well understood in the art and is discussed herein. Typically, a probe can be made from any combination of nucleotides or nucleotide derivatives or analogs available in the art.

By "hybridizing under stringent conditions" or "hybridizing under highly stringent conditions" is meant that the hybridizing portion of the hybridizing nucleic acid, typically comprising at least 15 (e.g., 20, 25, 30, or 50 nucleotides), hybridizes to all or a portion of the provided nucleotide sequence under stringent conditions. The term "hybridization" typically means a sequence driven interaction between at least two nucleic acid molecules, such as a primer or a probe and a gene. Sequence driven interaction means an interaction that occurs between two nucleotides or nucleotide analogs or nucleotide derivatives in a nucleotide specific manner. For example, G interacting with C or A interacting with T are sequence driven interactions. Typically sequence driven interactions occur on the Watson-Crick face or Hoogsteen face of the nucleotide. The hybridization of two nucleic acids is affected by a number of conditions and parameters known to those of skill in the art. For example, the salt concentrations, pH, and temperature of the reaction all affect whether two nucleic acid molecules will hybridize. Generally, the hybridizing portion of the hybridizing nucleic acid is at least 80%, for example, at least 90%, 95%, or 98%, identical to the sequence of or a portion of the $Na_v1.7$ nucleic acid of the invention, or its complement. Hybridizing nucleic acids of the invention can be used, for example, as a cloning probe, a primer (e.g., for PCR), a diagnostic probe, or an antisense probe. Hybridization of the oligonucleotide probe to a nucleic acid sample typically is performed under stringent conditions. Nucleic acid duplex or hybrid stability is expressed as the melting temperature or $T_m$, which is the temperature at which a probe dissociates from a target DNA. This melting temperature is used to define the required stringency conditions. If sequences are to be identified that are related and substantially identical to the probe, rather than identical, then it is useful to first establish the lowest temperature at which only homologous hybridization occurs with a particular concentration of salt (e.g., SSC or SSPE). Assuming that a 1% mismatch results in a 1° C. decrease in the $T_m$, the temperature of the final wash in the hybridization reaction is reduced accordingly (for example, if sequence having >95% identity with the probe are sought, the final wash temperature is decreased by 5° C.). In practice, the change in $T_m$ can be between 0.5° C. and 1.5° C. per 1% mismatch. Stringent conditions involve hybridizing at 68° C. in 5×SSC/5×Denhardt's solution/1.0% SDS, and washing in 0.2×SSC/0.1% SDS at room temperature. Moderately stringent conditions include washing in 3×SSC at 42° C. The parameters of salt concentration and temperature can be varied to achieve the optimal level of identity between the probe and the target nucleic acid. Additional guidance regarding such conditions is readily available in the art, for example, in Sambrook, et al., Molecular Cloning, A Laboratory Manual, Cold Spring Harbor Press, New York, N.Y. (1989); and Ausubel, et al., eds., Current Protocols in Molecular Biology, John Wiley & Sons, New York, N.Y., at Unit 2.10 (1995).

Synthetic analogs of nucleic acids may be preferred for use as probes because of superior stability under assay conditions. Modifications in the native structure, including alterations in the backbone, sugars or heterocyclic bases, have been shown to increase intracellular stability and binding affinity. Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-$CH_2$-5'-O-phosphonate and 3'-NH-5'-O-phosphoroamidate. Peptide nucleic acids replace the entire ribose phosphodiester backbone with a peptide linkage.

Sugar modifications are also used to enhance stability and affinity. The alpha-anomer of deoxyribose may be used, where the base is inverted with respect to the natural beta-anomer. The 2'-OH of the ribose sugar may be altered to form 2'-O-methyl or 2'-O-allyl sugars, which provides resistance to degradation without compromising affinity.

Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

In one aspect, disclosed herein are isolated nucleic acids comprising a sequence that hybridizes under stringent conditions to a nucleic acid comprising a nucleotide sequence encoding an amino acid sequence of a mutated $Na_v1.7$ sodium channel alpha-subunit but not to a nucleic acid sequence that encodes the amino acid sequence of the wild-type $Na_v1.7$ sodium channel alpha-subunit. For example, in one aspect, disclosed herein are isolated nucleic acids comprising a sequence that hybridizes under stringent conditions to a nucleic acid comprising a nucleotide sequence encoding the amino acid sequence of SEQ ID NO: 2 but not to the nucleic acid sequence that encodes SEQ ID NO: 38. In another aspect, disclosed herein are isolated nucleic acids comprising a sequence that hybridizes under stringent conditions to a nucleic acid comprising a nucleotide sequence encoding the amino acid sequence of SEQ ID NO: 3 but not to the nucleic acid sequence that encodes SEQ ID NO: 38. In yet another aspect, disclosed herein are isolated nucleic acids comprising a sequence that hybridizes under stringent conditions to a nucleic acid comprising a nucleotide sequence encoding the amino acid sequence of SEQ ID NO: 4 but not to the nucleic acid sequence that encodes SEQ ID NO: 38. In an further aspect, disclosed herein are isolated nucleic acids comprising a sequence that hybridizes under stringent conditions to a nucleic acid comprising a nucleotide sequence encoding the amino acid sequence of SEQ ID NO: 5 but not to the nucleic acid sequence that encodes SEQ ID NO: 38. In a still further aspect, disclosed herein are isolated nucleic acids comprising a sequence that hybridizes under stringent conditions to a nucleic acid comprising a nucleotide sequence encoding the amino acid sequence of SEQ ID NO: 6 but not to the nucleic acid sequence that encodes SEQ ID NO: 38. In one aspect, disclosed herein are isolated nucleic acids comprising a sequence that hybridizes under stringent conditions to a nucleic acid comprising a nucleotide sequence encoding the amino acid sequence of SEQ ID NO: 7 but not to the nucleic acid sequence that encodes SEQ ID NO: 38.

In another aspect, disclosed herein are isolated nucleic acids comprising a sequence that hybridizes under stringent conditions to a mutated $Na_v1.7$ nucleic acid sequence or a fragment thereof but not to a wild-type $Na_v1.7$ nucleic acid sequence. For example, in one aspect, disclosed herein are isolated nucleic acids comprising a sequence that hybridizes under stringent conditions to a nucleic acid sequence of SEQ ID NO: 8, or a fragment thereof, such as SEQ ID NO: 14, but not to the nucleic acid sequence of SEQ ID NO: 1. In another aspect, disclosed herein are isolated nucleic acids comprising a sequence that hybridizes under stringent conditions to a nucleic acid of SEQ ID NO: 9, or a fragment thereof, such as SEQ ID NO: 15, but not to the nucleic acid sequence of SEQ ID NO: 1. In yet another aspect, disclosed herein are isolated nucleic acids comprising a sequence that hybridizes under stringent conditions to a nucleic acid sequence of SEQ ID NO: 10, or a fragment thereof, such as SEQ ID NO: 16, but not to the nucleic acid sequence of SEQ ID NO: 1. In an further aspect, disclosed herein are isolated nucleic acids comprising a sequence that hybridizes under stringent conditions to a nucleic acid sequence of SEQ ID NO: 11, or a fragment thereof, such as SEQ ID NO: 17, but not to the nucleic acid sequence of SEQ ID NO: 1. In a still further aspect, disclosed herein are isolated nucleic acids comprising a sequence that hybridizes under stringent conditions to a nucleic acid sequence of SEQ ID NO: 12, or a fragment thereof, such as SEQ ID NO: 18, but not to the nucleic acid sequence of SEQ ID NO: 1. In one aspect, disclosed herein are isolated nucleic acids comprising a sequence that hybridizes under stringent conditions to a nucleic acid sequence of SEQ ID NO: 13, or a fragment thereof, such as SEQ ID NO: 19, but not to the nucleic acid sequence of SEQ ID NO: 1.

In yet another aspect, disclosed herein are isolated nucleic acids encoding mutant $Na_v1.7$ sodium channels comprising a sequence that hybridizes under stringent conditions to a mutated $Na_v1.7$ nucleic acid comprising a nucleotide sequence encoding an amino acid sequence of sodium channel alpha-subunit but not to a wild-type Na$_v$1.7 nucleic acid sequence. For example, in one aspect, disclosed herein are isolated nucleic acids comprising a sequence that hybridizes under stringent conditions to a nucleic acid comprising a nucleotide sequence encoding the amino acid sequence of SEQ ID NO: 2 but not to the nucleic acid sequence of SEQ ID NO: 1. In another aspect, disclosed herein are isolated nucleic acids comprising a sequence that hybridizes under stringent conditions to a nucleic acid comprising a nucleotide sequence encoding the amino acid sequence of SEQ ID NO: 3 but not to the nucleic acid sequence of SEQ ID NO: 1. In yet another aspect, disclosed herein are isolated nucleic acids comprising a sequence that hybridizes under stringent conditions to a nucleic acid comprising a nucleotide sequence encoding the amino acid sequence of SEQ ID NO: 4 but not to the nucleic acid sequence of SEQ ID NO: 1. In an further aspect, disclosed herein are isolated nucleic acids comprising a sequence that hybridizes under stringent conditions to a nucleic acid comprising a nucleotide sequence encoding the amino acid sequence of SEQ ID NO: 5 but not to the nucleic acid sequence of SEQ ID NO: 1. In a still further aspect, disclosed herein are isolated nucleic acids comprising a sequence that hybridizes under stringent conditions to a nucleic acid comprising a nucleotide sequence encoding the amino acid sequence of SEQ ID NO: 6 but not to the nucleic acid sequence of SEQ ID NO: 1. In one aspect, disclosed herein are isolated nucleic acids comprising a sequence that hybridizes under stringent conditions to a nucleic acid comprising a nucleotide sequence encoding the amino acid sequence of SEQ ID NO: 7 but not to the nucleic acid sequence of SEQ ID NO: 1.

In a further aspect, disclosed herein are isolated nucleic acids comprising a sequence that hybridizes under stringent conditions to a mutated Na$_v$1.7 nucleic acid sequence or a fragment thereof but not to the nucleic acid sequence that encodes SEQ ID NO: 38. For example, in one aspect, disclosed herein are isolated nucleic acids comprising a sequence that hybridizes under stringent conditions to a nucleic acid sequence of SEQ ID NO: 8, or a fragment thereof, such as SEQ ID NO: 14, but not to the nucleic acid sequence that encodes SEQ ID NO: 38. In another aspect, disclosed herein are isolated nucleic acids comprising a sequence that hybridizes under stringent conditions to a nucleic acid of SEQ ID NO: 9, or a fragment thereof, such as SEQ ID NO: 15, but not to the nucleic acid sequence that encodes SEQ ID NO: 38. In yet another aspect, disclosed herein are isolated nucleic acids comprising a sequence that hybridizes under stringent conditions to a nucleic acid sequence of SEQ ID NO: 10, or a fragment thereof, such as SEQ ID NO: 16, but not to the nucleic acid sequence that encodes SEQ ID NO: 38. In an further aspect, disclosed herein are isolated nucleic acids comprising a sequence that hybridizes under stringent conditions to a nucleic acid sequence of SEQ ID NO: 11, or a fragment thereof, such as SEQ ID NO: 17, but not to the nucleic acid sequence that encodes SEQ ID NO: 38. In a still further aspect, disclosed herein are isolated nucleic acids comprising a sequence that hybridizes under stringent conditions to a nucleic acid sequence of SEQ ID NO: 12, or a fragment thereof, such as SEQ ID NO: 18, but not to the nucleic acid sequence that encodes SEQ ID NO: 38. In one aspect, disclosed herein are isolated nucleic acids comprising a sequence that hybridizes under stringent conditions to a nucleic acid sequence of SEQ ID NO: 13, or a fragment thereof, such as SEQ ID NO: 19, but not to the nucleic acid sequence that encodes SEQ ID NO: 38.

Arrays

The disclosed materials, compounds, and methods also provide an array of oligonucleotides for identification of mutations, where discrete positions on the array are complementary to one or more of the provided mutated sequences, e.g. oligonucleotides of at least 12 nucleotides, frequently 15 nucleotides, 20 nucleotides, or larger, and including the sequence flanking the mutated position. Such an array may comprise a series of oligonucleotides, each of which can specifically hybridize to a different mutation of the disclosed compositions. An array may comprise all or a subset of nucleic acid sequences having SEQ ID NOs: 8, 9, 10, 11, 12, and/or 13, or any fragment of at least 15 contiguous nucleotides thereof, for example SEQ ID NOs: 14, 15, 16, 17, 18, and/or 19. Usually such an array will include at least 2 different mutated sequences, i.e., mutations located at unique positions within the locus, and may include all of the provided mutations. Therefore, the array can include wild-type sequences comprising the most commonly found alleles. The array can optionally comprise the most commonly found allele at a first, second, third, fourth, fifth, or more positions as well as other nucleotides at each of these positions. Each oligonucleotide sequence on the array will usually be at least about 12 nucleotides in length (i.e., 10-15 nucleotides), may be the length of the provided mutated sequences, or may extend into the flanking regions to generate fragments of 100 to 200 nucleotides in length. For examples of arrays, see Ramsay, (1998) Nat Biotech 16:4044; Hacia, et al. (1996) Nature Genetics 14:441-447; Lockhart, et al. (1996) Nature Biotechnol 14:1675-1680; and De Risi, et al. (1996) Nature Genetics 14:457-460, which are incorporated by reference in their entirety for the methods of making and using arrays.

Haplotyping

In another aspect, the disclosed materials, compositions, articles, devices, and methods relate to a method for determining a Na$_v$1.7 haplotype in a human subject, wherein the method comprises identifying one or more nucleotides encoding amino acid residues 62, 149, 641, 655, 739, 1123, or any combination thereof, wherein the nucleotide or nucleotides indicate the haplotype. The disclosed subject matter also provides a method for determining a Na$_v$1.7 haplotype in a human subject comprising identifying one or more nucleotides present at one or more of sites 184, 446, 1921, 1964, 2215, or 3369, in either or both copies of the Na$_v$1.7 gene contained in the subject genomic nucleic acid, wherein the nucleotide present at the mutated site or sites indicates the Na$_v$1.7 haplotype. It will be recognized by one of skill in the art that numerous haplotypes are possible.

For example, one of skill in the art could identify the nucleotide present in either or both copies of the Na$_v$1.7 gene contained in the subject genomic nucleic acid that encodes for amino acid 62 in the Na$_v$1.7 sodium channel alpha-subunit sequence. The haplotypes for this particular analysis can be I62V, P149Q, N641Y, K655R, I739V, L1123F, or any combination thereof, where the number indicates a position in the Na$_v$1.7 sodium channel alpha-subunit, the first letter represents the most common amino acid found at that positions, and the last letter represents the amino acid found in the haplotype. Similarly, one of skill in the art could identify the nucleotide in a Na$_v$1.7 nucleic acid sequence at position 184, 446, 1921, 1964, 2215, and/or 3369, and determine the Na$_v$1.7 haplotype. Therefore, any of positions 184, 446, 1921, 1964, 2215, and/or 3369 in the nucleic acid sequence or positions 62, 149, 641, 655, 739, and/or 1123 in the encoded amino acid sequence can be analyzed individually or in combination to obtain the haplotypes of the disclosed subject matter.

Determining a Predisposition

Disclosed herein is a method for determining a subject's predisposition to a neurologic disorder associated with a sodium channel mutation comprising comparing the subject's $Na_v1.7$ haplotype with one or more reference haplotypes that correlate with the neurologic disorder, a similar haplotype in the subject's $Na_v1.7$ haplotype as compared to the reference haplotype or haplotypes indicating a predisposition to the neurologic disorder.

As used herein, "neurologic disorder associated with a sodium channel mutation" includes, but is not limited to, seizure disorders (e.g., febrile seizures, nonfebrile seizures, and epileptic seizures). As used herein "epileptic seizures" includes, but is not limited to, partial (e.g., simple and complex) and generalized (e.g., absence, myoclonic, and tonic-clonic) seizures, temporal lobe epilepsy, and severe myoclonic epilepsy of infancy.

Each haplotype can be correlated with specific neurologic disorders or severity of such disorders to generate a database of reference haplotypes, such that one of skill in the art can compare a subject's haplotype to a reference haplotype or haplotypes and determine whether the subject is at risk for a neurologic disorder.

The reference haplotype can comprise nucleotides that encode one or more mutations in the $Na_v1.7$ sodium channel alpha-subunit. For example, the reference haplotype can comprise nucleotides that encode one or more mutations at residue 62, residue 149, residue 641, residue 655, residue 739, or residue 1123 of the encoded amino acid sequence of $Na_v1.7$.

Since subjects will vary depending on numerous parameters including, but not limited to, race, age, weight, medical history etc., as more information is gathered on populations, the database can contain haplotype information classified by race, age, weight, medical history etc., such that one of skill in the art can assess the subject's risk of developing neurologic disorders based on information more closely associated with the subject's demographic profile. Where there is a differential distribution of a mutation by racial background or another parameter, guidelines for drug administration can be generally tailored to a particular group.

It will be appreciated by those skilled in the art that the nucleic acids provided herein as well as the nucleic acid and amino acid sequences identified from subjects can be stored, recorded, and manipulated on any medium which can be read and accessed by a computer. As used herein, the words "recorded" and "stored" refer to a process for storing information on a computer medium. A skilled artisan can readily adopt any of the presently known methods for recording information on a computer readable medium to generate a list of sequences comprising one or more of the nucleic acids of the invention. Another aspect of the present invention is a computer readable medium having recorded thereon at least 2, 5, 10, 15, 20, 25, 30, 50, 100, 200, 250, 300, 400, 500, 1000, 2000, 3000, 4000 or 5000 nucleic acids of the invention or nucleic acid sequences identified from subjects.

Computer readable media include magnetically readable media, optically readable media, electronically readable media and magnetic/optical media. For example, the computer readable media may be a hard disc, a floppy disc, a magnetic tape, CD-ROM, DVD, RAM, or ROM as well as other types of other media known to those skilled in the art.

Embodiments of the present invention include systems, particularly computer systems which contain the sequence information described herein. As used herein, "a computer system" refers to the hardware components, software components, and data storage components used to store and/or analyze the nucleotide sequences of the present invention or other sequences. The computer system preferably includes the computer readable media described above, and a processor for accessing and manipulating the sequence data.

Preferably, the computer is a general purpose system that comprises a central processing unit (CPU), one or more data storage components for storing data, and one or more data retrieving devices for retrieving the data stored on the data storage components. A skilled artisan can readily appreciate that any one of the currently available computer systems are suitable.

In one particular aspect, the computer system includes a processor connected to a bus which is connected to a main memory, preferably implemented as RAM, and one or more data storage devices, such as a hard drive and/or other computer readable media having data recorded thereon. In some embodiments, the computer system further includes one or more data retrieving devices for reading the data stored on the data storage components. The data retrieving device may represent, for example, a floppy disk drive, a compact disk drive, a magnetic tape drive, a hard disk drive, a CD-ROM drive, a DVD drive, etc. In some embodiments, the data storage component is a removable computer-readable medium such as a floppy disk, a compact disk, a magnetic tape, etc. containing control logic and/or data recorded thereon. The computer system may advantageously include or be programmed by appropriate software for reading the control logic and/or the data from the data storage component once inserted in the data retrieving device. Software for accessing and processing the nucleotide sequences of the nucleic acids of the invention (such as search tools, compare tools, modeling tools, etc.) may reside in main memory during execution.

In some aspects, the computer system may further comprise a sequence comparer for comparing the nucleic acid sequences stored on a computer readable medium to another test sequence stored on a computer readable medium. A "sequence comparer" refers to one or more programs which are implemented on the computer system to compare a nucleotide sequence with other nucleotide sequences.

Accordingly, one aspect of the present invention is a computer system comprising a processor, a data storage device having stored thereon a nucleic acid of the invention, a data storage device having retrievably stored thereon reference nucleotide sequences to be compared with test or sample sequences and a sequence comparer for conducting the comparison. The sequence comparer may indicate a homology level between the sequences compared or identify a difference between the two sequences. For example, a reference sequence comprising SEQ ID NO: 8 or any fragment thereof, such as SEQ ID NO: 14, can be compared with a test sequence from a subject to determine if the test sequence is the same as the reference sequence, e.g., contains an A at position 184 or a different nucleotide (G).

Alternatively, the computer program may be a computer program which compares a test nucleotide sequence(s) from a subject or a plurality of subjects to a reference nucleotide sequence(s) in order to determine whether the test nucleotide sequence(s) differs from or is the same as a reference nucleic acid sequence(s) at one or more positions. Optionally such a program records the length and identity of inserted, deleted or substituted nucleotides with respect to the sequence of either the reference polynucleotide or the test nucleotide sequence. In one embodiment, the computer program may be a program which determines whether the nucleotide sequences of the test nucleotide sequence contains one or more single nucleotide mutations with respect to a reference nucleotide sequence. These single nucleotide mutations may each comprise a single base substitution, insertion, or deletion.

Accordingly, another aspect of the materials, compounds, articles, devices, and methods disclosed herein is a method for determining whether a test nucleotide sequence differs at one or more nucleotides from a reference nucleotide sequence comprising the steps of reading the test nucleotide sequence and the reference nucleotide sequence through use of a computer program which identifies differences between nucleic acid sequences and identifying differences between the test nucleotide sequence and the reference nucleotide sequence with the computer program. The computer program can be a program which identifies single nucleotide polymorphisms. The method may be implemented by the computer systems described above. The method may also be performed by reading at least 2, 5, 10, 15, 20, 25, 30, 50, 100, or more test nucleotide sequences and the reference nucleotide sequences through the use of the computer program and identifying differences between the test nucleotide sequences and the reference nucleotide sequences with the computer program. A computer program that identifies single nucleotide mutations in a $Na_v1.7$ gene sequence and determines a subject's haplotype is also contemplated by the subject matter disclosed herein. The subject matter disclosed herein also provides for a computer program that correlates haplotypes with $Na_v1.7$ levels such that one of skill in the art can assess a subject's risk of developing a neurologic disorder, such as febrile seizures, nonfebrile seizures, or epileptic seizures. The computer program can optionally include treatment options or drug indications for subjects with haplotypes associated with increased risk of seizures.

The nucleic acids of the invention (both test nucleic acid sequences and reference nucleic acid sequences) may be stored and manipulated in a variety of data processor programs in a variety of formats. For example, they may be stored as text in a word processing file, such as Microsoft-WORD or WORDPERFECT or as an ASCII file in a variety of database programs familiar to those of skill in the art, such as DB2, SYBASE, or ORACLE. In addition, many computer programs and databases may be used as sequence comparers, identifiers, or sources of reference nucleotide sequences. The following list is intended not to limit the invention but to provide guidance to programs and databases which are useful with the nucleic acid sequences of the invention. The programs and databases which may be used include, but are not limited to: MacPattern (MBL), DiscoveryBase (Molecular Applications Group), GeneMine (Molecular Applications Group), Look (Molecular Applications Group), MacLook (Molecular Applications Group), BLAST and BLAST2 (NCBI), BLASTN and BLASTX (Altschul, et al. (1990) J Mol Biol 3:403-410), FASTA (Pearson and Lipman, (1988) Proc Natl Acad Sci USA 85:2444-2448), FASTDB (Brutlag et al., (1990) Compt Appl Biosci 6:237-245), Catalyst (Molecular Simulations Inc.), Catalyst/SHAPE (Molecular Simulations Inc.), Cerius.sup.2.DBAccess (Molecular Simulations Inc.), HypoGen (Molecular Simulations Inc.), Insight II (Molecular Simulations Inc.), Discover (Molecular Simulations Inc.), CHARMm (Molecular Simulations Inc.), Felix (Molecular Simulations Inc.), DelPhi, (Molecular Simulations Inc.), QuanteMM, (Molecular Simulations Inc.), Homology (Molecular Simulations Inc.), Modeler (Molecular Simulations Inc.), ISIS (Molecular Simulations Inc.), Quanta/Protein Design (Molecular Simulations Inc.), WebLab (Molecular Simulations Inc.), WebLab Diversity Explorer (Molecular Simulations Inc.), Gene Explorer (Molecular Simulations Inc.), SeqFold (Molecular Simulations Inc.), the EMBL/Swissprotein database, the MDL Available Chemicals Directory database, the MDL Drug Data Report data base, the Comprehensive Medicinal Chemistry database, Derwents's World Drug Index database, the BioByteMasterFile database, the Genbank database, and the Genseqn database. Many other programs and data bases would be apparent.

Delivery of the $Na_v1.7$ Nucleic Acid Sequence

Optionally, the nucleic acids described herein are delivered to various expression systems. There are a number of compositions and methods which can be used to deliver nucleic acids to cells, either in vitro or in vivo. These methods and compositions can largely be broken down into two classes: viral based delivery systems and non-viral based delivery systems. For example, the nucleic acids can be delivered through a number of direct delivery systems such as, electroporation, lipofection, calcium phosphate precipitation, plasmids, viral vectors, viral nucleic acids, phage nucleic acids, phages, cosmids, or via transfer of genetic material in cells or carriers such as cationic liposomes. Appropriate means for transfection, including viral vectors, chemical transfectants, or physico-mechanical methods such as electroporation and direct diffusion of DNA, are described by, for example, Wolff, et al. (1990) Science 247:1465-1468; and Wolff, (1991) Nature 352:815-818. Such methods are well known in the art and readily adaptable for use with the compositions and methods described herein. In certain cases, the methods will be modified to specifically function with large DNA molecules.

Nucleic Acid Based Delivery Systems: Vectors

In one aspect, disclosed herein are expression vectors comprising a nucleic acid comprising a nucleotide sequence encoding an amino acid sequence of mutated $Na_v1.7$ sodium channel alpha-subunit wherein the nucleotide sequence is operably linked to an expression control sequence. For example, in one aspect, disclosed herein are expression vectors comprising a nucleic acid comprising a nucleotide sequence encoding the amino acid sequence of SEQ ID NO: 2 operably linked to an expression control sequence. In another aspect, disclosed herein are expression vectors comprising a nucleic acid comprising a nucleotide sequence encoding the amino acid sequence of SEQ ID NO: 3 operably linked to an expression control sequence. In yet another aspect, disclosed herein are expression vectors comprising a nucleic acid comprising a nucleotide sequence encoding the amino acid sequence of SEQ ID NO: 4 operably linked to an expression control sequence. In a further aspect, disclosed herein are expression vectors comprising a nucleic acid comprising a nucleotide sequence encoding the amino acid sequence of SEQ ID NO: 5 operably linked to an expression control sequence. In a still further aspect, disclosed herein are expression vectors comprising a nucleic acid comprising a nucleotide sequence encoding the amino acid sequence of SEQ ID NO: 6 operably linked to an expression control sequence. In one aspect, disclosed herein are expression vectors comprising a nucleic acid comprising a nucleotide sequence encoding the amino acid sequence of SEQ ID NO: 7 operably linked to an expression control sequence.

Further provided are expression vectors comprising any fragment of the nucleic acid encoding SEQ ID NOs: 2-7. Such fragments preferably encode at least 5 contiguous amino acid sequences of SEQ ID NOs: 2-7.

Expression or transfer vectors can be any nucleotide construction used to deliver genes into cells (e.g., a plasmid), or as part of a general strategy to deliver genes, e.g., as part of recombinant retrovirus or adenovirus (Ram, et al. (1993) Cancer Res 53:83-88).

As used herein, plasmid or viral vectors are agents that transport the disclosed nucleic acids, such as SEQ ID NOs: 8, 9, 10, 11, 12, and/or 13 into the cell without degradation and include a promoter yielding expression of the gene in the cells into which it is delivered. Viral vectors are, for example, Adenovirus, Adeno-associated virus, Herpes virus, Vaccinia virus, Polio virus, AIDS virus, neuronal trophic virus, Sindbis and other RNA viruses, including those viruses with the HIV backbone. Also preferred are any viral families which share the properties of these viruses which make them suitable for use as vectors. Retroviruses include Murine Maloney Leukemia virus, MMLV, and retroviruses that express the desirable properties of MMLV as a vector. Retroviral vectors are able to carry a larger genetic payload, i.e., a transgene or marker gene, than other viral vectors, and for this reason are a commonly used vector. However, they are not as useful in non-proliferating cells. Adenovius vectors are relatively stable and easy to work with, have high titers, and can be delivered in aerosol formulation, and can transfect non-dividing cells. Pox viral vectors are large and have several sites for inserting genes, they are thermostable and can be stored at room temperature. In one specific aspect is a viral vector that has been engineered so as to suppress the immune response of the host organism, elicited by the viral antigens. Vectors of this type will carry coding regions for Interleukin 8 or 10.

Viral vectors can have higher transaction (ability to introduce genes) abilities than chemical or physical methods to introduce genes into cells. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promotor cassette is inserted into the viral genome in place of the removed viral DNA. Constructs of this type can carry up to about 8 kb of foreign genetic material. The necessary functions of the removed early genes are typically supplied by cell lines which have been engineered to express the gene products of the early genes in trans.

Retroviral Vectors

A retrovirus is an animal virus belonging to the virus family of Retroviridae, including any types, subfamilies, genus, or tropisms. Retroviral vectors, in general, are described by Verma, Retroviral vectors for gene transfer. In Microbiology—1985, American Society for Microbiology, pp. 229-232, Washington, (1985), which is incorporated by reference herein in its entirety for retroviral vectors and methods of making them. Examples of methods for using retroviral vectors for gene therapy are described in U.S. Pat. Nos. 4,868,116 and 4,980,286; PCT applications WO 90/02806 and WO 89/07136; and Mulligan, (Science 260:926-932 (1993)); the teachings of which are incorporated by reference herein in its entirety for retroviral vectors and methods of using them.

A retrovirus is essentially a package which has packed into it nucleic acid cargo. The nucleic acid cargo carries with it a packaging signal, which ensures that the replicated daughter molecules will be efficiently packaged within the package coat. In addition to the package signal, there are a number of molecules which are needed in cis, for the replication, and packaging of the replicated virus. Typically a retroviral genome, contains the gag, pol, and env genes which are involved in the making of the protein coat. It is the gag, pol, and env genes which are typically replaced by the foreign DNA that it is to be transferred to the target cell. Retrovirus vectors typically contain a packaging signal for incorporation into the package coat, a sequence which signals the start of the gag transcription unit, elements necessary for reverse transcription, including a primer binding site to bind the tRNA primer of reverse transcription, terminal repeat sequences that guide the switch of RNA strands during DNA synthesis, a purine rich sequence 5' to the 3' LTR that serve as the priming site for the synthesis of the second strand of DNA synthesis, and specific sequences near the ends of the LTRs that enable the insertion of the DNA state of the retrovirus to insert into the host genome. The removal of the gag, pol, and env genes allows for about 8 kb of foreign sequence to be inserted into the viral genome, become reverse transcribed, and upon replication be packaged into a new retroviral particle. This amount of nucleic acid is sufficient for the delivery of a one to many genes depending on the size of each transcript. It is preferable to include either positive or negative selectable markers along with other genes in the insert.

Since the replication machinery and packaging proteins in most retroviral vectors have been removed (gag, pol, and env), the vectors are typically generated by placing them into a packaging cell line. A packaging cell line is a cell line which has been transfected or transformed with a retrovirus that contains the replication and packaging machinery, but lacks any packaging signal. When the vector carrying the DNA of choice is transfected into these cell lines, the vector containing the gene of interest is replicated and packaged into new retroviral particles, by the machinery provided in cis by the helper cell. The genomes for the machinery are not packaged because they lack the necessary signals.

Adenoviral Vectors

The construction of replication-defective adenoviruses has been described (Berkner, et al. (1987) J Virology 61:1213-1220; Massie, et al. (1986) Mol Cell Biol 6:2872-2883; Haj-Ahmad, et al. (1986) J Virology 57:267-274; Davidson, et al. (1987) J Virology 61:1226-1239; Zhang, (1993) BioTechniques 15:868-872). The benefit of the use of these viruses as vectors is that they are limited in the extent to which they can spread to other cell types, since they can replicate within an initial infected cell, but are unable to form new infectious viral particles. Recombinant adenoviruses have been shown to achieve high efficiency gene transfer after direct, in vivo delivery to airway epithelium, hepatocytes, vascular endothelium, CNS parenchyma and a number of other tissue sites (Morsy, (1993) J Clin Invest 92:1580-1586; Kirshenbaum, (1993) J Clin Invest 92:381-387; Roessler, (1993) J Clin Invest 92:1085-1092; Moullier, (1993) Nature Genetics 4:154-159; La Salle, (1993) Science 259:988-990; Gomez-Foix, (1992) J Biol Chem 267:25129-25134; Rich, (1993) Human Gene Therapy 4:461-476; Zabner, (1994) Nature Genetics 6:75-83; Guzman, (1993) Circulation Res 73:1201-1207; Bout, (1994) Human Gene Therapy 5:3-10; Zabner, (1993) Cell 75:207-216; Caillaud, (1993) Eur. J. Neuroscience 5:1287-1291; Ragot, (1993) J Gen Virology 74:501-507). Recombinant adenoviruses achieve gene transduction by binding to specific cell surface receptors, after which the virus is internalized by receptor-mediated endocytosis, in the same manner as wild type or replication-defective adenovirus (Chardonnet, et al. (1970) Virology 40:462-477; Brown, et al. (1973) J Virology 12:386-396; Svensson, et al. (1985) J Virology 55:442-449; Seth, et al. (1985) J Virol 51:650-655; Seth, et al. (1984) Mol Cell Biol 4:1528-1533; Varga, et al. (1991) J Virology 65:6061-6070; Wickham, et al. (1993) Cell 73:309-319).

A viral vector can be one based on an adenovirus which has had the E1 gene removed and these virons are generated in a cell line such as the human 293 cell line. In another aspect, both the E1 and E3 genes are removed from the adenovirus genome.

Adeno-Associated Viral Vectors

Another type of viral vector is based on an adeno-associated virus (AAV). This defective parvovirus is a preferred vector because it can infect many cell types and is nonpathogenic to humans. AAV type vectors can transport about 4 to 5 kb and wild type AAV is known to stably insert into chromosome 19. Vectors which contain this site specific integration property are preferred. An especially preferred embodiment of this type of vector is the P4.1 C vector produced by Avigen, San Francisco, Calif., which can contain the herpes simplex virus thymidine kinase gene, HSV-tk, and/or a marker gene, such as the gene encoding the green fluorescent protein, GFP.

In another type of AAV virus, the AAV contains a pair of inverted terminal repeats (ITRs) which flank at least one cassette containing a promoter which directs cell-specific expression operably linked to a heterologous gene. Heterologous in this context refers to any nucleotide sequence or gene which is not native to the AAV or B19 parvovirus.

Typically the AAV and B19 coding regions have been deleted, resulting in a safe, noncytotoxic vector. The AAV ITRs, or modifications thereof, confer infectivity and site-specific integration, but not cytotoxicity, and the promoter directs cell-specific expression. U.S. Pat. No. 6,261,834 is incorporated by reference herein in its entirety for material related to the AAV vector.

The disclosed vectors described throughout thus provide nucleic acids which are capable of integration into a mammalian chromosome without substantial toxicity. The vectors can also provide nucleic acids that can be expressed in oocytes (including, e.g., Kenopus oocytes).

The inserted genes in viral and retroviral usually contain promoters, and/or enhancers to help control the expression of the desired gene product. A promoter is generally a sequence or sequences of nucleic acids that function when in a relatively fixed location in regard to the transcription start site. A promoter contains core elements required for basic interaction of RNA polymerase and transcription factors, and may contain upstream elements and response elements.

Large Payload Viral Vectors

Molecular genetic experiments with large human herpesviruses have provided a means whereby large heterologous DNA fragments can be cloned, propagated and established in cells permissive for infection with herpesviruses (Sun, et al. (1994) Nature Genetics 8:33-41; Cotter, et al. (1999) Curr Opin Mol Ther 5:633-644). These large DNA viruses (herpes simplex virus (HSV) and Epstein-Barr virus (EBV), have the potential to deliver fragments of human heterologous DNA>150 kb to specific cells. EBV recombinants can maintain large pieces of DNA in the infected B-cells as episomal DNA. Individual clones carried human genomic inserts up to 330 kb appeared genetically stable. The maintenance of these episomes requires a specific EBV nuclear protein, EBNA1, constitutively expressed during infection with EBV. Additionally, these vectors can be used for transfection, where large amounts of protein can be generated transiently in vitro. Herpesvirus amplicon systems are also being used to package pieces of DNA>220 kb and to infect cells that can stably maintain DNA as episomes.

Other useful systems include, for example, replicating and host-restricted non-replicating vaccinia virus vectors.

Non-Nucleic Acid Based Systems

The disclosed compositions can also be delivered to the target cells in a variety of ways other than through nucleic acid based methods. For example, the compositions can be delivered through electroporation, or through lipofection, or through calcium phosphate precipitation. The delivery mechanism chosen will depend in part on the type of cell targeted and whether the delivery is occurring for example in vivo or in vitro.

Thus, the compositions can comprise, in addition to the disclosed mutant $Na_v1.7$ nucleic acid sequences or vectors, for example, lipids such as liposomes, such as cationic liposomes (e.g., DOTMA, DOPE, DC cholesterol) or anionic liposomes. Liposomes can further comprise proteins to facilitate targeting a particular cell, if desired. Administration of a composition comprising a compound and a cationic liposome can be administered to the blood afferent to a target organ or inhaled into the respiratory tract to target cells of the respiratory tract. Regarding liposomes, see, e.g., Brigham, et al. (1989) Am J Resp Cell Mol Biol 1:95-100; Felgner, et al. (1987) Proc Natl Acad Sci USA 84:7413-7417; U.S. Pat. No. 4,897,355. Furthermore, the compound can be administered as a component of a microcapsule that can be targeted to specific cell types, such as macrophages, or where the diffusion of the compound or delivery of the compound from the microcapsule is designed for a specific rate or dosage.

In the methods described above which include the administration and uptake of exogenous DNA into the cells of a subject (i.e., gene transduction or transfection), delivery of the compositions to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the disclosed nucleic acid or vector can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al. (1991) Bioconjugate Chem. 2:447-451; Bagshawe, et al. (1998) Br J Cancer 60:275-281; Bagshawe, et al. (1988) Br J Cancer 58:700-703; Senter, et al. (1993) Bioconjugate Chem 4:3-9; Battelli, et al. (1992) Cancer Immunol Immunother 35:421-425; Pietersz, et al. (1992) Immunolog Rev 129:57-80; Roffler, et al. (1991) Biochem Pharmacol 42:2062-2065). These techniques can be used for a variety of other specific cell types. Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes, et al. (1989) Cancer Res 49:6214-6220; Litzinger, et al. (1992) Biochimica et Biophysica Acta 1104:179-187). In general, receptors are involved in pathways of endocytosis, either constitutive or ligand induced. These receptors cluster in clathrin coated pits, enter the cell via clathrin coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor level regulation. Many receptors follow more than one intracellular pathway, depending on the cell type, receptor concentration, type of ligand, ligand valency, and ligand concentration. Molecular and cellular mechanisms of receptor mediated endocytosis has been reviewed (see Brown, et al. (1991) DNA and Cell Biology 10:399-409).

Nucleic acids that are delivered to cells which are to be integrated into the host cell genome, typically contain integration sequences. These sequences are often viral related sequences, particularly when viral based systems are used. These viral integration systems can also be incorporated into nucleic acids which are to be delivered using a non-nucleic acid based system of deliver, such as a liposome, so that the nucleic acid contained in the delivery system can be come integrated into the host genome.

Other general techniques for integration into the host genome include, for example, systems designed to promote homologous recombination with the host genome. These systems typically rely on sequence flanking the nucleic acid to be expressed that has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those of skill in the art.

Expression

The nucleic acids that are delivered to cells typically contain expression controlling systems. For example, the inserted genes in viral and retroviral systems usually contain expression control sequences, i.e., promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

Viral Promoters and Enhancers

Preferred promoters controlling transcription from vectors in mammalian host cells may be obtained from various sources, for example, the genomes of viruses such as: polyoma, Simian Virus 40 (SV40), adenovirus, retroviruses, hepatitis B virus and most preferably cytomegalovirus, or from heterologous mammalian promoters, e.g., beta-actin promoter. The early and late promoters of the SV40 virus are conveniently obtained as an SV40 restriction fragment which also contains the SV40 viral origin of replication (Fiers, et al. (1978) Nature 273: 113). The immediate early promoter of the human cytomegalovirus is conveniently obtained as a HindIII E restriction fragment (see Greenway, et al. (1982) Gene 18:355-360). Of course, promoters from the host cell or related species also are useful herein.

Enhancer generally refers to a sequence of DNA that functions at no fixed distance from the transcription start site and can be either 5' (Laimins, et al. (1981) Proc Natl Acad Sci USA 78:993) or 3' (Lusky, et al. (1983) Mol Cell Bio 3:1108) to the transcription unit. Furthermore, enhancers can be within an intron (Banerji, et al. (1983) Cell 33:729) as well as within the coding sequence itself (Osborne, et al. (1984) Mol Cell Bio 4:1293). They are usually between 10 and 300 bp in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (e.g., globin, elastase, albumin, fetoprotein, and insulin), typically, one will use an enhancer from a eukaryotic cell virus for general expression. Preferred examples are the SV40 enhancer on the late side of the replication origin (bp 100-270), the cytomegalovirus early promoter enhancer, the polyoma enhancer on the late side of the replication origin, and adenovirus enhancers.

The promotor and/or enhancer may be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

In certain embodiments, the promoter and/or enhancer region can act as a constitutive promoter and/or enhancer to maximize expression of the region of the transcription unit to be transcribed. In certain constructs the promoter and/or enhancer region be active in all eukaryotic cell types, even if it is only expressed in a particular type of cell at a particular time. A preferred promoter of this type is the CMV promoter (650 bases). Other preferred promoters are SV40 promoters, cytomegalovirus (full-length promoter), and retroviral vector LTF.

It has been shown that all specific regulatory elements can be cloned and used to construct expression vectors that are selectively expressed in specific cell types such as melanoma cells. For example, the glial fibrillary acetic protein (GFAP) promoter has been used to selectively express genes in cells of glial origin.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3'-untranslated regions also include transcription termination sites. It is preferred that the transcription unit also contains a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In certain transcription units, the polyadenylation region is derived from the SV40 early polyadenylation signal and consists of about 400 bases. It is also preferred that the transcribed units contain other standard sequences alone or in combination with the above sequences improve expression from, or stability of, the construct.

Markers

The viral vectors can include nucleic acid sequence encoding a marker product. This marker product is used to determine if the gene has been delivered to the cell and once delivered is being expressed. Preferred marker genes are the E. Coli lacZ gene, which encodes beta-galactosidase, and green fluorescent protein (GFP).

Marker product, as used herein, is synonymous with "reporter protein." As used herein, a "reporter protein" is any protein that can be specifically detected when expressed. Reporter proteins are useful for detecting or quantifying expression from expression sequences. Many reporter proteins are known to one of skill in the art. These include, but are not limited to, beta-galactosidase, luciferase, and alkaline phosphatase that produce specific detectable products. Fluorescent reporter proteins can also be used, such as green fluorescent protein (GFP), green reef coral fluorescent protein (G-RCFP), cyan fluorescent protein (CFP), red fluorescent protein (RFP) and yellow fluorescent protein (YFP).

In some embodiments the marker or reporter protein may be a selectable marker. Examples of suitable selectable markers for mammalian cells are dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are: CHO DHFR cells and mouse LTK cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, (Southern, et al. (1982) J Molec Appl Genet. 1:327), mycophenolic acid, (Mulligan, et al. (1980) Science 209:1422) or hygromycin, (Sugden, et al. (1985) Mol Cell Biol 5:410-413). The three examples employ bacterial genes under eukaryotic control to convey resistance to the appropriate drug G418 or neomycin (geneticin), xgpt (mycophenolic acid) or hygromycin, respectively. Others include the neomycin analog G418 and puramycin.

Cultured Cells

The materials, compositions, articles, devices, and methods disclosed herein, in one aspect, related to a method of making a mutant Nav1.7 sodium channel alpha subunit comprising culturing the cells comprising vectors comprising mutant $Na_v1.7$ nucleic acids under conditions allowing expression of the polypeptide encoded by the nucleic acid, wherein the polypeptide comprises a mutant $Na_v1.7$ sodium channel.

Transgenic Animals

In one aspect, disclosed herein are transgenic animals that express one or more of the mutant $Na_v1.7$ sodium channels described herein. For example, disclosed herein is a transgenic mouse comprising cells that encode a mutant $Na_v1.7$ sodium channel alpha-subunit, wherein the mouse exhibits increased seizure activity as compared to the wild-type animal.

"Transgenic animal" is used herein to mean an animal comprising a transgene. By a "transgene" is meant a nucleic acid sequence that is inserted by artifice into a cell and becomes a part of the genome of that cell and its progeny. Such a transgene may be (but is not necessarily) partly or entirely heterologous (for example, derived from a different species) to the cell. A transgenic animal can be any non-human animal, such as a mouse, rat, guinea pig, sheep, pig, goat, and the like. Transgenic animals are made by techniques that are well known in the art. For example, a transgenic animal can be prepared by the method used in U.S. Pat. No. 4,736,866

Mutant $Na_v1.7$ Sodium Channel Alpha-Subunits

In one aspect, disclosed herein are mutant $Na_v1.7$ sodium channel alpha-subunits and the use of such mutant $Na_v1.7$ sodium channels to diagnose and treat disease states such as, for example, neurologic disorders associated with a sodium channel mutation. It was found that specific sites in the $Na_v1.7$ sodium channel alpha-subunit are mutated, i.e., the amino acid at a specific position or at specific positions differs from that observed in the most commonly found $Na_v1.7$ sodium channel.

As this specification discusses various amino acid sequences it is understood that the nucleic acids that can encode those amino acid sequences are also disclosed. This would include all degenerate sequences related to a specific amino acid sequence, i.e. all nucleic acids having a sequence that encodes one particular amino acid sequence as well as all nucleic acids, including degenerate nucleic acids, encoding the disclosed variants and derivatives of the amino acid sequences. Thus, while each particular nucleic acid sequence may not be written out herein, it is understood that each and every sequence is in fact disclosed and described herein through the disclosed amino acid sequence. For example, one of the many nucleic acid sequences that can encode the amino acid sequence of SEQ ID NO: 2 is set forth in SEQ ID NO: 8. Another nucleic acid sequence that encodes the amino acid sequence of SEQ ID NO: 3 is set forth in SEQ ID NO: 9. Another nucleic acid sequence that encodes the amino acid sequence of SEQ ID NO: 4 is set forth in SEQ ID NO: 10. Another nucleic acid sequence that encodes the amino acid sequence of SEQ ID NO: 5 is set forth in SEQ ID NO: 11. Another nucleic acid sequence that encodes the amino acid sequence of SEQ ID NO: 6 is set forth in SEQ ID NO: 12. Another nucleic acid sequence that encodes the amino acid sequence of SEQ ID NO: 7 is set forth in SEQ ID NO: 13. It is also understood that while no amino acid sequence indicates what particular DNA sequence encodes that protein within an organism, where particular variants of a disclosed protein are disclosed herein, the known nucleic acid sequence that encodes that amino acid sequence in the particular mutant $Na_v1.7$ sodium channel alpha-subunit from which that amino acid sequence arises is also known and herein disclosed and described.

In one aspect, the mutant $Na_v1.7$ sodium channel alpha-subunits described herein have one or more mutated sites. For example, in one aspect, disclosed herein is a mutant $Na_v1.7$ sodium channel alpha-subunit where the amino acid at position 62 is not isoleucine (I) as is commonly found at position 62 but, rather, valine (V) (SEQ ID NO: 2). In another aspect, disclosed herein is a mutant $Na_v1.7$ sodium channel alpha-subunit where the amino acid at position 149 is not proline (P) as is commonly found at position 149 but, rather, glutamine (Q) (SEQ ID NO: 3). In another aspect, disclosed herein is a mutant $Na_v1.7$ sodium channel alpha-subunit where the amino acid at position 641 is not asparagines (N) as is commonly found at position 641 but, rather, tyrosine (Y) (SEQ ID NO: 4). In yet another aspect, disclosed herein is a mutant $Na_v1.7$ sodium channel alpha-subunit where the amino acid at position 655 is not lysine (K) as is commonly found at position 655 but, rather, arginine (R) (SEQ ID NO: 5). In a further aspect, disclosed herein is a mutant $Na_v1.7$ sodium channel alpha-subunit where the amino acid at position 739 is not isoleucine (I) as is commonly found at position 739 but, rather, valine (V) (SEQ ID NO: 6). In a still further aspect, disclosed herein is a mutant $Na_v1.7$ sodium channel alpha-subunit where the amino acid at position 1123 is not leucine (L) as is commonly found at position 1123 but, rather, phenylalanine (F) (SEQ ID NO: 7).

Also contemplated are variants and derivatives of the disclosed mutant $Na_v1.7$ amino acid sequences. It is understood that one way to define the variants and derivatives of the disclosed proteins herein is through defining the variants and derivatives in terms of homology/identity to specific known sequences. For example, SEQ ID NO: 2 sets forth a particular sequence of a mutant I62V mutant sodium channel alpha-subunit, SEQ ID NO: 3 sets forth a particular sequence of a mutant P149Q $Na_v1.7$ sodium channel alpha-subunit, SEQ ID NO: 4 sets forth a particular sequence of a mutant N641Y $Na_v1.7$ sodium channel alpha-subunit, SEQ ID NO: 5 sets forth a particular sequence of a mutant K655R $Na_v1.7$ sodium channel alpha-subunit, SEQ ID NO: 6 sets forth a particular sequence of a mutant I739V $Na_v1.7$ sodium channel alpha-subunit, and SEQ ID NO: 7 sets forth a particular sequence of a mutant L1123F $Na_v1.7$ sodium channel alpha-subunit. Specifically disclosed are variants of these and other proteins herein disclosed which have at least, 70% or 75% or 80% or 85% or 90% or 95% homology to the stated sequence. Also, provided are amino acid sequences comprising the sequences of SEQ ID NOs: 2, 3, 4, 5, 6, and 7, or any fragment thereof wherein the sequence comprises one or more conservative amino acid substitutions. Preferably, the amino acid sequence with conservative amino acid substitutions maintains sodium channel function. Examples of conservative amino acid substitutions are shown in Table 1. Those of skill in the art readily understand how to determine the homology of two proteins. For example, the homology can be calculated after aligning the two sequences so that the homology is at its highest level.

TABLE 1

Amino Acid Substitutions
Original Residue Exemplary Conservative Substitutions,
others are known in the art.

| |
|---|
| Ala ↔ ser |
| Arg ↔ lys or gln |
| Asn ↔ gln or his |
| Asp ↔ glu |
| Cys ↔ ser |
| Gln ↔ asn or lys |
| Glu ↔ asp |
| Gly ↔ pro |
| His ↔ asn or gln |
| Ile ↔ leu or val |
| Leu ↔ ile or val |
| Lys ↔ arg or gln; |
| Met ↔ leu or ile |
| Phemet ↔ leu or tyr |
| Ser ↔ thr |
| Thr ↔ ser |
| Trp ↔ tyr |
| Tyr ↔ trp or phe |
| Val ↔ ile or leu |

Another way of calculating homology can be performed by published algorithms. Optimal alignment of sequences for comparison may be conducted by the local homology algorithm of Smith and Waterman (1981) Adv Appl Math 2:482, by the homology alignment algorithm of Needleman and Wunsch (1970) J Mol Biol 48:443, by the search for similarity method of Pearson and Lipman, (1988) Proc Natl Acad Sci USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by inspection.

Also, disclosed herein are isolated polypeptides and fragments of polypeptides comprising mutant $Na_v1.7$ sodium channel alpha-subunit amino acid sequences. For example, disclosed herein are isolated polypeptides having amino acid sequences of SEQ ID NOs: 2, 3, 4, 5, 6, and 7. In another aspect, disclosed herein are fragments of such sequences. For example, disclosed herein are isolated polypeptides having amino acid sequences of SEQ ID NOs: 32, 33, 34, 35, 36, and 37.

Also, provided are fragments of at least 5 contiguous amino acid sequences corresponding to SEQ ID NOs: 2, 3, 4, 5, 6, and 7. Among these fragments are those comprising PFVYG (SEQ ID NO: 32), NPQDW (SEQ ID NO: 33), LPYGG (SEQ ID NO: 34), IHRKR (SEQ ID NO: 35), LAVTI (SEQ ID NO: 36), and NPFPG (SEQ ID NO: 37).

Methods of Synthesizing Polypeptides

The peptides, polypeptides, and polypeptide fragments disclosed herein can be chemically synthesized using currently available laboratory equipment using either Fmoc (9-fluorenylmethyloxycarbonyl) or Boc (tert-butyloxycarbonyl) chemistry. (Applied Biosystems, Inc., Foster City, Calif.). One skilled in the art can readily appreciate that a peptide or polypeptide corresponding to the sodium channels disclosed herein, for example, can be synthesized by standard chemical reactions. For example, a peptide or polypeptide fragment can be synthesized and not cleaved from its synthesis resin whereas another peptide or polypeptide fragment can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an sodium channel, or fragment thereof. (See Grant G A (1992) Synthetic Peptides: A User Guide. W.H. Freeman and Co., New York, N.Y. (1992); Bodansky M and Trost B., Ed. Principles of Peptide Synthesis. Springer-Verlag Inc., New York, N.Y. (1993)). Alternatively, the peptide or polypeptide is independently synthesized in vivo as described above.

For example, enzymatic ligation of cloned or synthetic peptide segments allow relatively short peptide fragments to be joined to produce larger peptide fragments, polypeptides or whole protein domains (Abrahmsen, et al. (1991) Biochemistry 30:4151). Alternatively, native chemical ligation of synthetic peptides can be utilized to synthetically construct large peptides or polypeptides from shorter peptide fragments. This method consists of a two step chemical reaction (Dawson, et al. (1994) Science 266:776-779). The first step is the chemoselective reaction of an unprotected synthetic peptide-alpha-thioester with another unprotected. peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site. Application of this native chemical ligation method to the total synthesis of a protein molecule is illustrated by the preparation of human interleukin 8 (IL-8) (Baggiolini, et al. (1992) FEBS Lett. 307:97-101; Clark-Lewis, et al. (1994) J Biol Chem 269:16075; Clark-Lewis, et al. (1991) Biochemistry 30:3128; Rajarathnam, et al. (1994) Biochemistry 33:6623-30).

Alternatively, unprotected peptide segments are chemically linked where the bond formed between the peptide segments as a result of the chemical ligation is an unnatural (non-peptide) bond (Schnolzer, et al. (1992) Science, 256:221). This technique has been used to synthesize analogs of protein domains as well as large amounts of relatively pure proteins with full biological activity (deLisle Milton, et al. Techniques in Protein Chemistry IV. Academic Press, New York, pp. 257-267 (1992)).

Antibodies to Mutant $Na_v1.7$ Sodium Channels

The disclosed materials, compositions, articles, devices, and methods disclosed herein, in one aspect, relate to purified antibodies that selectively bind to an epitope of a mutant $Na_v1.7$ sodium channel alpha-subunit. In one aspect, the purified antibody selectively binds to an epitope of the I62V mutant $Na_v1.7$ sodium channel alpha-subunit. In another aspect, the purified antibody selectively binds to an epitope of the P149Q mutant $Na_v1.7$ sodium channel alpha-subunit. In yet another aspect, the purified antibody selectively binds to an epitope of the N641Y mutant $Na_v1.7$ sodium channel alpha-subunit. In a further aspect, the purified antibody selectively binds to an epitope of the K655R mutant $Na_v1.7$ sodium channel alpha-subunit. In a still further aspect, the purified antibody selectively binds to an epitope of the I739V mutant $Na_v1.7$ sodium channel alpha-subunit. In one aspect, the purified antibody selectively binds to an epitope of the L1123F mutant $Na_v1.7$ sodium channel alpha-subunit.

By "selectively binds" is meant that the antibody binds to the mutant $Na_v1.7$ sodium channel without appreciably binding to the non-mutant $Na_v1.7$ sodium channel. By "binding" is meant such that the signal that indicates binding is at least about 1.5 times the signal for a non-binding control. Thus, without appreciable binding is meant less than or equal to 1.5 times the background of a non-binding control.

The term "antibodies" is used herein in a broad sense and includes both polyclonal and monoclonal antibodies, as well as humanized, fully human, and non-human antibodies. Also provided are fragments of these antibodies wherein the fragments selectively bind with epitopes of mutant $Na_v1.7$ sodium channel alpha-subunits. The antibodies can be tested for their desired binding activity using the in vitro assays described herein, or by analogous methods. Optionally, the antibodies are labeled directly or indirectly and can be used with imaging technologies to detect expression of the mutant $Na_v1.7$.

The term "monoclonal antibody" as used herein refers to an antibody obtained from a substantially homogeneous population of antibodies, i.e., the individual antibodies within the population are identical except for possible naturally occurring mutations that may be present in a small subset of the antibody molecules. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity (See, U.S. Pat. No. 4,816,567 and Morrison, et al. (1984) Proc Natl Acad Sci USA, 81:6851-6855).

The disclosed monoclonal antibodies can be made using any procedure which produces monoclonal antibodies. For example, disclosed monoclonal antibodies can be prepared using hybridoma methods, such as those described by Kohler, et al. (1975) Nature 256:495). In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro, e.g., using the mutant $Na_v1.7$ channels described herein.

The monoclonal antibodies may also be made by recombinant DNA methods, such as those described in U.S. Pat. No. 4,816,567. DNA encoding the disclosed monoclonal antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques, e.g., as described in U.S. Pat. Nos. 5,804,440 and 6,096,441.

In vitro methods are also suitable for preparing monovalent antibodies, including, for example, scfv antibodies. Digestion of antibodies to produce fragments thereof, particularly, Fab fragments, can be accomplished using routine techniques known in the art. For instance, digestion can be performed using papain. Examples of papain digestion are described in WO 94/29348 and U.S. Pat. No. 4,342,566. Papain digestion of antibodies typically produces two identical antigen binding fragments, called Fab fragments, each with a single antigen binding site, and a residual Fc fragment. Pepsin treatment yields a fragment that has two antigen combining sites and is still capable of cross linking antigen.

The fragments, whether attached to other sequences or not, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment. (See Zoller, (1992) J Curr Opin Biotechnol 3:348-354).

As used herein, the term "antibody" or "antibodies" can also refer to a human antibody and/or a humanized antibody. Many non-human antibodies (e.g. those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

Human Antibodies

The disclosed human antibodies can be prepared using any technique. Examples of techniques for human monoclonal antibody production include those described by Cole et al. (Monoclonal Antibodies and Cancer Therapy, Alan R. Liss, p. 77, 1985) and by Boerner, et al. (1991) J Immunol 147:86-95. Human antibodies (and fragments thereof) can also be produced using phage display libraries (see Hoogenboom, et al. (1991) J Mol Biol 227:381; Marks, et al. (1991) J Mol Biol 222:581).

The disclosed human antibodies can also be obtained from transgenic animals. For example, transgenic, mutant mice that are capable of producing a full repertoire of human antibodies, in response to immunization, have been described (see, e.g., Jakobovits, et al. (1993) Proc Natl Acad Sci USA 90:2551-2555; Jakobovits, et al. (1993) Nature 362:255-258; Bruggermann, et al. (1993) Year in Immunol 7:33). Specifically, the homozygous deletion of the antibody heavy chain joining region (J(H)) gene in these chimeric and germ line mutant mice results in complete inhibition of endogenous antibody production, and the successful transfer of the human germ line antibody gene array into such germ line mutant mice results in the production of human antibodies upon antigen challenge. Antibodies having the desired activity are selected using the mutant $Na_v1.7$ sodium channels provided herein.

Humanized Antibodies

Antibody humanization techniques generally involve the use of recombinant DNA technology to manipulate the DNA sequence encoding one or more polypeptide regions of an antibody molecule. Accordingly, a humanized form of a non-human antibody (or a fragment thereof) is a chimeric antibody or antibody chain (or a fragment thereof, such as an Fv, Fab, Fab', or other antigen binding portion of an antibody) which contains a portion of an antigen binding site from a non-human (donor) antibody integrated into the framework of a human (recipient) antibody.

To generate a humanized antibody, residues from one or more complementarity determining regions (CDRs) of a recipient (human) antibody molecule are replaced by residues from one or more CDRs of a donor (non-human) antibody molecule that is known to have desired antigen binding characteristics (e.g., a certain level of specificity and affinity for the target antigen). In some instances, Fv framework (FR) residues of the human antibody are replaced by corresponding non-human residues. Humanized antibodies may also contain residues which are found neither in the recipient antibody nor in the imported CDR or framework sequences. Generally, a humanized antibody has one or more amino acid residues introduced into it from a source which is non-human. In practice, humanized antibodies are typically human antibodies in which some CDR residues and possibly some FR residues are substituted by residues from analogous sites in rodent antibodies. Humanized antibodies generally contain at least a portion of an antibody constant region (Fc), typically that of a human antibody (see Jones, et al. (1986) Nature 321:522-525; Reichmann, et al. (1988) Nature 332:323-327; Presta, (1992) Curr Opin Struct Biol 2:593-596).

Methods for humanizing non-human antibodies are well known in the art. For example, humanized antibodies can be generated according to the methods of Winter and co-workers (Jones, et al. (1986) Nature 321:522-525; Riechmann, et al. (1988) Nature 332:323-327; Verhoeyen, et al. (1988) Science 239:1534-1536), by substituting rodent CDRs or CDR sequences for the corresponding sequences of a human antibody. Methods that can be used to produce humanized antibodies are also described in U.S. Pat. Nos. 4,816,567, 5,565, 332, 5,721,367, 5,837,243, 5,939,598, 6,130,364, and 6,180, 377.

In one aspect, as a form of therapy, antibodies can be used to inactivate the function of a mutant protein.

Methods of Drug Screening and Delivery

The materials, compositions, articles, devices and methods disclosed herein, in one aspect, relate to a method of identifying a compound that modulates mutant $Na_v1.7$ sodium channels comprising contacting, with a test compound, a cell containing a mutant $Na_v1.7$ nucleic acid that encodes a mutant $Na_v1.7$ sodium channel comprising one or more mutations at residue 62, residue 149, residue 641, residue 655, residue 739, or residue 1123 of the channel; detecting $Na_v1.7$ sodium channel activity; and comparing the $Na_v1.7$ sodium channel activity in the contacted cell with the amount of $Na_v1.7$ sodium channel activity in a control cell, wherein the control cell is not contacted by the test compound, an increased or decreased $Na_v1.7$ sodium channel activity in the test cell as compared to the control cell indicating a compound that modulates mutant $Na_v1.7$ sodium channels. Detecting sodium channel activity can be accomplished by methods known in the art. For example, a suitable protocol for detecting sodium channel activity is described in Kausalia, et al. (2003) J. Neurophysiol. 10.1152/jn.00676.2003.

The cell can express the mutant channel naturally or can be genetically modified to do so. Optionally, the cell is an oocyte that expressed the mutant sodium channel. The mutant sodium channel can be a I62V, P149Q, N641Y, K655R, I739V, or L1123F mutant. Optionally, a mutant channel can comprise one or more of the site mutations.

Optionally, channel activity is tested using intracellular or extracellular recording to assess changes in membrane potential associated with sodium ion flux. Alternatively, imaging technologies can be used to observe labeled ion flux. Expression can be assessed in *Xenopus* oocytes or mammalian cells such as CHO, HEK and tsa201. Mutations may result in errors of protein trafficking and protein interaction. As such, mutant channels can be assessed for their ability to form functional channels in the cell membrane as opposed to being retained in the endoplasmic reticulum by using labeled antibodies to the wild-type channel, or by attaching a common epitope to the channels and using a specific antibody to that epitope. Mutations that alter interactions with intracellular proteins, such as protein kinase A, protein kinase C or calmodulin kinase, or the sodium channel beta-subunits, can be identified through yeast 2-hybrid studies, co-immunoprecipitation experiments or electrophysiological experiments.

Also, the materials, compositions, articles, devices, and methods disclosed herein, in one aspect, relate to a method of preventing or reducing the effects of neurologic disorders like febrile seizures, afebrile seizures, or epilepsy by treating a subject at risk for neurologic disorders with a composition that modulates mutant $Na_v1.7$ levels. Thus, a subject with a mutation(s) in $Na_v1.7$ sodium channel alpha-subunits, consistent with a neurologic disorder or an increased risk of a neurologic disorder, can be treated with a composition comprising a mutant $Na_v1.7$ modulator identified or manufactured using the methods taught herein.

The materials and compositions disclosed herein can be administered in vivo in a pharmaceutically acceptable carrier. By "pharmaceutically acceptable carrier" is meant a material that is not biologically or otherwise undesirable, i.e., the material may be administered to a subject, along with a modulator of $Na_v1.7$ sodium channel function identified or made by the methods taught herein, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously), by intramuscular injection, by intraperitoneal injection, transdermally, extracorporeally, topically or the like, although topical intranasal administration or administration by inhalant is typically preferred. As used herein, "topical intranasal administration" means delivery of the compositions into the nose and nasal passages through one or both of the nares and can comprise delivery by a spraying mechanism or droplet mechanism, or through aerosolization of the composition. The latter may be effective when a large number of animals are to be treated simultaneously. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the disorder being treated, the particular nucleic acid or modulator used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials may be in solution, suspension (for example, incorporated into microparticles, liposomes, or cells). These may be targeted to a particular cell type via antibodies, receptors, or receptor ligands.

Liposomes are vesicles comprised of one or more concentrically ordered lipid bilayers which encapsulate an aqueous phase. They are normally not leaky, but can become leaky if a hole or pore occurs in the membrane, if the membrane is dissolved or degrades, or if the membrane temperature is increased to the phase transition temperature. Current methods of drug delivery via liposomes require that the liposome carrier ultimately become permeable and release the encapsulated drug at the target site. This can be accomplished, for example, in a passive manner wherein the liposome bilayer degrades over time through the action of various agents in the body. Every liposome composition will have a characteristic half-life in the circulation or at other sites in the body and, thus, by controlling the half-life of the liposome composition, the rate at which the bilayer degrades can be somewhat regulated.

In contrast to passive drug release, active drug release involves using an agent to induce a permeability change in the liposome vesicle. Liposome membranes can be constructed so that they become destabilized when the environment becomes acidic near the liposome membrane (see, e.g. (1987) Proc Natl Acad Sci USA 84:7851; (1989) Biochemistry 28:908, which are hereby incorporated by reference in their entireties for their teachings of liposome construction and administration). When liposomes are endocytosed by a target cell, for example, they can be routed to acidic endosomes which will destabilize the liposome and result in drug release.

Alternatively, the liposome membrane can be chemically modified such that an enzyme is placed as a coating on the membrane which slowly destabilizes the liposome. Since control of drug release depends on the concentration of enzyme initially placed in the membrane, there is no real effective way to modulate or alter drug release to achieve "on demand" drug delivery. The same problem exists for pH-sensitive liposomes in that as soon as the liposome vesicle comes into contact with a target cell, it will be engulfed and a drop in pH will lead to drug release. This liposome delivery system can also be made to target B cells by incorporating into the liposome structure a ligand having an affinity for B cell-specific receptors.

Compositions including the liposomes in a pharmaceutically acceptable carrier are also contemplated.

Transdermal delivery devices have been employed for delivery of low molecular weight proteins by using lipid-based compositions (i.e., in the form of a patch) in combination with sonophoresis. However, as reported in U.S. Pat. No. 6,041,253, which is hereby incorporated by reference in its entirety for the methods taught therein, transdermal delivery can be further enhanced by the application of an electric field, for example, by ionophoresis or electroporation. Using low frequency ultrasound which induces cavitation of the lipid layers of the stratum corneum, higher transdermal fluxes, rapid control of transdermal fluxes, and drug delivery at lower ultrasound intensities can be achieved. Still further enhancement can be obtained using a combination of chemical enhancers and/or magnetic field along with the electric field and ultrasound.

Implantable or injectable protein depot compositions can also be employed, providing long-term delivery of the composition. For example, U.S. Pat. No. 6,331,311, which is hereby incorporated by reference in its entirety for protein depot compositions and uses, reports an injectable depot gel composition which includes a biocompatible polymer, a solvent that dissolves the polymer and forms a viscous gel, and an emulsifying agent in the form of a dispersed droplet phase in the viscous gel. Upon injection, such a gel composition can provide a relatively continuous rate of dispersion of the agent to be delivered, thereby avoiding an initial burst of the agent to be delivered.

The test compound and modulator taught herein can be, but is not limited to, antibodies, chemicals, small molecules, modified antisense RNAs, ions, siRNAs, receptor ligands, drugs and secreted proteins.

EXAMPLES

The following examples are put forth so as to provide those of ordinary skill in the art with a complete disclosure and description of how the antibodies, polypeptides, nucleic acids, compositions, and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for.

Example 1

Febrile seizures are the most common seizure disorder of early childhood, exhibiting a prevalence of 2-5% in European and North American children and as high as 9% in the Japanese. The incidence of febrile seizures in first-degree relatives is 31% (Aicardi, Epilepsy in Children, Raven Press, New York, N.Y. (1994)), supporting a strong genetic etiology of febrile seizures. The impact of febrile seizures is considerable because individuals who experience febrile seizures have a 2-7% chance of developing afebrile seizures later in life (Annegers, et al. (1987) N Engl J Med 316:493-498). These later epileptic phenomena include cases of various generalized convulsive, as well as simple and complex partial seizures.

Linkage analysis of a febrile seizure kindred K4425 identified a 10 cM region of no recombination on chromosome 2q24 (FEB3, OMIM 604403), which contains five sodium channel alpha-subunit genes (see Peiffer, et al. (1999) Ann Neurol 46:671-678). Three of the sodium channel genes within this critical region, $Na_v1.1$, $Na_v1.2$, and $Na_v1.3$, share over 85% identity and are highly expressed in brain (see Catterall, (2000) Neuron 26:13-25). $Na_v1.7$, which also resides within this critical genetic interval, shares approximately 70-80% homology with $Na_v1.1$, $Na_v1.2$, and $Na_v1.3$ (see Catterall, (2000) Neuron 26:13-25; Sangameswaran, et al. (1997) J Biol Chem 272:14805-14809), is expressed primarily in neurons of the dorsal root ganglia, and shows minimal to no expression in brain (Felts, et al. (1997) Brain Res Mol Brain Res 45:71-82; Toledo-Aral, et al. (1997) Proc Natl Acad Sci USA 94:1527-1532). Consequently, $Na_v1.7$ has been classified as a peripheral nervous system channel (Catterall, (2000) Neuron 26:13-25; Goldin, et al. (2001) Annu Rev Physiol 63:871-894).

Figure 2:
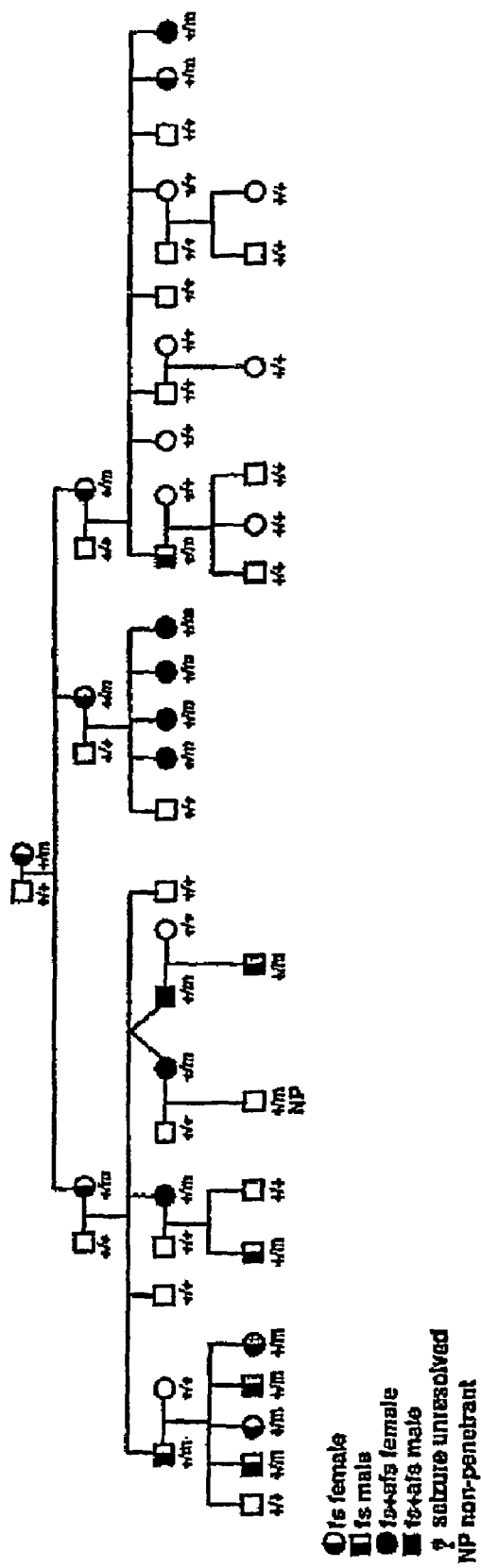
FIG. 2 is a diagram showing the segregation of the N641Y mutation and phenotypic findings of kindred 4425. The following abbreviations are used in the diagram: "fs" means febrile seizures; "afs" means afebrile seizures; "+" means wild type; and "m" means mutant.

Recently, disease-causing mutations were identified in $Na_v1.1$ and $Na_v1.2$ in generalized epilepsy febrile seizure plus (GEFS+), a febrile seizure disorder that is subtly different from the phenotype described in kindred K4425 (see Singh, et al. (1999) Ann Neurol 45:75-81; Sugawara, et al. (2001) Proc Natl Acad Sci USA 98:6384-6389; Wallace, et al. (2001) Am J Hum Genet. 68:859-865; Escayg, et al. (2000) Nat Genet 24: 343-345). Sequence analysis of an affected individual in K4425 did not yield any disease-causing variants in either of these two genes, or in the closely related $Na_v1.3$ gene. Sequence analysis of the $Na_v1.7$ large intracellular loop between domains I and II revealed a missense change (N641Y) in all affected individuals of K4425 that was absent from 236 control chromosomes (see FIG. 2).

Figure 3:
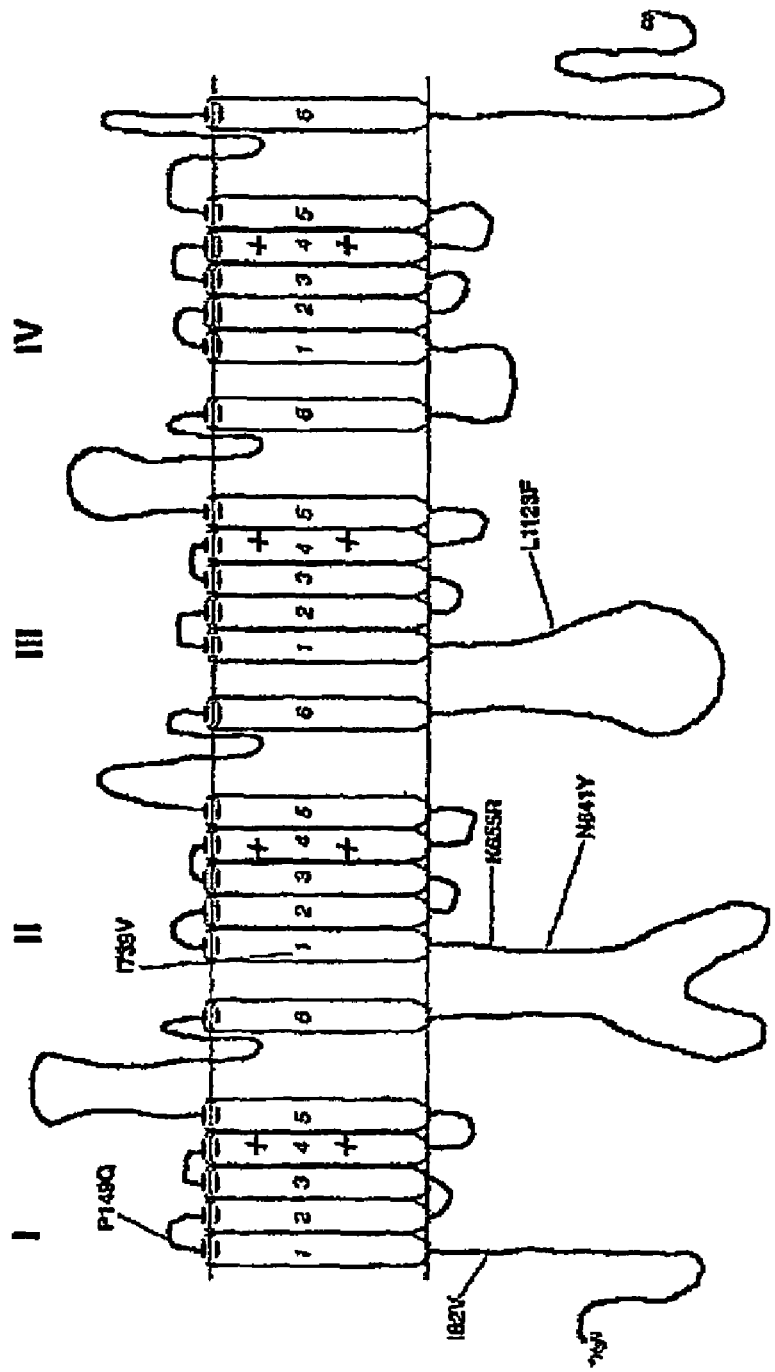
FIG. 3 is a diagram of the secondary structure of a $Na_v1.7$ sodium channel alpha-subunit where the locations of various mutations are identified.

$Na_v1.7$ was then sequenced in a panel of 32 sporadic and familial cases with seizures occurring in the setting of a febrile illness and five additional variants in $Na_v1.7$ that were not found in 180 ethnically matched control chromosomes were identified (Table 2). These variants were identified in the intracellular N-terminus (I62V), the DI S1-S2 extracellular loop (P149Q), the DI-DII intracellular loop (K655R), the DII S1 transmembrane domain (I739V), and the DII-DIII intracellular loop (L1123F) (see FIG. 3).

TABLE 2

Amino acid conservation and clinical findings associated with Nav1.7 mutations

| Exon | Mutation | Amino Acid Species mou/rat/rabb | Conservation Gene family Nav1.1/1.2/1.3 | Family History | Clinical Findings Presentation (age) | Clinical Course |
|---|---|---|---|---|---|---|
| 1 | I62V | ✓ | ✓ | − | FS (2 yr) | FS until 2 yr |
| 3 | P149Q | P/P/A | ✓ | − | FS (2 yr) | FS until 4 yr |
| 11 | N641Y | ✓ | V/A/T | +* | FS (mean 1.3 yr) | GTC, PC, SP, GT, GA until 6-16 yr |
| 12 | K655R | ✓ | R/R/R | + | FS (5 yr) | IGE until 6 yr |
| 13 | I739V | ✓ | ✓ | + | FS (1 yr) | IGE until 8 yr |
| 17 | L1123F | ✓ | A/A/L | − | epilepsy (5 mo) | Intractable seizures |

Species: corresponding amino acid of $Na_v1.7$ of the mouse, rat and rabbit; Gene family: corresponding amino acid of $Na_v1.1$, $Na_v1.2$, and $Na_v1.3$; ✓, amino acid is identical to human $Na_v1.7$. Family history: −, negative; +, positive. FS, febrile seizures; GTC, generalized tonic-clonic; PC, partial complex; SP, simple partial; GT, generalized tonic; GA, generalized atonic; IGE, idiopathic generalized epilepsy; *family described in FIG. 2.

All variants, except proline 149, are conserved in the $Na_v1.7$ gene of mouse, rat and rabbit. Proline 149 is conserved in mouse and rat, and is substituted with alanine in rabbit (Table 2). Less conservation of the mutant $Na_v1.7$ residues is found among the $Na_v1.1$, $Na_v1.2$, and $Na_v1.3$ genes.

A broad variety of neurologic manifestations is observed in patients with mutations in $Na_v1.7$, suggestive of a wide clinical continuum. Illustrating the milder end of the continuum are two probands suffering only of infrequent febrile seizures before six years of age (Table 2: I62V, P149Q). An additional two such patients later developed rare generalized convulsive episodes (associated with generalized epileptiform discharges on EEG) that resolved by eight years of age (Table 2: K655R, I739V). All 21 affected individuals in K4425 experienced febrile seizures before six years of age (Table 2: N641Y). Eight of these individuals had later afebrile seizures which remitted by the age of 16 in six individuals. Peiffer, et al. (1999) Ann Neurol 46:671-678. These patients with afebrile seizures that ultimately resolved suggest an intermediate phenotype. Lastly, one proband in our study experienced multiple generalized clonic seizures which were predominantly afebrile, beginning at five months of age. This patient without a family history of seizures progressed to have frequent episodes of status epilepticus and prolonged complex partial seizures by 16 months, and at 5 years old, continues to have mixed seizures (including probable myoclonic and astatic seizures) in spite of resolute therapeutic intervention. This last case represents the severe end of the clinical spectrum, and may be characterized as similar to SMEI (Table 2: L1123F). There is now abundant evidence for an increasing range of epilepsy phenotypes in patients with mutations in $Na_v1.1$ (see Nabbout, et al. (2003) Neurology 60:1961-1967; Fujiwara, et al. (2003) Brain 126:531-546). Electrophysiological characterization of these unique $Na_v1.7$ mutations may help shed light on the variation in seizure manifestation observed in this group of patients.

To date, $Na_v1.1$ and $Na_vβ1.1$ are the most commonly mutated genes in the febrile seizure phenotype. However, in an Australian cohort of 36 unrelated GEFS+samples, mutations in $Na_v1.1$ and $Na_vβ1.1$ account for only 17% of cases (see Wallace, et al. (2001) Am J Hum Genet. 68:859-865). In our panel of 32 unrelated febrile seizure cases, only one Na$_v$1.1 mutation, R946H, was identified. Na$_v$1.1 is implicated as a major cause of SMEI or Dravet syndrome (see Nabbout, et al. (2003) Neurology 60:1961-1967; Fujiwara, et al. (2003) Brain 126:531-546; Claes, et al. (2003) Hum Mutat 21:615-621). Since, GEFS+, and possibly SMEI, exhibit genetic heterogeneity, there can be a prevalence of Na$_v$1.7 mutations in cohorts of both disorders.

Example 2

Figure 4:
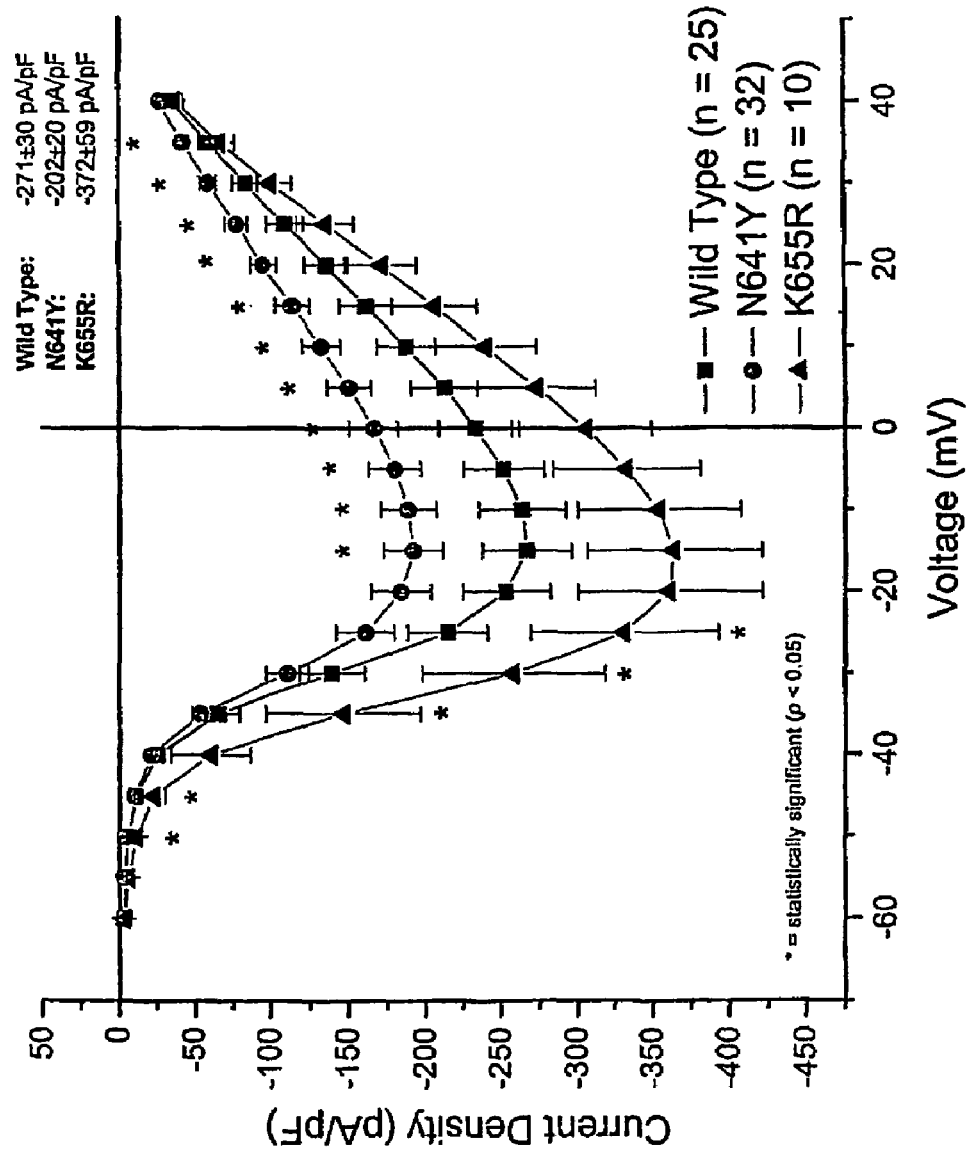
FIG. 4 is a graph showing current voltage relationships of whole-cell currents. Full-length wild-type SCN9A and mutant SCN9A (K655R and N641Y) constructs were transiently transfected into tsA201 cells. Currents were elicited by test pulses from −60 mV to +40 mV in 5 mV increments. At negative potentials, K655R has a higher current density than wild type. At positive potentials, N641Y has reduced current density compared to wild-type, p<0.05.

Experiments were conducted as described in Lossin, et al., (2003) J Neurosci 23(36): 11289-11295. Results are shown in FIG. 4. Full-length wild-type SCN9A and mutant SCN9A (K655R and N641Y) constructs were transiently transfected into tsA201 cells. Currents were elicted by test pulses from −60 mV to +40 mV in 5 mV increments. At negative potentials, K655R has a higher current density than wild type. At positive potentials, N641Y has reduced current density compared to wild-type, p<0.05.

Throughout this application, various publications are referenced. The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of characterizing a nucleic acid sequence that encodes a Na$_v$1.7 sodium channel alpha subunit, comprising the step of identifying mutations in regions of the nucleic acid sequence that encode an intracellular loop between domains I and II, wherein the mutation encodes amino acid residue which corresponds to amino acid residue 641 of human Na$_v$1.7 sodium channel alpha subunit, such identified nucleotides indicating the character of the nucleic acid sequence.

2. The method of claim 1, wherein the encoded amino acid residue is tyrosine.

3. The method of claim 1, wherein the step of identifying the mutations comprises comparing the nucleic acid sequence to a wild-type nucleic acid sequence.

4. The method of claim 3, wherein the wild-type nucleic acid sequence encodes the amino acid sequence of SEQ ID NO: 38.

5. The method of claim 1, wherein the identifying step comprises obtaining a biological sample and testing the sample to identify the nucleotides at the mutations sites of the nucleic acid contained therein.

6. The method of claim 5, wherein the sample is tested by sequencing or probing the nucleic acid.

7. The method of claim 6, wherein the testing step comprises the step of amplifying the nucleic acid contained in the sample.

8. The method of claim 7, wherein the testing step further comprises sequencing the amplified nucleic acid.

9. The method of claim 7, wherein the amplifying step comprises a polymerase chain reaction (PCR).

10. The method of claim 7, wherein the amplifying step comprises contacting the nucleic acid with a primer comprising one or more of the sequences of SEQ ID NOs: 20, 21, 22, 23, 24, 25, 26, 27, 28, 29, 30, and 31.

11. A method for determining a Na$_v$1.7 haplotype in a human subject comprising identifying one or more nucleotides encoding amino acid residues 641, wherein the nucleotide or nucleotides indicated the haplotype.

12. A method for determining a subject's predisposition to a neurologic disorder associated with a sodium channel mutation comprising comparing the subject's Na$_v$1.7 haplotype with one or more reference haplotypes that correlate with the neurologic disorder, a similar haplotype in the subject's Na$_v$1.7 haplotype as compared to the reference haplotype or haplotypes indicating a predisposition to the neurologic disorder, wherein the reference haplotype comprises nucleotides that encode mutations which corresponds to amino acid residue 641 of human Na$_v$1.7 sodium channel alpha subunit.

13. The method of claim 12, wherein the neurologic disorder is a seizure disorder.

14. The method of claim 13, wherein the seizure disorder is a febrile seizure disorder.

* * * * *

SEQUENCE LISTING

<160> NUMBER OF SEQ ID NOS: 38

<210> SEQ ID NO 1
<211> LENGTH: 5934
<212> TYPE: DNA
<213> ORGANISM: Artificial Sequence
<220> FEATURE:
<223> OTHER INFORMATION: Description of Artificial Sequence:/note = synthetic construct

<400> SEQUENCE: 1

```
atggcaatgt tgcctccccc aggacctcag agctttgtcc atttcacaaa acagtctctt      60
gccctcattg aacaacgcat tgctgaaaga aaatcaaagg aacccaaaga agaaaagaaa     120
gatgatgatg aagaagcccc aaagccaagc agtgacttgg aagctggcaa acaactgccc     180
ttcatctatg gggacattcc tcccggcatg gtgtcagagc ccctggagga cttggacccc     240
tactatgcag acaaaaagac tttcatagta ttgaacaaag ggaaaacaat cttccgtttc     300
aatgccacac ctgctttata tatgctttct cctttcagtc ctctaagaag aatatctatt     360
aagattttag tacactcctt attcagcatg ctcatcatgt gcactattct gacaaactgc     420
atatttatga ccatgaataa cccgccggac tggaccaaaa atgtcgagta cactttact       480 ggaatatata cttttgaatc acttgtaaaa atccttgcaa gaggcttctg tgtaggagaa     540
ttcacttttc ttcgtgaccc gtggaactgg ctggattttg tcgtcattgt ttttgcgtat     600
ttaacagaat ttgtaaacct aggcaatgtt tcagctcttc gaactttcag agtattgaga     660
gctttgaaaa ctatttctgt aatcccaggc ctgaagacaa ttgtaggggc tttgatccag     720
tcagtgaaga agctttctga tgtcatgatc ctgactgtgt tctgtctgag tgtgtttgca     780
ctaattggac tacagctgtt catgggaaac ctgaagcata atgtttttcg aaattcactt     840
gaaaataatg aaacattaga aagcataatg aatacctag agagtgaaga agactttaga     900
aaatattttt attacttgga aggatccaaa gatgctctcc tttgtggttt cagcacagat     960
tcaggtcagt gtccagaggg gtacacctgt gtgaaaattg gcagaaaccc tgattatgc    1020 tacacgagct ttgacacttt cagctgggcc ttcttagcct tgtttaggct aatgacccaa    1080
gattactggg aaaaccttta ccaacagacg ctgcgtgctg ctggcaaaac ctacatgatc    1140
ttctttgtcg tagtgatttt cctgggctcc ttttatctaa taaacttgat cctggctgtg    1200
gttgccatgg catatgaaga acagaaccag gcaaacattg aagaagctaa acagaaagaa    1260
```

-continued

```
ttagaatttc aacagatgtt agaccgtctt aaaaaagagc aagaagaagc tgaggcaatt    1320
gcagcggcag cggctgaata tacaagtatt aggagaagca gaattatggg cctctcagag    1380
agttcttctg aaacatccaa actgagctct aaaagtgcta agaaagaag aaacagaaga     1440 aagaaaaga atcaaaagaa gctctccagt ggagaggaaa agggagatgc tgagaaattg    1500
tcgaaatcag aatcagagga cagcatcaga agaaaaagtt ccaccttgg tgtcgaaggg    1560 cataggcgag cacatgaaaa gaggttgtct accccaatc agtcaccact cagcattcgt    1620
ggctccttgt tttctgcaag gcgaagcagc agaacaagtc ttttagttt caaaggcaga    1680 ggaagagata taggatctga gactgaattt gccgatgatg agcacagcat ttttggagac    1740
aatgagagca gaagggctc actgtttgtg ccccacagac cccaggagcg acgcagcagt    1800
aacatcagcc aagccagtag gtccccacca atgctgccgg tgaacgggaa aatgcacagt    1860
gctgtggact gcaacggtgt ggtctccctg gttgatggac gctcagccct catgctcccc    1920
aatggacagc ttctgccaga gggcacgacc aatcaaatac acaagaaaag gcgttgtagt    1980
tcctatctcc tttcagagga tatgctgaat gatcccaacc tcagacagag agcaatgagt    2040
agagcaagca tattaacaaa cactgtggaa gaacttgaag agtccagaca aaatgtcca    2100 ccttggtggt acagatttgc acacaaattc ttgatctgga attgctctcc atattggata    2160
aaattcaaaa agtgtatcta ttttattgta atggatcctt ttgtagatct tgcaattacc    2220
atttgcatag ttttaaacac attatttatg gctatggaac caccccaat gactgaggaa     2280 ttcaaaaatg tacttgctat aggaaatttg gtctttactg gaatctttgc agctgaaatg    2340
gtattaaaac tgattgccat ggatccatat gagtatttcc aagtaggctg gaatattttt    2400
gacagcctta ttgtgacttt aagtttagtg gagctctttc tagcagatgt ggaaggattg    2460
tcagttctgc gatcattcag actgctccga gtcttcaagt tggcaaaatc ctggccaaca    2520
ttgaacatgc tgattaagat cattggtaac tcagtagggg ctctaggtaa cctcaccttta   2580 gtgttggcca tcatcgtctt cattttttgct gtggtcggca tgcagctctt tggtaagagc    2640
tacaaagaat gtgtctgcaa gatcaatgat gactgtacgc tcccacggtg gcacatgaac    2700
gacttcttcc actccttcct gattgtgttc cgcgtgctgt gtggagagtg gatagagacc    2760
atgtgggact gtatggaggt cgctggtcaa gctatgtgcc ttattgttta catgatggtc    2820
atggtcattg gaaacctggt ggtcctaaac ctatttctgg ccttattatt gagctcattt    2880
agttcagaca atcttacagc aattgaagaa gaccctgatg caaacaacct ccagattgca    2940
gtgactagaa ttaaaagggg aataaattat gtgaaacaaa ccttacgtga atttattcta    3000
aaagcatttt ccaaaaagcc aaagattcc agggagataa gacaagcaga agatctgaat    3060
actaagaagg aaaactatat ttctaaccat acacttgctg aaatgagcaa aggtcacaat    3120
ttcctcaagg aaaagataa aatcagtggt tttggaagca gcgtggacaa acacttgatg    3180
gaagacagtg atggtcaatc atttattcac aatcccagcc tcacagtgac agtgccaatt    3240
gcacctgggg aatccgattt ggaaaatatg aatgctgagg aacttagcag tgattcggat    3300
agtgaataca gcaaagtgag attaaaccgg tcaagctcct cagagtgcag cacagttgat    3360
aaccctttgc ctggagaagg agaagaagca gaggctgaac ctatgaattc cgatgagcca    3420
gaggcctgtt tcacagatgg ttgtgtacgg aggttctcat gctgccaagt taacatagag    3480
tcagggaaag gaaaaatctg gtggaacatc aggaaaacct gctacaagat tgttgaacac    3540 agttggttg aaagcttcat tgtcctcatg atcctgctca gcagtggtgc cctggctttt    3600
gaagatattt atattgaaag gaaaaagacc attaagatta tcctggagta tgcagacaag    3660
```

```
atcttcactt acatcttcat tctggaaatg cttctaaaat ggatagcata tggttataaa    3720
acatatttca ccaatgcctg gtgttggctg gatttcctaa ttgttgatgt ttctttggtt    3780
actttagtgg caaacactct tggctactca gatcttggcc ccattaaatc ccttcggaca    3840
ctgagagctt taagacctct aagagcctta tctagatttg aaggaatgag gtcgttgtg     3900 aatgcactca taggagcaat tccttccatc atgaatgtgc tacttgtgtg tcttatattc    3960
tggctgatat tcagcatcat gggagtaaat ttgtttgctg gcaagttcta tgagtgtatt    4020
aacaccacag atgggtcacg gtttcctgca agtcaagttc caaatcgttc cgaatgtttt    4080
gcccttatga atgttagtca aaatgtgcga tggaaaaacc tgaaagtgaa ctttgataat    4140
gtcggacttg gttacctatc tctgcttcaa gttgcaactt ttaagggatg gacgattatt    4200
atgtatgcag cagtggattc tgttaatgta gacaagcagc ccaaatatga atatagcctc    4260
tacatgtata tttattttgt cgtctttatc atctttgggt cattcttcac tttgaacttg    4320
ttcattggtg tcatcataga taatttcaac caacagaaaa agaagcttgg aggtcaagac    4380
atctttatga cagaagaaca gaagaaatac tataatgcaa tgaaaaagct ggggtccaag    4440
aagccacaaa agccaattcc tcgaccaggg aacaaaatcc aaggatgtat atttgaccta    4500
gtgacaaatc aagcctttga tattagtatc atggttctta tctgtctcaa catggtaacc    4560
atgatggtag aaaaggaggg tcaaagtcaa catatgactg aagttttata ttggataaat    4620
gtggttttta taatccttt cactggagaa tgtgtgctaa aactgatctc cctcagacac    4680
tactacttca ctgtaggatg gaatattttt gattttgtgg ttgtgattat ctccattgta    4740
ggtatgtttc tagctgattt gattgaaacg tattttgtgt cccctaccct gttccgagtg    4800
atccgtcttg ccaggattgg ccgaatccta cgtctagtca aggagcaaa  ggggatccgc    4860 acgctgctct ttgctttgat gatgtcccctt cctgcgttgt taacatcgg cctcctgctc    4920 ttcctggtca tgttcatcta cgccatcttt ggaatgtcca actttgccta tgttaaaaag    4980
gaagatggaa ttaatgacat gttcaatttt gagacctttg caacagtat gatttgcctg    5040 ttccaaatta caacctctgc tggctgggat ggattgctag cacctattct taacagtaag    5100
ccacccgact gtgacccaaa aaaagttcat cctggaagtt cagttgaagg agactgtggt    5160
aacccatctg ttggaatatt ctactttgtt agttatatca tcatatcctt cctggttgtg    5220
gtgaacatgt acattgcagt catactggag aatttttagtg ttgccactga agaaagtact    5280
gaacctctga gtgaggatga ctttgagatg ttctatgagg tttgggagaa gtttgatccc    5340
gatgcgaccc agttatatag agttctctaaa ctctctgatt ttgcagctgc cctggatcct    5400
cctcttctca tagcaaaacc caacaaagtc cagctcattg ccatggatct gcccatggtt    5460
agtggtgacc ggatccattg tcttgacatc ttatttgctt ttacaaagcg tgttttgggt    5520
gagagtgggg agatggatt ctcttcgttca cagatggaag aaaggttcat gtctgcaaat    5580
ccttccaaag tgtcctatga acccatcaca accacactaa aacggaaaca agaggatgtg    5640
tctgctactg tcattcagcg tgcttataga cgttaccgct taaggcaaaa tgtcaaaaat    5700
atatcaagta tatacataaa agatggagac agagatgatg atttactcaa taaaaaagat    5760
atggcttttg ataatgttaa tgagaactca agtccagaaa aaacagatgc cacttcatcc    5820
accacctctc caccttcata tgatagtgta acaaagccag acaaagagaa atatgaacaa    5880
gacagaacag aaaaggaaga caaagggaaa gacagcaagg aaagcaaaaa atag          5934
```

<210> SEQ ID NO 2

<211> LENGTH: 1977
<212> TYPE: PRT
<213> ORGANISM: Homo Sapien

<400> SEQUENCE: 2

```
Met Ala Met Leu Pro Pro Gly Pro Gln Ser Phe Val His Phe Thr
 1               5                  10                  15

Lys Gln Ser Leu Ala Leu Ile Glu Gln Arg Ile Ala Glu Arg Lys Ser
            20                  25                  30

Lys Glu Pro Lys Glu Glu Lys Lys Asp Asp Asp Glu Glu Ala Pro Lys
        35                  40                  45

Pro Ser Ser Asp Leu Glu Ala Gly Lys Gln Leu Pro Phe Val Tyr Gly
    50                  55                  60

Asp Ile Pro Pro Gly Met Val Ser Glu Pro Leu Glu Asp Leu Asp Pro
65                  70                  75                  80

Tyr Tyr Ala Asp Lys Lys Thr Phe Ile Val Leu Asn Lys Gly Lys Thr
                85                  90                  95

Ile Phe Arg Phe Asn Ala Thr Pro Ala Leu Tyr Met Leu Ser Pro Phe
            100                 105                 110

Ser Pro Leu Arg Arg Ile Ser Ile Lys Ile Leu Val His Ser Leu Phe
        115                 120                 125

Ser Met Leu Ile Met Cys Thr Ile Leu Thr Asn Cys Ile Phe Met Thr
    130                 135                 140

Met Asn Asn Pro Pro Asp Trp Thr Lys Asn Val Glu Tyr Thr Phe Thr
145                 150                 155                 160

Gly Ile Tyr Thr Phe Glu Ser Leu Val Lys Ile Leu Ala Arg Gly Phe
                165                 170                 175

Cys Val Gly Glu Phe Thr Phe Leu Arg Asp Pro Trp Asn Trp Leu Asp
            180                 185                 190

Phe Val Val Ile Val Phe Ala Tyr Leu Thr Glu Phe Val Asn Leu Gly
        195                 200                 205

Asn Val Ser Ala Leu Arg Thr Phe Arg Val Leu Arg Ala Leu Lys Thr
    210                 215                 220

Ile Ser Val Ile Pro Gly Leu Lys Thr Ile Val Gly Ala Leu Ile Gln
225                 230                 235                 240

Ser Val Lys Lys Leu Ser Asp Val Met Ile Leu Thr Val Phe Cys Leu
                245                 250                 255

Ser Val Phe Ala Leu Ile Gly Leu Gln Leu Phe Met Gly Asn Leu Lys
            260                 265                 270

His Lys Cys Phe Arg Asn Ser Leu Glu Asn Asn Glu Thr Leu Glu Ser
        275                 280                 285

Ile Met Asn Thr Leu Glu Ser Glu Glu Asp Phe Arg Lys Tyr Phe Tyr
    290                 295                 300

Tyr Leu Glu Gly Ser Lys Asp Ala Leu Leu Cys Gly Phe Ser Thr Asp
305                 310                 315                 320

Ser Gly Gln Cys Pro Glu Gly Tyr Thr Cys Val Lys Ile Gly Arg Asn
                325                 330                 335

Pro Asp Tyr Gly Tyr Thr Ser Phe Asp Thr Phe Ser Trp Ala Phe Leu
            340                 345                 350

Ala Leu Phe Arg Leu Met Thr Gln Asp Tyr Trp Glu Asn Leu Tyr Gln
        355                 360                 365

Gln Thr Leu Arg Ala Ala Gly Lys Thr Tyr Met Ile Phe Phe Val Val
    370                 375                 380

Val Ile Phe Leu Gly Ser Phe Tyr Leu Ile Asn Leu Ile Leu Ala Val
```

```
                385                 390                 395                 400
Val Ala Met Ala Tyr Glu Glu Gln Asn Gln Ala Asn Ile Glu Glu Ala
                    405                 410                 415
Lys Gln Lys Glu Leu Glu Phe Gln Gln Met Leu Asp Arg Leu Lys Lys
                    420                 425                 430
Glu Gln Glu Glu Ala Glu Ala Ile Ala Ala Ala Ala Glu Tyr Thr
                    435                 440                 445
Ser Ile Arg Arg Ser Arg Ile Met Gly Leu Ser Glu Ser Ser Ser Glu
                450                 455                 460
Thr Ser Lys Leu Ser Ser Lys Ser Ala Lys Glu Arg Arg Asn Arg Arg
465                 470                 475                 480
Lys Lys Lys Asn Gln Lys Lys Leu Ser Ser Gly Glu Glu Lys Gly Asp
                    485                 490                 495
Ala Glu Lys Leu Ser Lys Ser Glu Ser Glu Asp Ser Ile Arg Arg Lys
                    500                 505                 510
Ser Phe His Leu Gly Val Glu Gly His Arg Arg Ala His Glu Lys Arg
                515                 520                 525
Leu Ser Thr Pro Asn Gln Ser Pro Leu Ser Ile Arg Gly Ser Leu Phe
                530                 535                 540
Ser Ala Arg Arg Ser Ser Arg Thr Ser Leu Phe Ser Phe Lys Gly Arg
545                 550                 555                 560
Gly Arg Asp Ile Gly Ser Glu Thr Glu Phe Ala Asp Glu His Ser
                    565                 570                 575
Ile Phe Gly Asp Asn Glu Ser Arg Arg Gly Ser Leu Phe Val Pro His
                    580                 585                 590
Arg Pro Gln Glu Arg Arg Ser Ser Asn Ile Ser Gln Ala Ser Arg Ser
                    595                 600                 605
Pro Pro Met Leu Pro Val Asn Gly Lys Met His Ser Ala Val Asp Cys
                610                 615                 620
Asn Gly Val Val Ser Leu Val Asp Gly Arg Ser Ala Leu Met Leu Pro
625                 630                 635                 640
Asn Gly Gln Leu Leu Pro Glu Gly Thr Thr Asn Gln Ile His Lys Lys
                    645                 650                 655
Arg Arg Cys Ser Ser Tyr Leu Leu Ser Glu Asp Met Leu Asn Asp Pro
                    660                 665                 670
Asn Leu Arg Gln Arg Ala Met Ser Arg Ala Ser Ile Leu Thr Asn Thr
                675                 680                 685
Val Glu Glu Leu Glu Glu Ser Arg Gln Lys Cys Pro Pro Trp Trp Tyr
                    690                 695                 700
Arg Phe Ala His Lys Phe Leu Ile Trp Asn Cys Ser Pro Tyr Trp Ile
705                 710                 715                 720
Lys Phe Lys Lys Cys Ile Tyr Phe Ile Val Met Asp Pro Phe Val Asp
                    725                 730                 735
Leu Ala Ile Thr Ile Cys Ile Val Leu Asn Thr Leu Phe Met Ala Met
                    740                 745                 750
Glu His His Pro Met Thr Glu Glu Phe Lys Asn Val Leu Ala Ile Gly
                755                 760                 765
Asn Leu Val Phe Thr Gly Ile Phe Ala Ala Glu Met Val Leu Lys Leu
                770                 775                 780
Ile Ala Met Asp Pro Tyr Glu Tyr Phe Gln Val Gly Trp Asn Ile Phe
785                 790                 795                 800
Asp Ser Leu Ile Val Thr Leu Ser Leu Val Glu Leu Phe Leu Ala Asp
                    805                 810                 815
```

```
Val Glu Gly Leu Ser Val Leu Arg Ser Phe Arg Leu Arg Val Phe
            820                 825                 830

Lys Leu Ala Lys Ser Trp Pro Thr Leu Asn Met Leu Ile Lys Ile Ile
            835                 840                 845

Gly Asn Ser Val Gly Ala Leu Gly Asn Leu Thr Leu Val Leu Ala Ile
            850                 855                 860

Ile Val Phe Ile Phe Ala Val Val Gly Met Gln Leu Phe Gly Lys Ser
865                 870                 875                 880

Tyr Lys Glu Cys Val Cys Lys Ile Asn Asp Asp Cys Thr Leu Pro Arg
            885                 890                 895

Trp His Met Asn Asp Phe Phe His Ser Phe Leu Ile Val Phe Arg Val
            900                 905                 910

Leu Cys Gly Glu Trp Ile Glu Thr Met Trp Asp Cys Met Glu Val Ala
            915                 920                 925

Gly Gln Ala Met Cys Leu Ile Val Tyr Met Met Val Met Val Ile Gly
            930                 935                 940

Asn Leu Val Val Leu Asn Leu Phe Leu Ala Leu Leu Leu Ser Ser Phe
945                 950                 955                 960

Ser Ser Asp Asn Leu Thr Ala Ile Glu Glu Asp Pro Asp Ala Asn Asn
            965                 970                 975

Leu Gln Ile Ala Val Thr Arg Ile Lys Lys Gly Ile Asn Tyr Val Lys
            980                 985                 990

Gln Thr Leu Arg Glu Phe Ile Leu Lys Ala Phe Ser Lys Lys Pro Lys
            995                 1000                1005

Ile Ser Arg Glu Ile Arg Gln Ala Glu Asp Leu Asn Thr Lys Lys Glu
            1010                1015                1020

Asn Tyr Ile Ser Asn His Thr Leu Ala Glu Met Ser Lys Gly His Asn
1025                1030                1035                1040

Phe Leu Lys Glu Lys Asp Lys Ile Ser Gly Phe Gly Ser Ser Val Asp
            1045                1050                1055

Lys His Leu Met Glu Asp Ser Asp Gly Gln Ser Phe Ile His Asn Pro
            1060                1065                1070

Ser Leu Thr Val Thr Val Pro Ile Ala Pro Gly Glu Ser Asp Leu Glu
            1075                1080                1085

Asn Met Asn Ala Glu Glu Leu Ser Ser Asp Ser Asp Ser Glu Tyr Ser
            1090                1095                1100

Lys Val Arg Leu Asn Arg Ser Ser Ser Ser Glu Cys Ser Thr Val Asp
1105                1110                1115                1120

Asn Pro Leu Pro Gly Glu Gly Glu Glu Ala Glu Ala Glu Pro Met Asn
            1125                1130                1135

Ser Asp Glu Pro Glu Ala Cys Phe Thr Asp Gly Cys Val Arg Arg Phe
            1140                1145                1150

Ser Cys Cys Gln Val Asn Ile Glu Ser Gly Lys Gly Lys Ile Trp Trp
            1155                1160                1165

Asn Ile Arg Lys Thr Cys Tyr Lys Ile Val Glu His Ser Trp Phe Glu
            1170                1175                1180

Ser Phe Ile Val Leu Met Ile Leu Leu Ser Ser Gly Ala Leu Ala Phe
1185                1190                1195                1200

Glu Asp Ile Tyr Ile Glu Arg Lys Lys Thr Ile Lys Ile Ile Leu Glu
            1205                1210                1215

Tyr Ala Asp Lys Ile Phe Thr Tyr Ile Phe Ile Leu Glu Met Leu Leu
            1220                1225                1230
```

-continued

```
Lys Trp Ile Ala Tyr Gly Tyr Lys Thr Tyr Phe Thr Asn Ala Trp Cys
        1235                1240                1245

Trp Leu Asp Phe Leu Ile Val Asp Val Ser Leu Val Thr Leu Val Ala
        1250                1255                1260

Asn Thr Leu Gly Tyr Ser Asp Leu Gly Pro Ile Lys Ser Leu Arg Thr
1265                1270                1275                1280

Leu Arg Ala Leu Arg Pro Leu Arg Ala Leu Ser Arg Phe Glu Gly Met
                1285                1290                1295

Arg Val Val Asn Ala Leu Ile Gly Ala Ile Pro Ser Ile Met Asn
        1300                1305                1310

Val Leu Leu Val Cys Leu Ile Phe Trp Leu Ile Phe Ser Ile Met Gly
        1315                1320                1325

Val Asn Leu Phe Ala Gly Lys Phe Tyr Glu Cys Ile Asn Thr Thr Asp
        1330                1335                1340

Gly Ser Arg Phe Pro Ala Ser Gln Val Pro Asn Arg Ser Glu Cys Phe
1345                1350                1355                1360

Ala Leu Met Asn Val Ser Gln Asn Val Arg Trp Lys Asn Leu Lys Val
                1365                1370                1375

Asn Phe Asp Asn Val Gly Leu Gly Tyr Leu Ser Leu Leu Gln Val Ala
                1380                1385                1390

Thr Phe Lys Gly Trp Thr Ile Ile Met Tyr Ala Ala Val Asp Ser Val
        1395                1400                1405

Asn Val Asp Lys Gln Pro Lys Tyr Glu Tyr Ser Leu Tyr Met Tyr Ile
        1410                1415                1420

Tyr Phe Val Val Phe Ile Ile Phe Gly Ser Phe Phe Thr Leu Asn Leu
1425                1430                1435                1440

Phe Ile Gly Val Ile Ile Asp Asn Phe Asn Gln Gln Lys Lys Lys Leu
                1445                1450                1455

Gly Gly Gln Asp Ile Phe Met Thr Glu Glu Gln Lys Lys Tyr Tyr Asn
                1460                1465                1470

Ala Met Lys Lys Leu Gly Ser Lys Lys Pro Gln Lys Pro Ile Pro Arg
        1475                1480                1485

Pro Gly Asn Lys Ile Gln Gly Cys Ile Phe Asp Leu Val Thr Asn Gln
        1490                1495                1500

Ala Phe Asp Ile Ser Ile Met Val Leu Ile Cys Leu Asn Met Val Thr
1505                1510                1515                1520

Met Met Val Glu Lys Glu Gly Gln Ser Gln His Met Thr Glu Val Leu
                1525                1530                1535

Tyr Trp Ile Asn Val Val Phe Ile Ile Leu Phe Thr Gly Glu Cys Val
        1540                1545                1550

Leu Lys Leu Ile Ser Leu Arg His Tyr Tyr Phe Thr Val Gly Trp Asn
        1555                1560                1565

Ile Phe Asp Phe Val Val Val Ile Ile Ser Ile Val Gly Met Phe Leu
        1570                1575                1580

Ala Asp Leu Ile Glu Thr Tyr Phe Val Ser Pro Thr Leu Phe Arg Val
1585                1590                1595                1600

Ile Arg Leu Ala Arg Ile Gly Arg Ile Leu Arg Leu Val Lys Gly Ala
                1605                1610                1615

Lys Gly Ile Arg Thr Leu Leu Phe Ala Leu Met Met Ser Leu Pro Ala
                1620                1625                1630

Leu Phe Asn Ile Gly Leu Leu Leu Phe Leu Val Met Phe Ile Tyr Ala
        1635                1640                1645

Ile Phe Gly Met Ser Asn Phe Ala Tyr Val Lys Lys Glu Asp Gly Ile
```

```
                            1650                1655                1660
Asn Asp Met Phe Asn Phe Glu Thr Phe Gly Asn Ser Met Ile Cys Leu
1665                1670                1675                1680

Phe Gln Ile Thr Thr Ser Ala Gly Trp Asp Gly Leu Leu Ala Pro Ile
                    1685                1690                1695

Leu Asn Ser Lys Pro Pro Asp Cys Asp Pro Lys Lys Val His Pro Gly
            1700                1705                1710

Ser Ser Val Glu Gly Asp Cys Gly Asn Pro Ser Val Gly Ile Phe Tyr
    1715                1720                1725

Phe Val Ser Tyr Ile Ile Ile Ser Phe Leu Val Val Asn Met Tyr
1730                1735                1740

Ile Ala Val Ile Leu Glu Asn Phe Ser Val Ala Thr Glu Glu Ser Thr
1745                1750                1755                1760

Glu Pro Leu Ser Glu Asp Asp Phe Glu Met Phe Tyr Glu Val Trp Glu
                    1765                1770                1775

Lys Phe Asp Pro Asp Ala Thr Gln Phe Ile Glu Phe Ser Lys Leu Ser
            1780                1785                1790

Asp Phe Ala Ala Ala Leu Asp Pro Pro Leu Leu Ile Ala Lys Pro Asn
    1795                1800                1805

Lys Val Gln Leu Ile Ala Met Asp Leu Pro Met Val Ser Gly Asp Arg
1810                1815                1820

Ile His Cys Leu Asp Ile Leu Phe Ala Phe Thr Lys Arg Val Leu Gly
1825                1830                1835                1840

Glu Ser Gly Glu Met Asp Ser Leu Arg Ser Gln Met Glu Glu Arg Phe
                    1845                1850                1855

Met Ser Ala Asn Pro Ser Lys Val Ser Tyr Glu Pro Ile Thr Thr Thr
            1860                1865                1870

Leu Lys Arg Lys Gln Glu Asp Val Ser Ala Thr Val Ile Gln Arg Ala
    1875                1880                1885

Tyr Arg Arg Tyr Arg Leu Arg Gln Asn Val Lys Asn Ile Ser Ser Ile
1890                1895                1900

Tyr Ile Lys Asp Gly Asp Arg Asp Asp Leu Leu Asn Lys Lys Asp
1905                1910                1915                1920

Met Ala Phe Asp Asn Val Asn Glu Asn Ser Ser Pro Glu Lys Thr Asp
                    1925                1930                1935

Ala Thr Ser Ser Thr Thr Ser Pro Pro Ser Tyr Asp Ser Val Thr Lys
            1940                1945                1950

Pro Asp Lys Glu Lys Tyr Glu Gln Asp Arg Thr Glu Lys Glu Asp Lys
    1955                1960                1965

Gly Lys Asp Ser Lys Glu Ser Lys Lys
    1970                1975

<210> SEQ ID NO 3
<211> LENGTH: 1977
<212> TYPE: PRT
<213> ORGANISM: Homo Sapien

<400> SEQUENCE: 3

Met Ala Met Leu Pro Pro Gly Pro Gln Ser Phe Val His Phe Thr
1               5                   10                  15

Lys Gln Ser Leu Ala Leu Ile Glu Gln Arg Ile Ala Glu Arg Lys Ser
                20                  25                  30

Lys Glu Pro Lys Glu Glu Lys Lys Asp Asp Asp Glu Glu Ala Pro Lys
        35                  40                  45
```

-continued

```
Pro Ser Ser Asp Leu Glu Ala Gly Lys Gln Leu Pro Phe Ile Tyr Gly
 50                  55                  60

Asp Ile Pro Pro Gly Met Val Ser Glu Pro Leu Glu Asp Leu Asp Pro
 65                  70                  75                  80

Tyr Tyr Ala Asp Lys Lys Thr Phe Ile Val Leu Asn Lys Gly Lys Thr
                 85                  90                  95

Ile Phe Arg Phe Asn Ala Thr Pro Ala Leu Tyr Met Leu Ser Pro Phe
            100                 105                 110

Ser Pro Leu Arg Arg Ile Ser Ile Lys Ile Leu Val His Ser Leu Phe
        115                 120                 125

Ser Met Leu Ile Met Cys Thr Ile Leu Thr Asn Cys Ile Phe Met Thr
    130                 135                 140

Met Asn Asn Pro Gln Asp Trp Thr Lys Asn Val Glu Tyr Thr Phe Thr
145                 150                 155                 160

Gly Ile Tyr Thr Phe Glu Ser Leu Val Lys Ile Leu Ala Arg Gly Phe
                165                 170                 175

Cys Val Gly Glu Phe Thr Phe Leu Arg Asp Pro Trp Asn Trp Leu Asp
            180                 185                 190

Phe Val Val Ile Val Phe Ala Tyr Leu Thr Glu Phe Val Asn Leu Gly
        195                 200                 205

Asn Val Ser Ala Leu Arg Thr Phe Arg Val Leu Arg Ala Leu Lys Thr
    210                 215                 220

Ile Ser Val Ile Pro Gly Leu Lys Thr Ile Val Gly Ala Leu Ile Gln
225                 230                 235                 240

Ser Val Lys Lys Leu Ser Asp Val Met Ile Leu Thr Val Phe Cys Leu
                245                 250                 255

Ser Val Phe Ala Leu Ile Gly Leu Gln Leu Phe Met Gly Asn Leu Lys
            260                 265                 270

His Lys Cys Phe Arg Asn Ser Leu Glu Asn Asn Glu Thr Leu Glu Ser
        275                 280                 285

Ile Met Asn Thr Leu Glu Ser Glu Glu Asp Phe Arg Lys Tyr Phe Tyr
    290                 295                 300

Tyr Leu Glu Gly Ser Lys Asp Ala Leu Leu Cys Gly Phe Ser Thr Asp
305                 310                 315                 320

Ser Gly Gln Cys Pro Glu Gly Tyr Thr Cys Val Lys Ile Gly Arg Asn
                325                 330                 335

Pro Asp Tyr Gly Tyr Thr Ser Phe Asp Thr Phe Ser Trp Ala Phe Leu
            340                 345                 350

Ala Leu Phe Arg Leu Met Thr Gln Asp Tyr Trp Glu Asn Leu Tyr Gln
        355                 360                 365

Gln Thr Leu Arg Ala Ala Gly Lys Thr Tyr Met Ile Phe Phe Val Val
    370                 375                 380

Val Ile Phe Leu Gly Ser Phe Tyr Leu Ile Asn Leu Ile Leu Ala Val
385                 390                 395                 400

Val Ala Met Ala Tyr Glu Glu Gln Asn Gln Ala Asn Ile Glu Glu Ala
                405                 410                 415

Lys Gln Lys Glu Leu Glu Phe Gln Gln Met Leu Asp Arg Leu Lys Lys
            420                 425                 430

Glu Gln Glu Glu Ala Glu Ala Ile Ala Ala Ala Ala Glu Tyr Thr
        435                 440                 445

Ser Ile Arg Arg Ser Arg Ile Met Gly Leu Ser Glu Ser Ser Ser Glu
    450                 455                 460

Thr Ser Lys Leu Ser Ser Lys Ser Ala Lys Glu Arg Arg Asn Arg Arg
```

```
                465                 470                 475                 480
Lys Lys Lys Asn Gln Lys Lys Leu Ser Ser Gly Glu Glu Lys Gly Asp
                    485                 490                 495

Ala Glu Lys Leu Ser Lys Ser Glu Ser Glu Asp Ser Ile Arg Arg Lys
            500                 505                 510

Ser Phe His Leu Gly Val Glu Gly His Arg Arg Ala His Glu Lys Arg
            515                 520                 525

Leu Ser Thr Pro Asn Gln Ser Pro Leu Ser Ile Arg Gly Ser Leu Phe
            530                 535                 540

Ser Ala Arg Arg Ser Ser Arg Thr Ser Leu Phe Ser Phe Lys Gly Arg
545                 550                 555                 560

Gly Arg Asp Ile Gly Ser Glu Thr Glu Phe Ala Asp Asp Glu His Ser
                565                 570                 575

Ile Phe Gly Asp Asn Glu Ser Arg Arg Gly Ser Leu Phe Val Pro His
                580                 585                 590

Arg Pro Gln Glu Arg Arg Ser Ser Asn Ile Ser Gln Ala Ser Arg Ser
            595                 600                 605

Pro Pro Met Leu Pro Val Asn Gly Lys Met His Ser Ala Val Asp Cys
            610                 615                 620

Asn Gly Val Val Ser Leu Val Asp Gly Arg Ser Ala Leu Met Leu Pro
625                 630                 635                 640

Asn Gly Gln Leu Leu Pro Glu Gly Thr Thr Asn Gln Ile His Lys Lys
                645                 650                 655

Arg Arg Cys Ser Ser Tyr Leu Leu Ser Glu Asp Met Leu Asn Asp Pro
                660                 665                 670

Asn Leu Arg Gln Arg Ala Met Ser Arg Ala Ser Ile Leu Thr Asn Thr
            675                 680                 685

Val Glu Glu Leu Glu Glu Ser Arg Gln Lys Cys Pro Pro Trp Trp Tyr
            690                 695                 700

Arg Phe Ala His Lys Phe Leu Ile Trp Asn Cys Ser Pro Tyr Trp Ile
705                 710                 715                 720

Lys Phe Lys Lys Cys Ile Tyr Phe Ile Val Met Asp Pro Phe Val Asp
                725                 730                 735

Leu Ala Ile Thr Ile Cys Ile Val Leu Asn Thr Leu Phe Met Ala Met
                740                 745                 750

Glu His His Pro Met Thr Glu Glu Phe Lys Asn Val Leu Ala Ile Gly
            755                 760                 765

Asn Leu Val Phe Thr Gly Ile Phe Ala Ala Glu Met Val Leu Lys Leu
            770                 775                 780

Ile Ala Met Asp Pro Tyr Glu Tyr Phe Gln Val Gly Trp Asn Ile Phe
785                 790                 795                 800

Asp Ser Leu Ile Val Thr Leu Ser Leu Val Glu Leu Phe Leu Ala Asp
                805                 810                 815

Val Glu Gly Leu Ser Val Leu Arg Ser Phe Arg Leu Leu Arg Val Phe
            820                 825                 830

Lys Leu Ala Lys Ser Trp Pro Thr Leu Asn Met Leu Ile Lys Ile Ile
            835                 840                 845

Gly Asn Ser Val Gly Ala Leu Gly Asn Leu Thr Leu Val Leu Ala Ile
            850                 855                 860

Ile Val Phe Ile Phe Ala Val Val Gly Met Gln Leu Phe Gly Lys Ser
865                 870                 875                 880

Tyr Lys Glu Cys Val Cys Lys Ile Asn Asp Asp Cys Thr Leu Pro Arg
                885                 890                 895
```

```
Trp His Met Asn Asp Phe Phe His Ser Phe Leu Ile Val Phe Arg Val
            900                 905                 910

Leu Cys Gly Glu Trp Ile Glu Thr Met Trp Asp Cys Met Glu Val Ala
            915                 920                 925

Gly Gln Ala Met Cys Leu Ile Val Tyr Met Met Val Met Val Ile Gly
            930                 935                 940

Asn Leu Val Val Leu Asn Leu Phe Leu Ala Leu Leu Leu Ser Ser Phe
945                 950                 955                 960

Ser Ser Asp Asn Leu Thr Ala Ile Glu Glu Asp Pro Asp Ala Asn Asn
            965                 970                 975

Leu Gln Ile Ala Val Thr Arg Ile Lys Lys Gly Ile Asn Tyr Val Lys
            980                 985                 990

Gln Thr Leu Arg Glu Phe Ile Leu Lys Ala Phe Ser Lys Lys Pro Lys
            995                 1000                1005

Ile Ser Arg Glu Ile Arg Gln Ala Glu Asp Leu Asn Thr Lys Lys Glu
            1010                1015                1020

Asn Tyr Ile Ser Asn His Thr Leu Ala Glu Met Ser Lys Gly His Asn
1025                1030                1035                1040

Phe Leu Lys Glu Lys Asp Lys Ile Ser Gly Phe Gly Ser Ser Val Asp
            1045                1050                1055

Lys His Leu Met Glu Asp Ser Asp Gly Gln Ser Phe Ile His Asn Pro
            1060                1065                1070

Ser Leu Thr Val Thr Val Pro Ile Ala Pro Gly Glu Ser Asp Leu Glu
            1075                1080                1085

Asn Met Asn Ala Glu Glu Leu Ser Ser Asp Ser Asp Ser Glu Tyr Ser
            1090                1095                1100

Lys Val Arg Leu Asn Arg Ser Ser Ser Glu Cys Ser Thr Val Asp
1105                1110                1115                1120

Asn Pro Leu Pro Gly Glu Gly Glu Ala Glu Ala Glu Pro Met Asn
            1125                1130                1135

Ser Asp Glu Pro Glu Ala Cys Phe Thr Asp Gly Cys Val Arg Arg Phe
            1140                1145                1150

Ser Cys Cys Gln Val Asn Ile Glu Ser Gly Lys Gly Lys Ile Trp Trp
            1155                1160                1165

Asn Ile Arg Lys Thr Cys Tyr Lys Ile Val Glu His Ser Trp Phe Glu
            1170                1175                1180

Ser Phe Ile Val Leu Met Ile Leu Leu Ser Ser Gly Ala Leu Ala Phe
1185                1190                1195                1200

Glu Asp Ile Tyr Ile Glu Arg Lys Lys Thr Ile Lys Ile Ile Leu Glu
            1205                1210                1215

Tyr Ala Asp Lys Ile Phe Thr Tyr Ile Phe Ile Leu Glu Met Leu Leu
            1220                1225                1230

Lys Trp Ile Ala Tyr Gly Tyr Lys Thr Tyr Phe Thr Asn Ala Trp Cys
            1235                1240                1245

Trp Leu Asp Phe Leu Ile Val Asp Val Ser Leu Val Thr Leu Val Ala
            1250                1255                1260

Asn Thr Leu Gly Tyr Ser Asp Leu Gly Pro Ile Lys Ser Leu Arg Thr
1265                1270                1275                1280

Leu Arg Ala Leu Arg Pro Leu Arg Ala Leu Ser Arg Phe Glu Gly Met
            1285                1290                1295

Arg Val Val Val Asn Ala Leu Ile Gly Ala Ile Pro Ser Ile Met Asn
            1300                1305                1310
```

```
Val Leu Leu Val Cys Leu Ile Phe Trp Leu Ile Phe Ser Ile Met Gly
    1315                1320                1325

Val Asn Leu Phe Ala Gly Lys Phe Tyr Glu Cys Ile Asn Thr Thr Asp
    1330                1335                1340

Gly Ser Arg Phe Pro Ala Ser Gln Val Pro Asn Arg Ser Glu Cys Phe
1345                1350                1355                1360

Ala Leu Met Asn Val Ser Gln Asn Val Arg Trp Lys Asn Leu Lys Val
            1365                1370                1375

Asn Phe Asp Asn Val Gly Leu Gly Tyr Leu Ser Leu Leu Gln Val Ala
            1380                1385                1390

Thr Phe Lys Gly Trp Thr Ile Ile Met Tyr Ala Ala Val Asp Ser Val
            1395                1400                1405

Asn Val Asp Lys Gln Pro Lys Tyr Glu Tyr Ser Leu Tyr Met Tyr Ile
            1410                1415                1420

Tyr Phe Val Val Phe Ile Ile Phe Gly Ser Phe Phe Thr Leu Asn Leu
1425                1430                1435                1440

Phe Ile Gly Val Ile Ile Asp Asn Phe Asn Gln Gln Lys Lys Lys Leu
            1445                1450                1455

Gly Gly Gln Asp Ile Phe Met Thr Glu Glu Gln Lys Lys Tyr Tyr Asn
            1460                1465                1470

Ala Met Lys Lys Leu Gly Ser Lys Lys Pro Gln Lys Pro Ile Pro Arg
            1475                1480                1485

Pro Gly Asn Lys Ile Gln Gly Cys Ile Phe Asp Leu Val Thr Asn Gln
            1490                1495                1500

Ala Phe Asp Ile Ser Ile Met Val Leu Ile Cys Leu Asn Met Val Thr
1505                1510                1515                1520

Met Met Val Glu Lys Glu Gly Gln Ser Gln His Met Thr Glu Val Leu
            1525                1530                1535

Tyr Trp Ile Asn Val Val Phe Ile Ile Leu Phe Thr Gly Glu Cys Val
            1540                1545                1550

Leu Lys Leu Ile Ser Leu Arg His Tyr Tyr Phe Thr Val Gly Trp Asn
            1555                1560                1565

Ile Phe Asp Phe Val Val Ile Ile Ser Ile Val Gly Met Phe Leu
            1570                1575                1580

Ala Asp Leu Ile Glu Thr Tyr Phe Val Ser Pro Thr Leu Phe Arg Val
1585                1590                1595                1600

Ile Arg Leu Ala Arg Ile Gly Arg Ile Leu Arg Leu Val Lys Gly Ala
            1605                1610                1615

Lys Gly Ile Arg Thr Leu Leu Phe Ala Leu Met Met Ser Leu Pro Ala
            1620                1625                1630

Leu Phe Asn Ile Gly Leu Leu Leu Phe Leu Val Met Phe Ile Tyr Ala
            1635                1640                1645

Ile Phe Gly Met Ser Asn Phe Ala Tyr Val Lys Lys Glu Asp Gly Ile
            1650                1655                1660

Asn Asp Met Phe Asn Phe Glu Thr Phe Gly Asn Ser Met Ile Cys Leu
1665                1670                1675                1680

Phe Gln Ile Thr Thr Ser Ala Gly Trp Asp Gly Leu Leu Ala Pro Ile
            1685                1690                1695

Leu Asn Ser Lys Pro Pro Asp Cys Asp Pro Lys Lys Val His Pro Gly
            1700                1705                1710

Ser Ser Val Glu Gly Asp Cys Gly Asn Pro Ser Val Gly Ile Phe Tyr
            1715                1720                1725

Phe Val Ser Tyr Ile Ile Ile Ser Phe Leu Val Val Val Asn Met Tyr
```

-continued

```
            1730                1735                1740

Ile Ala Val Ile Leu Glu Asn Phe Ser Val Ala Thr Glu Glu Ser Thr
1745                1750                1755                1760

Glu Pro Leu Ser Glu Asp Asp Phe Glu Met Phe Tyr Glu Val Trp Glu
                1765                1770                1775

Lys Phe Asp Pro Asp Ala Thr Gln Phe Ile Glu Phe Ser Lys Leu Ser
                1780                1785                1790

Asp Phe Ala Ala Ala Leu Asp Pro Leu Leu Ile Ala Lys Pro Asn
        1795                1800                1805

Lys Val Gln Leu Ile Ala Met Asp Leu Pro Met Val Ser Gly Asp Arg
    1810                1815                1820

Ile His Cys Leu Asp Ile Leu Phe Ala Phe Thr Lys Arg Val Leu Gly
1825                1830                1835                1840

Glu Ser Gly Glu Met Asp Ser Leu Arg Ser Gln Met Glu Glu Arg Phe
                1845                1850                1855

Met Ser Ala Asn Pro Ser Lys Val Ser Tyr Glu Pro Ile Thr Thr Thr
                1860                1865                1870

Leu Lys Arg Lys Gln Glu Asp Val Ser Ala Thr Val Ile Gln Arg Ala
        1875                1880                1885

Tyr Arg Arg Tyr Arg Leu Arg Gln Asn Val Lys Asn Ile Ser Ser Ile
        1890                1895                1900

Tyr Ile Lys Asp Gly Asp Arg Asp Asp Leu Leu Asn Lys Lys Asp
1905                1910                1915                1920

Met Ala Phe Asp Asn Val Asn Glu Asn Ser Ser Pro Glu Lys Thr Asp
                1925                1930                1935

Ala Thr Ser Ser Thr Thr Ser Pro Pro Ser Tyr Asp Ser Val Thr Lys
            1940                1945                1950

Pro Asp Lys Glu Lys Tyr Glu Gln Asp Arg Thr Glu Lys Glu Asp Lys
        1955                1960                1965

Gly Lys Asp Ser Lys Glu Ser Lys Lys
        1970                1975

<210> SEQ ID NO 4
<211> LENGTH: 1977
<212> TYPE: PRT
<213> ORGANISM: Homo Sapien

<400> SEQUENCE: 4

Met Ala Met Leu Pro Pro Gly Pro Gln Ser Phe Val His Phe Thr
1               5                   10                  15

Lys Gln Ser Leu Ala Leu Ile Glu Gln Arg Ile Ala Glu Arg Lys Ser
            20                  25                  30

Lys Glu Pro Lys Glu Glu Lys Lys Asp Asp Asp Glu Glu Ala Pro Lys
        35                  40                  45

Pro Ser Ser Asp Leu Glu Ala Gly Lys Gln Leu Pro Phe Ile Tyr Gly
    50                  55                  60

Asp Ile Pro Pro Gly Met Val Ser Glu Pro Leu Glu Asp Leu Asp Pro
65                  70                  75                  80

Tyr Tyr Ala Asp Lys Lys Thr Phe Ile Val Leu Asn Lys Gly Lys Thr
                85                  90                  95

Ile Phe Arg Phe Asn Ala Thr Pro Ala Leu Tyr Met Leu Ser Pro Phe
            100                 105                 110

Ser Pro Leu Arg Arg Ile Ser Ile Lys Ile Leu Val His Ser Leu Phe
        115                 120                 125
```

```
Ser Met Leu Ile Met Cys Thr Ile Leu Thr Asn Cys Ile Phe Met Thr
    130                 135                 140

Met Asn Asn Pro Pro Asp Trp Thr Lys Asn Val Glu Tyr Thr Phe Thr
145                 150                 155                 160

Gly Ile Tyr Thr Phe Glu Ser Leu Val Lys Ile Leu Ala Arg Gly Phe
                165                 170                 175

Cys Val Gly Glu Phe Thr Phe Leu Arg Asp Pro Trp Asn Trp Leu Asp
            180                 185                 190

Phe Val Val Ile Val Phe Ala Tyr Leu Thr Glu Phe Val Asn Leu Gly
        195                 200                 205

Asn Val Ser Ala Leu Arg Thr Phe Arg Val Leu Arg Ala Leu Lys Thr
    210                 215                 220

Ile Ser Val Ile Pro Gly Leu Lys Thr Ile Val Gly Ala Leu Ile Gln
225                 230                 235                 240

Ser Val Lys Lys Leu Ser Asp Val Met Ile Leu Thr Val Phe Cys Leu
                245                 250                 255

Ser Val Phe Ala Leu Ile Gly Leu Gln Leu Phe Met Gly Asn Leu Lys
            260                 265                 270

His Lys Cys Phe Arg Asn Ser Leu Glu Asn Asn Glu Thr Leu Glu Ser
        275                 280                 285

Ile Met Asn Thr Leu Glu Ser Glu Glu Asp Phe Arg Lys Tyr Phe Tyr
    290                 295                 300

Tyr Leu Glu Gly Ser Lys Asp Ala Leu Leu Cys Gly Phe Ser Thr Asp
305                 310                 315                 320

Ser Gly Gln Cys Pro Glu Gly Tyr Thr Cys Val Lys Ile Gly Arg Asn
                325                 330                 335

Pro Asp Tyr Gly Tyr Thr Ser Phe Asp Thr Phe Ser Trp Ala Phe Leu
            340                 345                 350

Ala Leu Phe Arg Leu Met Thr Gln Asp Tyr Trp Glu Asn Leu Tyr Gln
        355                 360                 365

Gln Thr Leu Arg Ala Ala Gly Lys Thr Tyr Met Ile Phe Phe Val Val
    370                 375                 380

Val Ile Phe Leu Gly Ser Phe Tyr Leu Ile Asn Leu Ile Leu Ala Val
385                 390                 395                 400

Val Ala Met Ala Tyr Glu Glu Gln Asn Gln Ala Asn Ile Glu Glu Ala
                405                 410                 415

Lys Gln Lys Glu Leu Glu Phe Gln Gln Met Leu Asp Arg Leu Lys Lys
            420                 425                 430

Glu Gln Glu Glu Ala Glu Ala Ile Ala Ala Ala Ala Glu Tyr Thr
        435                 440                 445

Ser Ile Arg Arg Ser Arg Ile Met Gly Leu Ser Glu Ser Ser Ser Glu
    450                 455                 460

Thr Ser Lys Leu Ser Ser Lys Ser Ala Lys Glu Arg Arg Asn Arg Arg
465                 470                 475                 480

Lys Lys Lys Asn Gln Lys Lys Leu Ser Ser Gly Glu Glu Lys Gly Asp
                485                 490                 495

Ala Glu Lys Leu Ser Lys Ser Glu Ser Glu Asp Ser Ile Arg Arg Lys
            500                 505                 510

Ser Phe His Leu Gly Val Glu Gly His Arg Arg Ala His Glu Lys Arg
        515                 520                 525

Leu Ser Thr Pro Asn Gln Ser Pro Leu Ser Ile Arg Gly Ser Leu Phe
    530                 535                 540

Ser Ala Arg Arg Ser Ser Arg Thr Ser Leu Phe Ser Phe Lys Gly Arg
```

```
                  545                 550                 555                 560
          Gly Arg Asp Ile Gly Ser Glu Thr Glu Phe Ala Asp Asp Glu His Ser
                          565                 570                 575
          Ile Phe Gly Asp Asn Glu Ser Arg Arg Gly Ser Leu Phe Val Pro His
                          580                 585                 590
          Arg Pro Gln Glu Arg Ser Ser Asn Ile Ser Gln Ala Ser Arg Ser
                      595                 600                 605
          Pro Pro Met Leu Pro Val Asn Gly Lys Met His Ser Ala Val Asp Cys
                      610                 615                 620
          Asn Gly Val Val Ser Leu Val Asp Gly Arg Ser Ala Leu Met Leu Pro
          625                 630                 635                 640
          Tyr Gly Gln Leu Leu Pro Glu Gly Thr Thr Asn Gln Ile His Lys Lys
                          645                 650                 655
          Arg Arg Cys Ser Ser Tyr Leu Leu Ser Glu Asp Met Leu Asn Asp Pro
                          660                 665                 670
          Asn Leu Arg Gln Arg Ala Met Ser Arg Ala Ser Ile Leu Thr Asn Thr
                          675                 680                 685
          Val Glu Glu Leu Glu Glu Ser Arg Gln Lys Cys Pro Pro Trp Trp Tyr
                      690                 695                 700
          Arg Phe Ala His Lys Phe Leu Ile Trp Asn Cys Ser Pro Tyr Trp Ile
          705                 710                 715                 720
          Lys Phe Lys Lys Cys Ile Tyr Phe Ile Val Met Asp Pro Phe Val Asp
                          725                 730                 735
          Leu Ala Ile Thr Ile Cys Ile Val Leu Asn Thr Leu Phe Met Ala Met
                          740                 745                 750
          Glu His His Pro Met Thr Glu Glu Phe Lys Asn Val Leu Ala Ile Gly
                          755                 760                 765
          Asn Leu Val Phe Thr Gly Ile Phe Ala Ala Glu Met Val Leu Lys Leu
                      770                 775                 780
          Ile Ala Met Asp Pro Tyr Glu Tyr Phe Gln Val Gly Trp Asn Ile Phe
          785                 790                 795                 800
          Asp Ser Leu Ile Val Thr Leu Ser Leu Val Glu Leu Phe Leu Ala Asp
                          805                 810                 815
          Val Glu Gly Leu Ser Val Leu Arg Ser Phe Arg Leu Leu Arg Val Phe
                      820                 825                 830
          Lys Leu Ala Lys Ser Trp Pro Thr Leu Asn Met Leu Ile Lys Ile Ile
                      835                 840                 845
          Gly Asn Ser Val Gly Ala Leu Gly Asn Leu Thr Leu Val Leu Ala Ile
                      850                 855                 860
          Ile Val Phe Ile Phe Ala Val Val Gly Met Gln Leu Phe Gly Lys Ser
          865                 870                 875                 880
          Tyr Lys Glu Cys Val Cys Lys Ile Asn Asp Asp Cys Thr Leu Pro Arg
                          885                 890                 895
          Trp His Met Asn Asp Phe Phe His Ser Phe Leu Ile Val Phe Arg Val
                          900                 905                 910
          Leu Cys Gly Glu Trp Ile Glu Thr Met Trp Asp Cys Met Glu Val Ala
                      915                 920                 925
          Gly Gln Ala Met Cys Leu Ile Val Tyr Met Met Val Met Val Ile Gly
                      930                 935                 940
          Asn Leu Val Val Leu Asn Leu Phe Leu Ala Leu Leu Leu Ser Ser Phe
          945                 950                 955                 960
          Ser Ser Asp Asn Leu Thr Ala Ile Glu Glu Asp Pro Asp Ala Asn Asn
                          965                 970                 975
```

-continued

```
Leu Gln Ile Ala Val Thr Arg Ile Lys Lys Gly Ile Asn Tyr Val Lys
            980                 985                 990

Gln Thr Leu Arg Glu Phe Ile Leu Lys Ala Phe Ser Lys Lys Pro Lys
            995                1000                1005

Ile Ser Arg Glu Ile Arg Gln Ala Glu Asp Leu Asn Thr Lys Lys Glu
           1010                1015                1020

Asn Tyr Ile Ser Asn His Thr Leu Ala Glu Met Ser Lys Gly His Asn
1025                1030                1035                1040

Phe Leu Lys Glu Lys Asp Lys Ile Ser Gly Phe Gly Ser Ser Val Asp
            1045                1050                1055

Lys His Leu Met Glu Asp Ser Asp Gly Gln Ser Phe Ile His Asn Pro
            1060                1065                1070

Ser Leu Thr Val Thr Val Pro Ile Ala Pro Gly Glu Ser Asp Leu Glu
            1075                1080                1085

Asn Met Asn Ala Glu Glu Leu Ser Ser Asp Ser Asp Ser Glu Tyr Ser
            1090                1095                1100

Lys Val Arg Leu Asn Arg Ser Ser Ser Glu Cys Ser Thr Val Asp
1105                1110                1115                1120

Asn Pro Leu Pro Gly Glu Gly Glu Glu Ala Glu Ala Glu Pro Met Asn
            1125                1130                1135

Ser Asp Glu Pro Glu Ala Cys Phe Thr Asp Gly Cys Val Arg Arg Phe
            1140                1145                1150

Ser Cys Cys Gln Val Asn Ile Glu Ser Gly Lys Gly Lys Ile Trp Trp
            1155                1160                1165

Asn Ile Arg Lys Thr Cys Tyr Lys Ile Val Glu His Ser Trp Phe Glu
            1170                1175                1180

Ser Phe Ile Val Leu Met Ile Leu Leu Ser Ser Gly Ala Leu Ala Phe
1185                1190                1195                1200

Glu Asp Ile Tyr Ile Glu Arg Lys Lys Thr Ile Lys Ile Ile Leu Glu
            1205                1210                1215

Tyr Ala Asp Lys Ile Phe Thr Tyr Ile Phe Ile Leu Glu Met Leu Leu
            1220                1225                1230

Lys Trp Ile Ala Tyr Gly Tyr Lys Thr Tyr Phe Thr Asn Ala Trp Cys
            1235                1240                1245

Trp Leu Asp Phe Leu Ile Val Asp Val Ser Leu Val Thr Leu Val Ala
            1250                1255                1260

Asn Thr Leu Gly Tyr Ser Asp Leu Gly Pro Ile Lys Ser Leu Arg Thr
1265                1270                1275                1280

Leu Arg Ala Leu Arg Pro Leu Arg Ala Leu Ser Arg Phe Glu Gly Met
            1285                1290                1295

Arg Val Val Val Asn Ala Leu Ile Gly Ala Ile Pro Ser Ile Met Asn
            1300                1305                1310

Val Leu Leu Val Cys Leu Ile Phe Trp Leu Ile Phe Ser Ile Met Gly
            1315                1320                1325

Val Asn Leu Phe Ala Gly Lys Phe Tyr Glu Cys Ile Asn Thr Thr Asp
            1330                1335                1340

Gly Ser Arg Phe Pro Ala Ser Gln Val Pro Asn Arg Ser Glu Cys Phe
1345                1350                1355                1360

Ala Leu Met Asn Val Ser Gln Asn Val Arg Trp Lys Asn Leu Lys Val
            1365                1370                1375

Asn Phe Asp Asn Val Gly Leu Gly Tyr Leu Ser Leu Leu Gln Val Ala
            1380                1385                1390
```

```
Thr Phe Lys Gly Trp Thr Ile Ile Met Tyr Ala Ala Val Asp Ser Val
        1395                1400                1405
Asn Val Asp Lys Gln Pro Lys Tyr Glu Tyr Ser Leu Tyr Met Tyr Ile
    1410                1415                1420
Tyr Phe Val Val Phe Ile Ile Phe Gly Ser Phe Phe Thr Leu Asn Leu
1425                1430                1435                1440
Phe Ile Gly Val Ile Ile Asp Asn Phe Asn Gln Gln Lys Lys Lys Leu
            1445                1450                1455
Gly Gly Gln Asp Ile Phe Met Thr Glu Glu Gln Lys Lys Tyr Tyr Asn
        1460                1465                1470
Ala Met Lys Lys Leu Gly Ser Lys Lys Pro Gln Lys Pro Ile Pro Arg
    1475                1480                1485
Pro Gly Asn Lys Ile Gln Gly Cys Ile Phe Asp Leu Val Thr Asn Gln
    1490                1495                1500
Ala Phe Asp Ile Ser Ile Met Val Leu Ile Cys Leu Asn Met Val Thr
1505                1510                1515                1520
Met Met Val Glu Lys Glu Gly Gln Ser Gln His Met Thr Glu Val Leu
            1525                1530                1535
Tyr Trp Ile Asn Val Val Phe Ile Ile Leu Phe Thr Gly Glu Cys Val
        1540                1545                1550
Leu Lys Leu Ile Ser Leu Arg His Tyr Tyr Phe Thr Val Gly Trp Asn
    1555                1560                1565
Ile Phe Asp Phe Val Val Val Ile Ile Ser Ile Val Gly Met Phe Leu
    1570                1575                1580
Ala Asp Leu Ile Glu Thr Tyr Phe Val Ser Pro Thr Leu Phe Arg Val
1585                1590                1595                1600
Ile Arg Leu Ala Arg Ile Gly Arg Ile Leu Arg Leu Val Lys Gly Ala
            1605                1610                1615
Lys Gly Ile Arg Thr Leu Leu Phe Ala Leu Met Met Ser Leu Pro Ala
        1620                1625                1630
Leu Phe Asn Ile Gly Leu Leu Leu Phe Leu Val Met Phe Ile Tyr Ala
    1635                1640                1645
Ile Phe Gly Met Ser Asn Phe Ala Tyr Val Lys Lys Glu Asp Gly Ile
    1650                1655                1660
Asn Asp Met Phe Asn Phe Glu Thr Phe Gly Asn Ser Met Ile Cys Leu
1665                1670                1675                1680
Phe Gln Ile Thr Thr Ser Ala Gly Trp Asp Gly Leu Leu Ala Pro Ile
            1685                1690                1695
Leu Asn Ser Lys Pro Pro Asp Cys Asp Pro Lys Lys Val His Pro Gly
        1700                1705                1710
Ser Ser Val Glu Gly Asp Cys Gly Asn Pro Ser Val Gly Ile Phe Tyr
    1715                1720                1725
Phe Val Ser Tyr Ile Ile Ile Ser Phe Leu Val Val Val Asn Met Tyr
    1730                1735                1740
Ile Ala Val Ile Leu Glu Asn Phe Ser Val Ala Thr Glu Glu Ser Thr
1745                1750                1755                1760
Glu Pro Leu Ser Glu Asp Asp Phe Glu Met Phe Tyr Glu Val Trp Glu
            1765                1770                1775
Lys Phe Asp Pro Asp Ala Thr Gln Phe Ile Glu Phe Ser Lys Leu Ser
        1780                1785                1790
Asp Phe Ala Ala Ala Leu Asp Pro Pro Leu Leu Ile Ala Lys Pro Asn
    1795                1800                1805
Lys Val Gln Leu Ile Ala Met Asp Leu Pro Met Val Ser Gly Asp Arg
```

-continued

```
                1810                1815                1820

Ile His Cys Leu Asp Ile Leu Phe Ala Phe Thr Lys Arg Val Leu Gly
1825                1830                1835                1840

Glu Ser Gly Glu Met Asp Ser Leu Arg Ser Gln Met Glu Gly Arg Phe
                1845                1850                1855

Met Ser Ala Asn Pro Ser Lys Val Ser Tyr Glu Pro Ile Thr Thr Thr
                1860                1865                1870

Leu Lys Arg Lys Gln Glu Asp Val Ser Ala Thr Val Ile Gln Arg Ala
                1875                1880                1885

Tyr Arg Arg Tyr Arg Leu Arg Gln Asn Val Lys Asn Ile Ser Ser Ile
                1890                1895                1900

Tyr Ile Lys Asp Gly Asp Arg Asp Asp Leu Leu Asn Lys Lys Asp
1905                1910                1915                1920

Met Ala Phe Asp Asn Val Asn Glu Asn Ser Ser Pro Glu Lys Thr Asp
                1925                1930                1935

Ala Thr Ser Ser Thr Thr Ser Pro Pro Ser Tyr Asp Ser Val Thr Lys
                1940                1945                1950

Pro Asp Lys Glu Lys Tyr Glu Gln Asp Arg Thr Glu Lys Glu Asp Lys
                1955                1960                1965

Gly Lys Asp Ser Lys Glu Ser Lys Lys
    1970                1975

<210> SEQ ID NO 5
<211> LENGTH: 1977
<212> TYPE: PRT
<213> ORGANISM: Homo Sapien

<400> SEQUENCE: 5

Met Ala Met Leu Pro Pro Gly Pro Gln Ser Phe Val His Phe Thr
1               5                   10                  15

Lys Gln Ser Leu Ala Leu Ile Glu Gln Arg Ile Ala Glu Arg Lys Ser
                20                  25                  30

Lys Glu Pro Lys Glu Glu Lys Lys Asp Asp Asp Glu Glu Ala Pro Lys
            35                  40                  45

Pro Ser Ser Asp Leu Glu Ala Gly Lys Gln Leu Pro Phe Ile Tyr Gly
        50                  55                  60

Asp Ile Pro Pro Gly Met Val Ser Glu Pro Leu Glu Asp Leu Asp Pro
65                  70                  75                  80

Tyr Tyr Ala Asp Lys Lys Thr Phe Ile Val Leu Asn Lys Gly Lys Thr
                85                  90                  95

Ile Phe Arg Phe Asn Ala Thr Pro Ala Leu Tyr Met Leu Ser Pro Phe
            100                 105                 110

Ser Pro Leu Arg Arg Ile Ser Ile Lys Ile Leu Val His Ser Leu Phe
        115                 120                 125

Ser Met Leu Ile Met Cys Thr Ile Leu Thr Asn Cys Ile Phe Met Thr
    130                 135                 140

Met Asn Asn Pro Pro Asp Trp Thr Lys Asn Val Glu Tyr Thr Phe Thr
145                 150                 155                 160

Gly Ile Tyr Thr Phe Glu Ser Leu Val Lys Ile Leu Ala Arg Gly Phe
                165                 170                 175

Cys Val Gly Glu Phe Thr Phe Leu Arg Asp Pro Trp Asn Trp Leu Asp
            180                 185                 190

Phe Val Val Ile Val Phe Ala Tyr Leu Thr Glu Phe Val Asn Leu Gly
        195                 200                 205
```

```
Asn Val Ser Ala Leu Arg Thr Phe Arg Val Leu Arg Ala Leu Lys Thr
    210                 215                 220
Ile Ser Val Ile Pro Gly Leu Lys Thr Ile Val Gly Ala Leu Ile Gln
225                 230                 235                 240
Ser Val Lys Lys Leu Ser Asp Val Met Ile Leu Thr Val Phe Cys Leu
                245                 250                 255
Ser Val Phe Ala Leu Ile Gly Leu Gln Leu Phe Met Gly Asn Leu Lys
            260                 265                 270
His Lys Cys Phe Arg Asn Ser Leu Glu Asn Asn Glu Thr Leu Glu Ser
        275                 280                 285
Ile Met Asn Thr Leu Glu Ser Glu Glu Asp Phe Arg Lys Tyr Phe Tyr
    290                 295                 300
Tyr Leu Glu Gly Ser Lys Asp Ala Leu Leu Cys Gly Phe Ser Thr Asp
305                 310                 315                 320
Ser Gly Gln Cys Pro Glu Gly Tyr Thr Cys Val Lys Ile Gly Arg Asn
                325                 330                 335
Pro Asp Tyr Gly Tyr Thr Ser Phe Asp Thr Phe Ser Trp Ala Phe Leu
            340                 345                 350
Ala Leu Phe Arg Leu Met Thr Gln Asp Tyr Trp Glu Asn Leu Tyr Gln
        355                 360                 365
Gln Thr Leu Arg Ala Ala Gly Lys Thr Tyr Met Ile Phe Phe Val Val
    370                 375                 380
Val Ile Phe Leu Gly Ser Phe Tyr Leu Ile Asn Leu Ile Leu Ala Val
385                 390                 395                 400
Val Ala Met Ala Tyr Glu Glu Gln Asn Gln Ala Asn Ile Glu Glu Ala
                405                 410                 415
Lys Gln Lys Glu Leu Glu Phe Gln Gln Met Leu Asp Arg Leu Lys Lys
            420                 425                 430
Glu Gln Glu Glu Ala Glu Ala Ile Ala Ala Ala Ala Glu Tyr Thr
        435                 440                 445
Ser Ile Arg Arg Ser Arg Ile Met Gly Leu Ser Glu Ser Ser Ser Glu
    450                 455                 460
Thr Ser Lys Leu Ser Ser Lys Ser Ala Lys Glu Arg Arg Asn Arg Arg
465                 470                 475                 480
Lys Lys Lys Asn Gln Lys Lys Leu Ser Ser Gly Glu Glu Lys Gly Asp
                485                 490                 495
Ala Glu Lys Leu Ser Lys Ser Glu Ser Glu Asp Ser Ile Arg Arg Lys
            500                 505                 510
Ser Phe His Leu Gly Val Glu Gly His Arg Arg Ala His Glu Lys Arg
        515                 520                 525
Leu Ser Thr Pro Asn Gln Ser Pro Leu Ser Ile Arg Gly Ser Leu Phe
    530                 535                 540
Ser Ala Arg Arg Ser Ser Arg Thr Ser Leu Phe Ser Phe Lys Gly Arg
545                 550                 555                 560
Gly Arg Asp Ile Gly Ser Glu Thr Glu Phe Ala Asp Asp Glu His Ser
                565                 570                 575
Ile Phe Gly Asp Asn Glu Ser Arg Arg Gly Ser Leu Phe Val Pro His
            580                 585                 590
Arg Pro Gln Glu Arg Arg Ser Ser Asn Ile Ser Gln Ala Ser Arg Ser
        595                 600                 605
Pro Pro Met Leu Pro Val Asn Gly Lys Met His Ser Ala Val Asp Cys
    610                 615                 620
Asn Gly Val Val Ser Leu Val Asp Gly Arg Ser Ala Leu Met Leu Pro
```

-continued

```
                625                 630                 635                 640
Asn Gly Gln Leu Leu Pro Glu Gly Thr Thr Asn Gln Ile His Arg Lys
                645                 650                 655
Arg Arg Cys Ser Ser Tyr Leu Leu Ser Glu Asp Met Leu Asn Asp Pro
                660                 665                 670
Asn Leu Arg Gln Arg Ala Met Ser Arg Ala Ser Ile Leu Thr Asn Thr
                675                 680                 685
Val Glu Glu Leu Glu Glu Ser Arg Gln Lys Cys Pro Pro Trp Trp Tyr
                690                 695                 700
Arg Phe Ala His Lys Phe Leu Ile Trp Asn Cys Ser Pro Tyr Trp Ile
705                 710                 715                 720
Lys Phe Lys Lys Cys Ile Tyr Phe Ile Val Met Asp Pro Phe Val Asp
                725                 730                 735
Leu Ala Ile Thr Ile Cys Ile Val Leu Asn Thr Leu Phe Met Ala Met
                740                 745                 750
Glu His His Pro Met Thr Glu Glu Phe Lys Asn Val Leu Ala Ile Gly
                755                 760                 765
Asn Leu Val Phe Thr Gly Ile Phe Ala Ala Glu Met Val Leu Lys Leu
                770                 775                 780
Ile Ala Met Asp Pro Tyr Glu Tyr Phe Gln Val Gly Trp Asn Ile Phe
785                 790                 795                 800
Asp Ser Leu Ile Val Thr Leu Ser Leu Val Glu Leu Phe Leu Ala Asp
                805                 810                 815
Val Glu Gly Leu Ser Val Leu Arg Ser Phe Arg Leu Leu Arg Val Phe
                820                 825                 830
Lys Leu Ala Lys Ser Trp Pro Thr Leu Asn Met Leu Ile Lys Ile Ile
                835                 840                 845
Gly Asn Ser Val Gly Ala Leu Gly Asn Leu Thr Leu Val Leu Ala Ile
                850                 855                 860
Ile Val Phe Ile Phe Ala Val Val Gly Met Gln Leu Phe Gly Lys Ser
865                 870                 875                 880
Tyr Lys Glu Cys Val Cys Lys Ile Asn Asp Asp Cys Thr Leu Pro Arg
                885                 890                 895
Trp His Met Asn Asp Phe Phe His Ser Phe Leu Ile Val Phe Arg Val
                900                 905                 910
Leu Cys Gly Glu Trp Ile Glu Thr Met Trp Asp Cys Met Glu Val Ala
                915                 920                 925
Gly Gln Ala Met Cys Leu Ile Val Tyr Met Met Val Met Val Ile Gly
                930                 935                 940
Asn Leu Val Val Leu Asn Leu Phe Leu Ala Leu Leu Leu Ser Ser Phe
945                 950                 955                 960
Ser Ser Asp Asn Leu Thr Ala Ile Glu Glu Asp Pro Asp Ala Asn Asn
                965                 970                 975
Leu Gln Ile Ala Val Thr Arg Ile Lys Lys Gly Ile Asn Tyr Val Lys
                980                 985                 990
Gln Thr Leu Arg Glu Phe Ile Leu Lys Ala Phe Ser Lys Lys Pro Lys
                995                 1000                1005
Ile Ser Arg Glu Ile Arg Gln Ala Glu Asp Leu Asn Thr Lys Lys Glu
            1010                1015                1020
Asn Tyr Ile Ser Asn His Thr Leu Ala Glu Met Ser Lys Gly His Asn
1025                1030                1035                1040
Phe Leu Lys Glu Lys Asp Lys Ile Ser Gly Phe Gly Ser Ser Val Asp
                1045                1050                1055
```

-continued

```
Lys His Leu Met Glu Asp Ser Asp Gly Gln Ser Phe Ile His Asn Pro
            1060                1065                1070

Ser Leu Thr Val Thr Val Pro Ile Ala Pro Gly Glu Ser Asp Leu Glu
            1075                1080                1085

Asn Met Asn Ala Glu Glu Leu Ser Ser Asp Ser Asp Ser Glu Tyr Ser
            1090                1095                1100

Lys Val Arg Leu Asn Arg Ser Ser Ser Glu Cys Ser Thr Val Asp
1105                1110                1115                1120

Asn Pro Leu Pro Gly Glu Gly Glu Ala Glu Ala Glu Pro Met Asn
            1125                1130                1135

Ser Asp Glu Pro Glu Ala Cys Phe Thr Asp Gly Cys Val Arg Arg Phe
            1140                1145                1150

Ser Cys Cys Gln Val Asn Ile Glu Ser Gly Lys Gly Lys Ile Trp Trp
            1155                1160                1165

Asn Ile Arg Lys Thr Cys Tyr Lys Ile Val Glu His Ser Trp Phe Glu
            1170                1175                1180

Ser Phe Ile Val Leu Met Ile Leu Leu Ser Ser Gly Ala Leu Ala Phe
1185                1190                1195                1200

Glu Asp Ile Tyr Ile Glu Arg Lys Lys Thr Ile Lys Ile Ile Leu Glu
            1205                1210                1215

Tyr Ala Asp Lys Ile Phe Thr Tyr Ile Phe Ile Leu Glu Met Leu Leu
            1220                1225                1230

Lys Trp Ile Ala Tyr Gly Tyr Lys Thr Tyr Phe Thr Asn Ala Trp Cys
            1235                1240                1245

Trp Leu Asp Phe Leu Ile Val Asp Val Ser Leu Val Thr Leu Val Ala
            1250                1255                1260

Asn Thr Leu Gly Tyr Ser Asp Leu Gly Pro Ile Lys Ser Leu Arg Thr
1265                1270                1275                1280

Leu Arg Ala Leu Arg Pro Leu Arg Ala Leu Ser Arg Phe Glu Gly Met
            1285                1290                1295

Arg Val Val Val Asn Ala Leu Ile Gly Ala Ile Pro Ser Ile Met Asn
            1300                1305                1310

Val Leu Leu Val Cys Leu Ile Phe Trp Leu Ile Phe Ser Ile Met Gly
            1315                1320                1325

Val Asn Leu Phe Ala Gly Lys Phe Tyr Glu Cys Ile Asn Thr Thr Asp
            1330                1335                1340

Gly Ser Arg Phe Pro Ala Ser Gln Val Pro Asn Arg Ser Glu Cys Phe
1345                1350                1355                1360

Ala Leu Met Asn Val Ser Gln Asn Val Arg Trp Lys Asn Leu Lys Val
            1365                1370                1375

Asn Phe Asp Asn Val Gly Leu Gly Tyr Leu Ser Leu Leu Gln Val Ala
            1380                1385                1390

Thr Phe Lys Gly Trp Thr Ile Ile Met Tyr Ala Ala Val Asp Ser Val
            1395                1400                1405

Asn Val Asp Lys Gln Pro Lys Tyr Glu Tyr Ser Leu Tyr Met Tyr Ile
            1410                1415                1420

Tyr Phe Val Val Phe Ile Ile Phe Gly Ser Phe Phe Thr Leu Asn Leu
1425                1430                1435                1440

Phe Ile Gly Val Ile Ile Asp Asn Phe Asn Gln Gln Lys Lys Lys Leu
            1445                1450                1455

Gly Gly Gln Asp Ile Phe Met Thr Glu Glu Gln Lys Lys Tyr Tyr Asn
            1460                1465                1470
```

-continued

```
Ala Met Lys Lys Leu Gly Ser Lys Lys Pro Gln Lys Pro Ile Pro Arg
        1475                1480                1485

Pro Gly Asn Lys Ile Gln Gly Cys Ile Phe Asp Leu Val Thr Asn Gln
        1490                1495                1500

Ala Phe Asp Ile Ser Ile Met Val Leu Ile Cys Leu Asn Met Val Thr
1505                1510                1515                1520

Met Met Val Glu Lys Glu Gly Gln Ser Gln His Met Thr Glu Val Leu
                1525                1530                1535

Tyr Trp Ile Asn Val Val Phe Ile Ile Leu Phe Thr Gly Glu Cys Val
            1540                1545                1550

Leu Lys Leu Ile Ser Leu Arg His Tyr Tyr Phe Thr Val Gly Trp Asn
            1555                1560                1565

Ile Phe Asp Phe Val Val Val Ile Ile Ser Ile Val Gly Met Phe Leu
        1570                1575                1580

Ala Asp Leu Ile Glu Thr Tyr Phe Val Ser Pro Thr Leu Phe Arg Val
1585                1590                1595                1600

Ile Arg Leu Ala Arg Ile Gly Arg Ile Leu Arg Leu Val Lys Gly Ala
        1605                1610                1615

Lys Gly Ile Arg Thr Leu Leu Phe Ala Leu Met Met Ser Leu Pro Ala
        1620                1625                1630

Leu Phe Asn Ile Gly Leu Leu Leu Phe Leu Val Met Phe Ile Tyr Ala
        1635                1640                1645

Ile Phe Gly Met Ser Asn Phe Ala Tyr Val Lys Lys Glu Asp Gly Ile
        1650                1655                1660

Asn Asp Met Phe Asn Phe Glu Thr Phe Gly Asn Ser Met Ile Cys Leu
1665                1670                1675                1680

Phe Gln Ile Thr Thr Ser Ala Gly Trp Asp Gly Leu Leu Ala Pro Ile
            1685                1690                1695

Leu Asn Ser Lys Pro Pro Asp Cys Asp Pro Lys Lys Val His Pro Gly
            1700                1705                1710

Ser Ser Val Glu Gly Asp Cys Gly Asn Pro Ser Val Gly Ile Phe Tyr
            1715                1720                1725

Phe Val Ser Tyr Ile Ile Ile Ser Phe Leu Val Val Val Asn Met Tyr
        1730                1735                1740

Ile Ala Val Ile Leu Glu Asn Phe Ser Val Ala Thr Glu Glu Ser Thr
1745                1750                1755                1760

Glu Pro Leu Ser Glu Asp Asp Phe Glu Met Phe Tyr Glu Val Trp Glu
        1765                1770                1775

Lys Phe Asp Pro Asp Ala Thr Gln Phe Ile Glu Phe Ser Lys Leu Ser
        1780                1785                1790

Asp Phe Ala Ala Ala Leu Asp Pro Pro Leu Leu Ile Ala Lys Pro Asn
        1795                1800                1805

Lys Val Gln Leu Ile Ala Met Asp Leu Pro Met Val Ser Gly Asp Arg
        1810                1815                1820

Ile His Cys Leu Asp Ile Leu Phe Ala Phe Thr Lys Arg Val Leu Gly
        1825                1830                1835                1840

Glu Ser Gly Glu Met Asp Ser Leu Arg Ser Gln Met Glu Glu Arg Phe
            1845                1850                1855

Met Ser Ala Asn Pro Ser Lys Val Ser Tyr Glu Pro Ile Thr Thr Thr
            1860                1865                1870

Leu Lys Arg Lys Gln Glu Asp Val Ser Ala Thr Val Ile Gln Arg Ala
        1875                1880                1885

Tyr Arg Arg Tyr Arg Leu Arg Gln Asn Val Lys Asn Ile Ser Ser Ile
```

```
                1890                1895                1900
Tyr Ile Lys Asp Gly Asp Arg Asp Asp Leu Leu Asn Lys Lys Asp
1905                1910                1915                1920

Met Ala Phe Asp Asn Val Asn Glu Asn Ser Ser Pro Glu Lys Thr Asp
                1925                1930                1935

Ala Thr Ser Ser Thr Thr Ser Pro Pro Ser Tyr Asp Ser Val Thr Lys
            1940                1945                1950

Pro Asp Lys Glu Lys Tyr Glu Gln Asp Arg Thr Glu Lys Glu Asp Lys
            1955                1960                1965

Gly Lys Asp Ser Lys Glu Ser Lys Lys
            1970                1975

<210> SEQ ID NO 6
<211> LENGTH: 1977
<212> TYPE: PRT
<213> ORGANISM: Homo Sapien

<400> SEQUENCE: 6

Met Ala Met Leu Pro Pro Gly Pro Gln Ser Phe Val His Phe Thr
1               5                   10                  15

Lys Gln Ser Leu Ala Leu Ile Glu Gln Arg Ile Ala Glu Arg Lys Ser
                20                  25                  30

Lys Glu Pro Lys Glu Glu Lys Lys Asp Asp Asp Glu Glu Ala Pro Lys
            35                  40                  45

Pro Ser Ser Asp Leu Glu Ala Gly Lys Gln Leu Pro Phe Ile Tyr Gly
50                  55                  60

Asp Ile Pro Pro Gly Met Val Ser Glu Pro Leu Glu Asp Leu Asp Pro
65                  70                  75                  80

Tyr Tyr Ala Asp Lys Lys Thr Phe Ile Val Leu Asn Lys Gly Lys Thr
                85                  90                  95

Ile Phe Arg Phe Asn Ala Thr Pro Ala Leu Tyr Met Leu Ser Pro Phe
            100                 105                 110

Ser Pro Leu Arg Arg Ile Ser Ile Lys Ile Leu Val His Ser Leu Phe
        115                 120                 125

Ser Met Leu Ile Met Cys Thr Ile Leu Thr Asn Cys Ile Phe Met Thr
130                 135                 140

Met Asn Asn Pro Pro Asp Trp Thr Lys Asn Val Glu Tyr Thr Phe Thr
145                 150                 155                 160

Gly Ile Tyr Thr Phe Glu Ser Leu Val Lys Ile Leu Ala Arg Gly Phe
                165                 170                 175

Cys Val Gly Glu Phe Thr Phe Leu Arg Asp Pro Trp Asn Trp Leu Asp
            180                 185                 190

Phe Val Val Ile Val Phe Ala Tyr Leu Thr Glu Phe Val Asn Leu Gly
        195                 200                 205

Asn Val Ser Ala Leu Arg Thr Phe Arg Val Leu Arg Ala Leu Lys Thr
210                 215                 220

Ile Ser Val Ile Pro Gly Leu Lys Thr Ile Val Gly Ala Leu Ile Gln
225                 230                 235                 240

Ser Val Lys Lys Leu Ser Asp Val Met Ile Leu Thr Val Phe Cys Leu
                245                 250                 255

Ser Val Phe Ala Leu Ile Gly Leu Gln Leu Phe Met Gly Asn Leu Lys
            260                 265                 270

His Lys Cys Phe Arg Asn Ser Leu Glu Asn Asn Glu Thr Leu Glu Ser
        275                 280                 285
```

-continued

```
Ile Met Asn Thr Leu Glu Ser Glu Glu Asp Phe Arg Lys Tyr Phe Tyr
290                 295                 300
Tyr Leu Glu Gly Ser Lys Asp Ala Leu Leu Cys Gly Phe Ser Thr Asp
305                 310                 315                 320
Ser Gly Gln Cys Pro Glu Gly Tyr Thr Cys Val Lys Ile Gly Arg Asn
                325                 330                 335
Pro Asp Tyr Gly Tyr Thr Ser Phe Asp Thr Phe Ser Trp Ala Phe Leu
                340                 345                 350
Ala Leu Phe Arg Leu Met Thr Gln Asp Tyr Trp Glu Asn Leu Tyr Gln
                355                 360                 365
Gln Thr Leu Arg Ala Ala Gly Lys Thr Tyr Met Ile Phe Phe Val Val
370                 375                 380
Val Ile Phe Leu Gly Ser Phe Tyr Leu Ile Asn Leu Ile Leu Ala Val
385                 390                 395                 400
Val Ala Met Ala Tyr Glu Glu Gln Asn Gln Ala Asn Ile Glu Glu Ala
                405                 410                 415
Lys Gln Lys Glu Leu Glu Phe Gln Gln Met Leu Asp Arg Leu Lys Lys
                420                 425                 430
Glu Gln Glu Glu Ala Glu Ala Ile Ala Ala Ala Ala Ala Glu Tyr Thr
                435                 440                 445
Ser Ile Arg Arg Ser Arg Ile Met Gly Leu Ser Glu Ser Ser Ser Glu
450                 455                 460
Thr Ser Lys Leu Ser Ser Lys Ser Ala Lys Glu Arg Arg Asn Arg Arg
465                 470                 475                 480
Lys Lys Lys Asn Gln Lys Lys Leu Ser Ser Gly Glu Glu Lys Gly Asp
                485                 490                 495
Ala Glu Lys Leu Ser Lys Ser Glu Ser Glu Asp Ser Ile Arg Arg Lys
                500                 505                 510
Ser Phe His Leu Gly Val Glu Gly His Arg Arg Ala His Glu Lys Arg
                515                 520                 525
Leu Ser Thr Pro Asn Gln Ser Pro Leu Ser Ile Arg Gly Ser Leu Phe
530                 535                 540
Ser Ala Arg Arg Ser Ser Arg Thr Ser Leu Phe Ser Phe Lys Gly Arg
545                 550                 555                 560
Gly Arg Asp Ile Gly Ser Glu Thr Glu Phe Ala Asp Asp Glu His Ser
                565                 570                 575
Ile Phe Gly Asp Asn Glu Ser Arg Arg Gly Ser Leu Phe Val Pro His
                580                 585                 590
Arg Pro Gln Glu Arg Arg Ser Ser Asn Ile Ser Gln Ala Ser Arg Ser
                595                 600                 605
Pro Pro Met Leu Pro Val Asn Gly Lys Met His Ser Ala Val Asp Cys
610                 615                 620
Asn Gly Val Val Ser Leu Val Asp Gly Arg Ser Ala Leu Met Leu Pro
625                 630                 635                 640
Asn Gly Gln Leu Leu Pro Glu Gly Thr Thr Asn Gln Ile His Lys Lys
                645                 650                 655
Arg Arg Cys Ser Ser Tyr Leu Leu Ser Glu Asp Met Leu Asn Asp Pro
                660                 665                 670
Asn Leu Arg Gln Arg Ala Met Ser Arg Ala Ser Ile Leu Thr Asn Thr
                675                 680                 685
Val Glu Glu Leu Glu Glu Ser Arg Gln Lys Cys Pro Pro Trp Trp Tyr
690                 695                 700
Arg Phe Ala His Lys Phe Leu Ile Trp Asn Cys Ser Pro Tyr Trp Ile
```

-continued

```
            705                 710                 715                 720
Lys Phe Lys Lys Cys Ile Tyr Phe Ile Val Met Asp Pro Phe Val Asp
                    725                 730                 735
Leu Ala Val Thr Ile Cys Ile Val Leu Asn Thr Leu Phe Met Ala Met
                740                 745                 750
Glu His His Pro Met Thr Glu Phe Lys Asn Val Leu Ala Ile Gly
            755                 760                 765
Asn Leu Val Phe Thr Gly Ile Phe Ala Ala Glu Met Val Leu Lys Leu
            770                 775                 780
Ile Ala Met Asp Pro Tyr Glu Tyr Phe Gln Val Gly Trp Asn Ile Phe
785                 790                 795                 800
Asp Ser Leu Ile Val Thr Leu Ser Leu Val Glu Leu Phe Leu Ala Asp
                805                 810                 815
Val Glu Gly Leu Ser Val Leu Arg Ser Phe Arg Leu Leu Arg Val Phe
                820                 825                 830
Lys Leu Ala Lys Ser Trp Pro Thr Leu Asn Met Leu Ile Lys Ile Ile
                835                 840                 845
Gly Asn Ser Val Gly Ala Leu Gly Asn Leu Thr Leu Val Leu Ala Ile
            850                 855                 860
Ile Val Phe Ile Phe Ala Val Val Gly Met Gln Leu Phe Gly Lys Ser
865                 870                 875                 880
Tyr Lys Glu Cys Val Cys Lys Ile Asn Asp Asp Cys Thr Leu Pro Arg
                885                 890                 895
Trp His Met Asn Asp Phe Phe His Ser Phe Leu Ile Val Phe Arg Val
                900                 905                 910
Leu Cys Gly Glu Trp Ile Glu Thr Met Trp Asp Cys Met Glu Val Ala
                915                 920                 925
Gly Gln Ala Met Cys Leu Ile Val Tyr Met Met Val Met Val Ile Gly
            930                 935                 940
Asn Leu Val Val Leu Asn Leu Phe Leu Ala Leu Leu Leu Ser Ser Phe
945                 950                 955                 960
Ser Ser Asp Asn Leu Thr Ala Ile Glu Glu Asp Pro Asp Ala Asn Asn
                965                 970                 975
Leu Gln Ile Ala Val Thr Arg Ile Lys Lys Gly Ile Asn Tyr Val Lys
            980                 985                 990
Gln Thr Leu Arg Glu Phe Ile Leu Lys Ala Phe Ser Lys Lys Pro Lys
            995                 1000                1005
Ile Ser Arg Glu Ile Arg Gln Ala Glu Asp Leu Asn Thr Lys Lys Glu
            1010                1015                1020
Asn Tyr Ile Ser Asn His Thr Leu Ala Glu Met Ser Lys Gly His Asn
1025                1030                1035                1040
Phe Leu Lys Glu Lys Asp Lys Ile Ser Gly Phe Gly Ser Ser Val Asp
                1045                1050                1055
Lys His Leu Met Glu Asp Ser Asp Gly Gln Ser Phe Ile His Asn Pro
            1060                1065                1070
Ser Leu Thr Val Thr Val Pro Ile Ala Pro Gly Glu Ser Asp Leu Glu
            1075                1080                1085
Asn Met Asn Ala Glu Glu Leu Ser Ser Asp Ser Asp Ser Glu Tyr Ser
            1090                1095                1100
Lys Val Arg Leu Asn Arg Ser Ser Ser Ser Glu Cys Ser Thr Val Asp
1105                1110                1115                1120
Asn Pro Leu Pro Gly Glu Gly Glu Glu Ala Glu Ala Glu Pro Met Asn
                1125                1130                1135
```

-continued

```
Ser Asp Glu Pro Glu Ala Cys Phe Thr Asp Gly Cys Val Arg Arg Phe
            1140                1145                1150

Ser Cys Cys Gln Val Asn Ile Glu Ser Gly Lys Gly Lys Ile Trp Trp
            1155                1160                1165

Asn Ile Arg Lys Thr Cys Tyr Lys Ile Val Glu His Ser Trp Phe Glu
            1170                1175                1180

Ser Phe Ile Val Leu Met Ile Leu Leu Ser Ser Gly Ala Leu Ala Phe
1185                1190                1195                1200

Glu Asp Ile Tyr Ile Glu Arg Lys Lys Thr Ile Lys Ile Ile Leu Glu
                1205                1210                1215

Tyr Ala Asp Lys Ile Phe Thr Tyr Ile Phe Ile Leu Glu Met Leu Leu
                1220                1225                1230

Lys Trp Ile Ala Tyr Gly Tyr Lys Thr Tyr Phe Thr Asn Ala Trp Cys
                1235                1240                1245

Trp Leu Asp Phe Leu Ile Val Asp Val Ser Leu Val Thr Leu Val Ala
                1250                1255                1260

Asn Thr Leu Gly Tyr Ser Asp Leu Gly Pro Ile Lys Ser Leu Arg Thr
1265                1270                1275                1280

Leu Arg Ala Leu Arg Pro Leu Arg Ala Leu Ser Arg Phe Glu Gly Met
                1285                1290                1295

Arg Val Val Val Asn Ala Leu Ile Gly Ala Ile Pro Ser Ile Met Asn
                1300                1305                1310

Val Leu Leu Val Cys Leu Ile Phe Trp Leu Ile Phe Ser Ile Met Gly
                1315                1320                1325

Val Asn Leu Phe Ala Gly Lys Phe Tyr Glu Cys Ile Asn Thr Thr Asp
                1330                1335                1340

Gly Ser Arg Phe Pro Ala Ser Gln Val Pro Asn Arg Ser Glu Cys Phe
1345                1350                1355                1360

Ala Leu Met Asn Val Ser Gln Asn Val Arg Trp Lys Asn Leu Lys Val
                1365                1370                1375

Asn Phe Asp Asn Val Gly Leu Gly Tyr Leu Ser Leu Leu Gln Val Ala
                1380                1385                1390

Thr Phe Lys Gly Trp Thr Ile Ile Met Tyr Ala Ala Val Asp Ser Val
                1395                1400                1405

Asn Val Asp Lys Gln Pro Lys Tyr Glu Tyr Ser Leu Tyr Met Tyr Ile
                1410                1415                1420

Tyr Phe Val Val Phe Ile Ile Phe Gly Ser Phe Phe Thr Leu Asn Leu
1425                1430                1435                1440

Phe Ile Gly Val Ile Ile Asp Asn Phe Asn Gln Gln Lys Lys Lys Leu
                1445                1450                1455

Gly Gly Gln Asp Ile Phe Met Thr Glu Glu Gln Lys Lys Tyr Tyr Asn
                1460                1465                1470

Ala Met Lys Lys Leu Gly Ser Lys Lys Pro Gln Lys Pro Ile Pro Arg
                1475                1480                1485

Pro Gly Asn Lys Ile Gln Gly Cys Ile Phe Asp Leu Val Thr Asn Gln
                1490                1495                1500

Ala Phe Asp Ile Ser Ile Met Val Leu Ile Cys Leu Asn Met Val Thr
1505                1510                1515                1520

Met Met Val Glu Lys Glu Gly Gln Ser Gln His Met Thr Glu Val Leu
                1525                1530                1535

Tyr Trp Ile Asn Val Val Phe Ile Ile Leu Phe Thr Gly Glu Cys Val
                1540                1545                1550
```

```
Leu Lys Leu Ile Ser Leu Arg His Tyr Tyr Phe Thr Val Gly Trp Asn
        1555                1560                1565

Ile Phe Asp Phe Val Val Ile Ser Ile Val Gly Met Phe Leu
    1570                1575                1580

Ala Asp Leu Ile Glu Thr Tyr Phe Val Ser Pro Thr Leu Phe Arg Val
1585                1590                1595                1600

Ile Arg Leu Ala Arg Ile Gly Arg Ile Leu Arg Leu Val Lys Gly Ala
            1605                1610                1615

Lys Gly Ile Arg Thr Leu Leu Phe Ala Leu Met Met Ser Leu Pro Ala
        1620                1625                1630

Leu Phe Asn Ile Gly Leu Leu Leu Phe Leu Val Met Phe Ile Tyr Ala
    1635                1640                1645

Ile Phe Gly Met Ser Asn Phe Ala Tyr Val Lys Lys Glu Asp Gly Ile
    1650                1655                1660

Asn Asp Met Phe Asn Phe Glu Thr Phe Gly Asn Ser Met Ile Cys Leu
1665                1670                1675                1680

Phe Gln Ile Thr Thr Ser Ala Gly Trp Asp Gly Leu Leu Ala Pro Ile
            1685                1690                1695

Leu Asn Ser Lys Pro Pro Asp Cys Asp Pro Lys Lys Val His Pro Gly
        1700                1705                1710

Ser Ser Val Glu Gly Asp Cys Gly Asn Pro Ser Val Gly Ile Phe Tyr
    1715                1720                1725

Phe Val Ser Tyr Ile Ile Ile Ser Phe Leu Val Val Val Asn Met Tyr
    1730                1735                1740

Ile Ala Val Ile Leu Glu Asn Phe Ser Val Ala Thr Glu Glu Ser Thr
1745                1750                1755                1760

Glu Pro Leu Ser Glu Asp Asp Phe Glu Met Phe Tyr Glu Val Trp Glu
            1765                1770                1775

Lys Phe Asp Pro Asp Ala Thr Gln Phe Ile Glu Phe Ser Lys Leu Ser
        1780                1785                1790

Asp Phe Ala Ala Ala Leu Asp Pro Pro Leu Leu Ile Ala Lys Pro Asn
    1795                1800                1805

Lys Val Gln Leu Ile Ala Met Asp Leu Pro Met Val Ser Gly Asp Arg
    1810                1815                1820

Ile His Cys Leu Asp Ile Leu Phe Ala Phe Thr Lys Arg Val Leu Gly
1825                1830                1835                1840

Glu Ser Gly Glu Met Asp Ser Leu Arg Ser Gln Met Glu Glu Arg Phe
            1845                1850                1855

Met Ser Ala Asn Pro Ser Lys Val Ser Tyr Glu Pro Ile Thr Thr Thr
        1860                1865                1870

Leu Lys Arg Lys Gln Glu Asp Val Ser Ala Thr Val Ile Gln Arg Ala
    1875                1880                1885

Tyr Arg Arg Tyr Arg Leu Arg Gln Asn Val Lys Asn Ile Ser Ser Ile
    1890                1895                1900

Tyr Ile Lys Asp Gly Asp Arg Asp Asp Leu Leu Asn Lys Lys Asp
1905                1910                1915                1920

Met Ala Phe Asp Asn Val Asn Glu Asn Ser Ser Pro Glu Lys Thr Asp
            1925                1930                1935

Ala Thr Ser Ser Thr Thr Ser Pro Pro Ser Tyr Asp Ser Val Thr Lys
        1940                1945                1950

Pro Asp Lys Glu Lys Tyr Glu Gln Asp Arg Thr Glu Lys Glu Asp Lys
    1955                1960                1965

Gly Lys Asp Ser Lys Glu Ser Lys Lys
```

<210> SEQ ID NO 7
<211> LENGTH: 1977
<212> TYPE: PRT
<213> ORGANISM: Homo Sapien

<400> SEQUENCE: 7

```
Met Ala Met Leu Pro Pro Gly Pro Gln Ser Phe Val His Phe Thr
 1               5                  10                  15

Lys Gln Ser Leu Ala Leu Ile Glu Gln Arg Ile Ala Glu Arg Lys Ser
                20                  25                  30

Lys Glu Pro Lys Glu Glu Lys Lys Asp Asp Asp Glu Glu Ala Pro Lys
                35                  40                  45

Pro Ser Ser Asp Leu Glu Ala Gly Lys Gln Leu Pro Phe Ile Tyr Gly
        50                  55                  60

Asp Ile Pro Pro Gly Met Val Ser Glu Pro Leu Glu Asp Leu Asp Pro
65                  70                  75                  80

Tyr Tyr Ala Asp Lys Lys Thr Phe Ile Val Leu Asn Lys Gly Lys Thr
                85                  90                  95

Ile Phe Arg Phe Asn Ala Thr Pro Ala Leu Tyr Met Leu Ser Pro Phe
                100                 105                 110

Ser Pro Leu Arg Arg Ile Ser Ile Lys Ile Leu Val His Ser Leu Phe
            115                 120                 125

Ser Met Leu Ile Met Cys Thr Ile Leu Thr Asn Cys Ile Phe Met Thr
        130                 135                 140

Met Asn Asn Pro Pro Asp Trp Thr Lys Asn Val Glu Tyr Thr Phe Thr
145                 150                 155                 160

Gly Ile Tyr Thr Phe Glu Ser Leu Val Lys Ile Leu Ala Arg Gly Phe
                165                 170                 175

Cys Val Gly Glu Phe Thr Phe Leu Arg Asp Pro Trp Asn Trp Leu Asp
            180                 185                 190

Phe Val Val Ile Val Phe Ala Tyr Leu Thr Glu Phe Val Asn Leu Gly
        195                 200                 205

Asn Val Ser Ala Leu Arg Thr Phe Arg Val Leu Arg Ala Leu Lys Thr
210                 215                 220

Ile Ser Val Ile Pro Gly Leu Lys Thr Ile Val Gly Ala Leu Ile Gln
225                 230                 235                 240

Ser Val Lys Lys Leu Ser Asp Val Met Ile Leu Thr Val Phe Cys Leu
                245                 250                 255

Ser Val Phe Ala Leu Ile Gly Leu Gln Leu Phe Met Gly Asn Leu Lys
                260                 265                 270

His Lys Cys Phe Arg Asn Ser Leu Glu Asn Asn Glu Thr Leu Glu Ser
            275                 280                 285

Ile Met Asn Thr Leu Glu Ser Glu Glu Asp Phe Arg Lys Tyr Phe Tyr
        290                 295                 300

Tyr Leu Glu Gly Ser Lys Asp Ala Leu Leu Cys Gly Phe Ser Thr Asp
305                 310                 315                 320

Ser Gly Gln Cys Pro Glu Gly Tyr Thr Cys Val Lys Ile Gly Arg Asn
                325                 330                 335

Pro Asp Tyr Gly Tyr Thr Ser Phe Asp Thr Phe Ser Trp Ala Phe Leu
                340                 345                 350

Ala Leu Phe Arg Leu Met Thr Gln Asp Tyr Trp Glu Asn Leu Tyr Gln
            355                 360                 365
```

```
Gln Thr Leu Arg Ala Ala Gly Lys Thr Tyr Met Ile Phe Val Val
    370                 375                 380

Val Ile Phe Leu Gly Ser Phe Tyr Leu Ile Asn Leu Ile Leu Ala Val
385                 390                 395                 400

Val Ala Met Ala Tyr Glu Glu Gln Asn Gln Ala Asn Ile Glu Glu Ala
                405                 410                 415

Lys Gln Lys Glu Leu Glu Phe Gln Gln Met Leu Asp Arg Leu Lys Lys
            420                 425                 430

Glu Gln Glu Glu Ala Glu Ala Ile Ala Ala Ala Ala Glu Tyr Thr
        435                 440                 445

Ser Ile Arg Arg Ser Arg Ile Met Gly Leu Ser Glu Ser Ser Ser Glu
    450                 455                 460

Thr Ser Lys Leu Ser Ser Lys Ser Ala Lys Glu Arg Arg Asn Arg Arg
465                 470                 475                 480

Lys Lys Lys Asn Gln Lys Lys Leu Ser Ser Gly Glu Glu Lys Gly Asp
                485                 490                 495

Ala Glu Lys Leu Ser Lys Ser Glu Ser Glu Asp Ser Ile Arg Arg Lys
            500                 505                 510

Ser Phe His Leu Gly Val Glu Gly His Arg Arg Ala His Glu Lys Arg
    515                 520                 525

Leu Ser Thr Pro Asn Gln Ser Pro Leu Ser Ile Arg Gly Ser Leu Phe
    530                 535                 540

Ser Ala Arg Arg Ser Ser Arg Thr Ser Leu Phe Ser Phe Lys Gly Arg
545                 550                 555                 560

Gly Arg Asp Ile Gly Ser Glu Thr Glu Phe Ala Asp Asp Glu His Ser
                565                 570                 575

Ile Phe Gly Asp Asn Glu Ser Arg Arg Gly Ser Leu Phe Val Pro His
            580                 585                 590

Arg Pro Gln Glu Arg Arg Ser Ser Asn Ile Ser Gln Ala Ser Arg Ser
        595                 600                 605

Pro Pro Met Leu Pro Val Asn Gly Lys Met His Ser Ala Val Asp Cys
    610                 615                 620

Asn Gly Val Val Ser Leu Val Asp Gly Arg Ser Ala Leu Met Leu Pro
625                 630                 635                 640

Asn Gly Gln Leu Leu Pro Glu Gly Thr Thr Asn Gln Ile His Lys Lys
                645                 650                 655

Arg Arg Cys Ser Ser Tyr Leu Leu Ser Glu Asp Met Leu Asn Asp Pro
            660                 665                 670

Asn Leu Arg Gln Arg Ala Met Ser Arg Ala Ser Ile Leu Thr Asn Thr
        675                 680                 685

Val Glu Glu Leu Glu Glu Ser Arg Gln Lys Cys Pro Pro Trp Trp Tyr
    690                 695                 700

Arg Phe Ala His Lys Phe Leu Ile Trp Asn Cys Ser Pro Tyr Trp Ile
705                 710                 715                 720

Lys Phe Lys Lys Cys Ile Tyr Phe Ile Val Met Asp Pro Phe Val Asp
                725                 730                 735

Leu Ala Ile Thr Ile Cys Ile Val Leu Asn Thr Leu Phe Met Ala Met
            740                 745                 750

Glu His His Pro Met Thr Glu Glu Phe Lys Asn Val Leu Ala Ile Gly
        755                 760                 765

Asn Leu Val Phe Thr Gly Ile Phe Ala Ala Glu Met Val Leu Lys Leu
    770                 775                 780

Ile Ala Met Asp Pro Tyr Glu Tyr Phe Gln Val Gly Trp Asn Ile Phe
```

-continued

```
              785                 790                 795                 800
Asp Ser Leu Ile Val Thr Leu Ser Leu Val Glu Leu Phe Leu Ala Asp
                    805                 810                 815
Val Glu Gly Leu Ser Val Leu Arg Ser Phe Arg Leu Leu Arg Val Phe
                820                 825                 830
Lys Leu Ala Lys Ser Trp Pro Thr Leu Asn Met Leu Ile Lys Ile Ile
                835                 840                 845
Gly Asn Ser Val Gly Ala Leu Gly Asn Leu Thr Leu Val Leu Ala Ile
                850                 855                 860
Ile Val Phe Ile Phe Ala Val Val Gly Met Gln Leu Phe Gly Lys Ser
865                 870                 875                 880
Tyr Lys Glu Cys Val Cys Lys Ile Asn Asp Asp Cys Thr Leu Pro Arg
                    885                 890                 895
Trp His Met Asn Asp Phe Phe His Ser Phe Leu Ile Val Phe Arg Val
                    900                 905                 910
Leu Cys Gly Glu Trp Ile Glu Thr Met Trp Asp Cys Met Glu Val Ala
                915                 920                 925
Gly Gln Ala Met Cys Leu Ile Val Tyr Met Met Val Met Val Ile Gly
                930                 935                 940
Asn Leu Val Val Leu Asn Leu Phe Leu Ala Leu Leu Leu Ser Ser Phe
945                 950                 955                 960
Ser Ser Asp Asn Leu Thr Ala Ile Glu Glu Asp Pro Asp Ala Asn Asn
                    965                 970                 975
Leu Gln Ile Ala Val Thr Arg Ile Lys Lys Gly Ile Asn Tyr Val Lys
                980                 985                 990
Gln Thr Leu Arg Glu Phe Ile Leu Lys Ala Phe Ser Lys Lys Pro Lys
                995                 1000                1005
Ile Ser Arg Glu Ile Arg Gln Ala Glu Asp Leu Asn Thr Lys Lys Glu
                1010                1015                1020
Asn Tyr Ile Ser Asn His Thr Leu Ala Glu Met Ser Lys Gly His Asn
1025                1030                1035                1040
Phe Leu Lys Glu Lys Asp Lys Ile Ser Gly Phe Gly Ser Ser Val Asp
                    1045                1050                1055
Lys His Leu Met Glu Asp Ser Asp Gly Gln Ser Phe Ile His Asn Pro
                    1060                1065                1070
Ser Leu Thr Val Thr Val Pro Ile Ala Pro Gly Glu Ser Asp Leu Glu
                1075                1080                1085
Asn Met Asn Ala Glu Glu Leu Ser Ser Asp Ser Asp Ser Glu Tyr Ser
                1090                1095                1100
Lys Val Arg Leu Asn Arg Ser Ser Ser Ser Glu Cys Ser Thr Val Asp
1105                1110                1115                1120
Asn Pro Phe Pro Gly Glu Gly Glu Glu Ala Glu Ala Glu Pro Met Asn
                    1125                1130                1135
Ser Asp Glu Pro Glu Ala Cys Phe Thr Asp Gly Cys Val Arg Arg Phe
                    1140                1145                1150
Ser Cys Cys Gln Val Asn Ile Glu Ser Gly Lys Gly Lys Ile Trp Trp
                1155                1160                1165
Asn Ile Arg Lys Thr Cys Tyr Lys Ile Val Glu His Ser Trp Phe Glu
                1170                1175                1180
Ser Phe Ile Val Leu Met Ile Leu Leu Ser Ser Gly Ala Leu Ala Phe
1185                1190                1195                1200
Glu Asp Ile Tyr Ile Glu Arg Lys Lys Thr Ile Lys Ile Ile Leu Glu
                1205                1210                1215
```

-continued

```
Tyr Ala Asp Lys Ile Phe Thr Tyr Ile Phe Ile Leu Glu Met Leu Leu
            1220                1225                1230

Lys Trp Ile Ala Tyr Gly Tyr Lys Thr Tyr Phe Thr Asn Ala Trp Cys
        1235                1240                1245

Trp Leu Asp Phe Leu Ile Val Asp Val Ser Leu Val Thr Leu Val Ala
        1250                1255                1260

Asn Thr Leu Gly Tyr Ser Asp Leu Gly Pro Ile Lys Ser Leu Arg Thr
1265                1270                1275                1280

Leu Arg Ala Leu Arg Pro Leu Arg Ala Leu Ser Arg Phe Glu Gly Met
            1285                1290                1295

Arg Val Val Val Asn Ala Leu Ile Gly Ala Ile Pro Ser Ile Met Asn
            1300                1305                1310

Val Leu Leu Val Cys Leu Ile Phe Trp Leu Ile Phe Ser Ile Met Gly
            1315                1320                1325

Val Asn Leu Phe Ala Gly Lys Phe Tyr Glu Cys Ile Asn Thr Thr Asp
            1330                1335                1340

Gly Ser Arg Phe Pro Ala Ser Gln Val Pro Asn Arg Ser Glu Cys Phe
1345                1350                1355                1360

Ala Leu Met Asn Val Ser Gln Asn Val Arg Trp Lys Asn Leu Lys Val
            1365                1370                1375

Asn Phe Asp Asn Val Gly Leu Gly Tyr Leu Ser Leu Leu Gln Val Ala
            1380                1385                1390

Thr Phe Lys Gly Trp Thr Ile Ile Met Tyr Ala Ala Val Asp Ser Val
            1395                1400                1405

Asn Val Asp Lys Gln Pro Lys Tyr Glu Tyr Ser Leu Tyr Met Tyr Ile
        1410                1415                1420

Tyr Phe Val Val Phe Ile Ile Phe Gly Ser Phe Phe Thr Leu Asn Leu
1425                1430                1435                1440

Phe Ile Gly Val Ile Ile Asp Asn Phe Asn Gln Gln Lys Lys Lys Leu
            1445                1450                1455

Gly Gly Gln Asp Ile Phe Met Thr Glu Glu Gln Lys Lys Tyr Tyr Asn
            1460                1465                1470

Ala Met Lys Lys Leu Gly Ser Lys Lys Pro Gln Lys Pro Ile Pro Arg
        1475                1480                1485

Pro Gly Asn Lys Ile Gln Gly Cys Ile Phe Asp Leu Val Thr Asn Gln
        1490                1495                1500

Ala Phe Asp Ile Ser Ile Met Val Leu Ile Cys Leu Asn Met Val Thr
1505                1510                1515                1520

Met Met Val Glu Lys Glu Gly Gln Ser Gln His Met Thr Glu Val Leu
            1525                1530                1535

Tyr Trp Ile Asn Val Val Phe Ile Ile Leu Phe Thr Gly Glu Cys Val
            1540                1545                1550

Leu Lys Leu Ile Ser Leu Arg His Tyr Tyr Phe Thr Val Gly Trp Asn
        1555                1560                1565

Ile Phe Asp Phe Val Val Val Ile Ile Ser Ile Val Gly Met Phe Leu
        1570                1575                1580

Ala Asp Leu Ile Glu Thr Tyr Phe Val Ser Pro Thr Leu Phe Arg Val
1585                1590                1595                1600

Ile Arg Leu Ala Arg Ile Gly Arg Ile Leu Arg Leu Val Lys Gly Ala
            1605                1610                1615

Lys Gly Ile Arg Thr Leu Leu Phe Ala Leu Met Met Ser Leu Pro Ala
            1620                1625                1630
```

```
Leu Phe Asn Ile Gly Leu Leu Leu Phe Leu Val Met Phe Ile Tyr Ala
        1635                1640                1645

Ile Phe Gly Met Ser Asn Phe Ala Tyr Val Lys Lys Glu Asp Gly Ile
    1650                1655                1660

Asn Asp Met Phe Asn Phe Glu Thr Phe Gly Asn Ser Met Ile Cys Leu
1665                1670                1675                1680

Phe Gln Ile Thr Thr Ser Ala Gly Trp Asp Gly Leu Leu Ala Pro Ile
            1685                1690                1695

Leu Asn Ser Lys Pro Pro Asp Cys Asp Pro Lys Lys Val His Pro Gly
        1700                1705                1710

Ser Ser Val Glu Gly Asp Cys Gly Asn Pro Ser Val Gly Ile Phe Tyr
    1715                1720                1725

Phe Val Ser Tyr Ile Ile Ile Ser Phe Leu Val Val Val Asn Met Tyr
1730                1735                1740

Ile Ala Val Ile Leu Glu Asn Phe Ser Val Ala Thr Glu Glu Ser Thr
1745                1750                1755                1760

Glu Pro Leu Ser Glu Asp Asp Phe Glu Met Phe Tyr Glu Val Trp Glu
            1765                1770                1775

Lys Phe Asp Pro Asp Ala Thr Gln Phe Ile Glu Phe Ser Lys Leu Ser
        1780                1785                1790

Asp Phe Ala Ala Ala Leu Asp Pro Pro Leu Leu Ile Ala Lys Pro Asn
    1795                1800                1805

Lys Val Gln Leu Ile Ala Met Asp Leu Pro Met Val Ser Gly Asp Arg
1810                1815                1820

Ile His Cys Leu Asp Ile Leu Phe Ala Phe Thr Lys Arg Val Leu Gly
1825                1830                1835                1840

Glu Ser Gly Glu Met Asp Ser Leu Arg Ser Gln Met Glu Glu Arg Phe
            1845                1850                1855

Met Ser Ala Asn Pro Ser Lys Val Ser Tyr Glu Pro Ile Thr Thr Thr
        1860                1865                1870

Leu Lys Arg Lys Gln Glu Asp Val Ser Ala Thr Val Ile Gln Arg Ala
    1875                1880                1885

Tyr Arg Arg Tyr Arg Leu Arg Gln Asn Val Lys Asn Ile Ser Ser Ile
    1890                1895                1900

Tyr Ile Lys Asp Gly Asp Arg Asp Asp Leu Leu Asn Lys Lys Asp
1905                1910                1915                1920

Met Ala Phe Asp Asn Val Asn Glu Asn Ser Pro Glu Lys Thr Asp
            1925                1930                1935

Ala Thr Ser Ser Thr Thr Ser Pro Pro Ser Tyr Asp Ser Val Thr Lys
        1940                1945                1950

Pro Asp Lys Glu Lys Tyr Glu Gln Asp Arg Thr Glu Lys Glu Asp Lys
    1955                1960                1965

Gly Lys Asp Ser Lys Glu Ser Lys Lys
    1970                1975

<210> SEQ ID NO 8
<211> LENGTH: 5934
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 8
atggcaatgt tgcctccccc aggacctcag agctttgtcc atttcacaaa acagtctctt      60
```

```
gccctcattg aacaacgcat tgctgaaaga aaatcaaagg aacccaaaga agaaaagaaa    120
gatgatgatg aagaagcccc aaagccaagc agtgacttgg aagctggcaa acaactgccc    180
ttcgtctatg gggacattcc tcccggcatg gtgtcagagc ccctggagga cttggacccc    240
tactatgcag acaaaaagac tttcatagta ttgaacaaag ggaaaacaat cttccgtttc    300
aatgccacac ctgctttata tatgctttct cctttcagtc ctctaagaag aatatctatt    360
aagattttag tacactcctt attcagcatg ctcatcatgt gcactattct gacaaactgc    420
atatttatga ccatgaataa cccgccggac tggaccaaaa atgtcgagta cacttttact    480
ggaatatata cttttgaatc acttgtaaaa atccttgcaa gaggcttctg tgtaggagaa    540
ttcacttttc ttcgtgaccc gtggaactgg ctggattttg tcgtcattgt ttttgcgtat    600
ttaacagaat ttgtaaacct aggcaatgtt tcagctcttc aactttcag agtattgaga     660 gctttgaaaa ctatttctgt aatcccaggc ctgaagacaa ttgtaggggc tttgatccag    720
tcagtgaaga agctttctga tgtcatgatc ctgactgtgt tctgtctgag tgtgtttgca    780
ctaattggac tacagctgtt catgggaaac ctgaagcata atgttttcg aaattcactt     840 gaaaataatg aaacattaga aagcataatg aatacccttag agagtgaaga agactttaga    900
aaatattttt attacttgga aggatccaaa gatgctctcc tttgtggttt cagcacagat    960
tcaggtcagt gtccagaggg gtacacctgt gtgaaaattg gcagaaaccc tgattatggc   1020
tacacgagct ttgacacttt cagctgggcc ttcttagcct tgtttaggct aatgacccaa   1080
gattactggg aaaaccttta ccaacagacg ctgcgtgctg ctggcaaaac ctacatgatc   1140
ttctttgtcg tagtgatttt cctgggctcc ttttatctaa taaacttgat cctggctgtg   1200
gttgccatgg catatgaaga acagaaccag gcaaacattg aagaagctaa acagaaagaa   1260
ttagaatttc aacagatgtt agaccgtctt aaaaaagagc aagaagaagc tgaggcaatt   1320
gcagcggcag cggctgaata tacaagtatt aggagaagca gaattatggg cctctcagag   1380
agttcttctg aaacatccaa actgagctct aaaagtgcta agaaagaag aaacagaaga   1440 aagaaaaaga atcaaaagaa gctctccagt ggagaggaaa agggagatgc tgagaaattg   1500
tcgaaatcag aatcagagga cagcatcaga agaaaaagtt tccaccttgg tgtcgaaggg   1560
cataggcgag cacatgaaaa gaggttgtct accccaatc agtcaccact cagcattcgt    1620
ggctccttgt tttctgcaag gcgaagcagc agaacaagtc ttttagttt caaaggcaga    1680 ggaagagata taggatctga gactgaattt gccgatgatg agcacagcat ttttggagac   1740
aatgagagca gaagggggctc actgtttgtg ccccacagac cccaggagcg acgcagcagt   1800
aacatcagcc aagccagtag gtccccacca atgctgccgg tgaacgggaa aatgcacagt   1860
gctgtggact gcaacggtgt ggtctccctg gttgatggac gctcagccct catgctcccc   1920
aatggacagc ttctgccaga gggcacgacc aatcaaatac acaagaaaag gcgttgtagt   1980
tcctatctcc tttcagagga tatgctgaat gatcccaacc tcagacagag agcaatgagt   2040
agagcaagca tattaacaaa cactgtggaa gaacttgaag agtccagaca aaaatgtcca   2100
ccttggtggt acagatttgc acacaaattc ttgatctgga attgctctcc atattggata   2160
aaattcaaaa agtgtatcta ttttattgta atggatcctt ttgtagatct tgcaattacc   2220
atttgcatag ttttaaacac attatttatg gctatggaac accacccaat gactgaggaa   2280
ttcaaaaatg tacttgctat aggaaatttg gtctttactg gaatctttgc agctgaaatg   2340
gtattaaaac tgattgccat ggatccatat gagtatttcc aagtaggctg gaatattttt   2400
gacagcctta ttgtgacttt aagtttagtg gagctctttc tagcagatgt ggaaggattg   2460
```

```
tcagttctgc gatcattcag actgctccga gtcttcaagt tggcaaaatc ctggccaaca    2520
ttgaacatgc tgattaagat cattggtaac tcagtagggg ctctaggtaa cctcacctta    2580
gtgttggcca tcatcgtctt cattttgct gtggtcggca tgcagctctt tggtaagagc     2640
tacaaagaat gtgtctgcaa gatcaatgat gactgtacgc tcccacggtg gcacatgaac    2700
gacttcttcc actccttcct gattgtgttc cgcgtgctgt gtggagagtg gatagagacc    2760
atgtgggact gtatggaggt cgctggtcaa gctatgtgcc ttattgttta catgatggtc    2820
atggtcattg gaaacctggt ggtcctaaac ctatttctgg ccttattatt gagctcattt    2880
agttcagaca atcttacagc aattgaagaa gaccctgatg caaacaacct ccagattgca    2940
gtgactagaa ttaaaaaggg aataaattat gtgaaacaaa ccttacgtga atttattcta    3000
aaagcatttt ccaaaaagcc aaagatttcc agggagataa gacaagcaga agatctgaat    3060
actaagaagg aaaactatat ttctaaccat acacttgctg aaatgagcaa aggtcacaat    3120
ttcctcaagg aaaaagataa aatcagtggt tttggaagca gcgtggacaa acacttgatg    3180
gaagacagtg atggtcaatc atttattcac aatcccagcc tcacagtgac agtgccaatt    3240
gcacctgggg aatccgattt ggaaaatatg aatgctgagg aacttagcag tgattcggat    3300
agtgaataca gcaaagtgag attaaaccgg tcaagctcct cagagtgcag cacagttgat    3360
aaccctttgc ctggagaagg agaagaagca gaggctgaac ctatgaattc cgatgagcca    3420
gaggcctgtt tcacagatgg ttgtgtacgg aggttctcat gctgccaagt taacatagag    3480
tcagggaaag gaaaaatctg gtggaacatc aggaaaacct gctacaagat tgttgaacac    3540
agttggtttg aaagcttcat tgtcctcatg atcctgctca gcagtggtgc cctggctttt    3600
gaagatattt atattgaaag gaaaaagacc attaagatta tcctggagta tgcagacaag    3660
atcttcactt acatcttcat tctggaaatg cttctaaaat ggatagcata tggttataaa    3720
acatatttca ccaatgcctg tgtgttggctg gatttcctaa ttgttgatgt ttctttggtt    3780
actttagtgg caaacactct tggctactca gatcttggcc ccattaaatc ccttcggaca    3840
ctgagagctt aagacctct aagagccttaa tctagatttg aaggaatgag ggtcgttgtg    3900
aatgcactca taggagcaat tccttccatc atgaatgtgc tacttgtgtg tcttatattc    3960
tggctgatat tcagcatcat gggagtaaat ttgtttgctg gcaagttcta tgagtgtatt    4020
aacaccacag atgggtcacg gtttcctgca agtcaagttc caaatcgttc cgaatgtttt    4080
gcccttatga atgttagtca aaatgtgcga tggaaaaacc tgaaagtgaa ctttgataat    4140
gtcggacttg gttacctatc tctgcttcaa gttgcaactt ttaagggatg gacgattatt    4200
atgtatgcag cagtggattc tgttaatgta gacaagcagc ccaaatatga atatagcctc    4260
tacatgtata tttattttgt cgtctttatc atctttgggt cattcttcac tttgaacttg    4320
ttcattggtg tcatcatata taatttcaac caacagaaaa agaagcttgg aggtcaagac    4380
atctttatga cagaagaaca gaagaaatac ataatgcaa tgaaaaagct ggggtccaag    4440
aagccacaaa agccaattcc tcgaccaggg aacaaaatcc aaggatgtat atttgaccta    4500
gtgacaaatc aagcctttga tattagtatc atggttctta tctgtctcaa catggtaacc    4560
atgatggtag aaaaggaggg tcaaagtcaa catatgactg aagttttata ttggataaat    4620
gtggttttta taatccttt cactggagaa tgtgtgctaa aactgatctc cctcagacac    4680
tactacttca ctgtaggatg gaatattttt gattttgtgg ttgtgattat ctccattgta    4740
ggtatgtttc tagctgattt gattgaaacg tattttgtgt cccctaccct gttccgagtg    4800
```

```
atccgtcttg ccaggattgg ccgaatccta cgtctagtca aaggagcaaa ggggatccgc      4860
acgctgctct ttgctttgat gatgtccctt cctgcgttgt ttaacatcgg cctcctgctc      4920
ttcctggtca tgttcatcta cgccatcttt ggaatgtcca actttgccta tgttaaaaag      4980
gaagatggaa ttaatgacat gttcaatttt gagacctttg gcaacagtat gatttgcctg      5040
ttccaaatta caacctctgc tggctgggat ggattgctag cacctattct taacagtaag      5100
ccacccgact gtgacccaaa aaagttcat cctggaagtt cagttgaagg agactgtggt      5160
aacccatctg ttggaatatt ctactttgtt agttatatca tcatatcctt cctggttgtg      5220
gtgaacatgt acattgcagt catactggag aattttagtg ttgccactga agaaagtact      5280
gaacctctga gtgaggatga ctttgagatg ttctatgagg tttgggagaa gtttgatccc      5340
gatgcgaccc agtttataga gttctctaaa ctctctgatt ttgcagctgc cctggatcct      5400
cctcttctca tagcaaaacc caacaaagtc cagctcattg ccatggatct gcccatggtt      5460
agtggtgacc ggatccattg tcttgacatc ttatttgctt ttacaaagcg tgttttgggt      5520
gagagtgggg agatggattc tcttcgttca cagatggaag aaaggttcat gtctgcaaat      5580
ccttccaaag tgtcctatga acccatcaca accacactaa acggaaaca agaggatgtg      5640 tctgctactg tcattcagcg tgcttataga cgttaccgct taaggcaaaa tgtcaaaaat      5700
atatcaagta tatacataaa agatggagac agagatgatg atttactcaa taaaaaagat      5760
atggcttttg ataatgttaa tgagaactca agtccagaaa aacagatgc cacttcatcc      5820 accacctctc caccttcata tgatagtgta acaaagccag acaaagagaa atatgaacaa      5880
gacagaacag aaaaggaaga caaagggaaa gacagcaagg aaagcaaaaa atag            5934
```

<210> SEQ ID NO 9
<211> LENGTH: 5934
<212> TYPE: DNA
<213> ORGANISM: Artificial Sequence
<220> FEATURE:
<223> OTHER INFORMATION: Description of Artificial Sequence:/note = synthetic construct

<400> SEQUENCE: 9

```
atggcaatgt tgcctccccc aggacctcag agctttgtcc atttcacaaa acagtctctt       60
gccctcattg aacaacgcat tgctgaaaga aaatcaaagg aacccaaaga agaaaagaaa      120
gatgatgatg aagaagcccc aaagccaagc agtgacttgg aagctggcaa caactgccc      180 ttcatctatg gggacattcc tcccggcatg gtgtcagagc cctggagga cttggacccc      240 tactatgcag acaaaaagac tttcatagta ttgaacaaag ggaaaacaat cttccgtttc      300
aatgccacac tgctttata tatgctttct cctttcagtc ctctaagaag aatatctatt      360
aagattttag tacactcctt attcagcatg ctcatcatgt gcactattct gacaaactgc      420
atatttatga ccatgaataa cccgcaggac tggaccaaaa atgtcgagta cactttact      480 ggaatatata cttttgaatc acttgtaaaa atccttgcaa gaggcttctg tgtaggagaa      540
ttcacttttc ttcgtgaccc gtggaactgg ctggattttg tcgtcattgt ttttgcgtat      600
ttaacagaat ttgtaaacct aggcaatgtt tcagctcttc gaactttcag agtattgaga      660
gctttgaaaa ctatttctgt aatcccaggc ctgaagacaa ttgtagggc tttgatccag      720 tcagtgaaga agcttctga tgtcatgatc ctgactgtgt tctgtctgag tgtgtttgca      780
ctaattggac tacagctgtt catgggaaac ctgaagcata atgttttcg aaattcactt      840 gaaaataatg aaacattaga aagcataatg aataccctag agagtgaaga agactttaga      900
```

```
aaatatttt attacttgga aggatccaaa gatgctctcc tttgtggttt cagcacagat      960
tcaggtcagt gtccagaggg gtacacctgt gtgaaaattg gcagaaaccc tgattatggc     1020
tacacgagct ttgacacttt cagctgggcc ttcttagcct tgtttaggct aatgacccaa     1080
gattactggg aaaacccttta ccaacagacg ctgcgtgctg ctggcaaaac ctacatgatc    1140
ttctttgtcg tagtgatttt cctgggctcc ttttatctaa taaacttgat cctggctgtg     1200
gttgccatgg catatgaaga acagaaccag gcaaacattg aagaagctaa acagaaagaa     1260
ttagaatttc aacagatgtt agaccgtctt aaaaagagc aagaagaagc tgaggcaatt      1320
gcagcggcag cggctgaata tacaagtatt aggagaagca gaattatggg cctctcagag     1380
agttcttctg aaacatccaa actgagctct aaaagtgcta agaaagaag aaacagaaga      1440
aagaaaaga atcaaaagaa gctctccagt ggagaggaaa agggagatgc tgagaaattg      1500
tcgaaatcag aatcagagga cagcatcaga agaaaagtt ccaccttgg tgtcgaaggg       1560
cataggcgag cacatgaaaa gaggttgtct accccccaatc agtcaccact cagcattcgt   1620
ggctccttgt tttctgcaag gcgaagcagc agaacaagtc ttttttagttt caaaggcaga   1680
ggaagagata taggatctga gactgaattt gccgatgatg agcacagcat ttttggagac    1740
aatgagagca gaaggggctc actgtttgtg ccccacagac cccaggagcg acgcagcagt    1800
aacatcagcc aagccagtag gtccccacca atgctgccgg tgaacgggaa aatgcacagt    1860
gctgtggact gcaacggtgt ggtctccctg gttgatggac gctcagccct catgctcccc    1920
aatggacagc ttctgccaga gggcacgacc aatcaaatac acaagaaaag gcgttgtagt   1980
tcctatctcc tttcagagga tatgctgaat gatcccaacc tcagacagag agcaatgagt   2040
agagcaagca tattaacaaa cactgtggaa gaacttgaag agtccagaca aaaatgtcca   2100
ccttggtggt acagatttgc acacaaattc ttgatctgga attgctctcc atattggata   2160
aaattcaaaa agtgtatcta ttttattgta atggatcctt tgtagatct tgcaattacc     2220
atttgcatag ttttaaacac attattatg gctatggaac accacccaat gactgaggaa    2280
ttcaaaaatg tacttgctat aggaaattttg gtctttactg gaatctttgc agctgaaatg   2340
gtattaaaac tgattgccat ggatccatat gagtatttcc aagtaggctg gaatatttt    2400
gacagcctta ttgtgacttt aagtttagtg gagctctttc tagcagatgt ggaaggattg    2460
tcagttctgc gatcattcag actgctccga gtcttcaagt tggcaaaatc ctggccaaca   2520
ttgaacatgc tgattaagat cattggtaac tcagtagggg ctctaggtaa cctcacctta   2580
gtgttggcca tcatcgtctt catttttgct gtggtcggca tgcagctctt tggtaagagc   2640
tacaaagaat gtgtctgcaa gatcaatgat gactgtacgc tcccacggtg gcacatgaac   2700
gacttcttcc actccttcct gattgtgttc cgcgtgctgt gtggagagtg gatagagacc   2760
atgtgggact gtatggaggt cgctggtcaa gctatgtgcc ttattgttta catgatggtc   2820
atggtcattg gaaacctggt ggtcctaaac ctatttctgg ccttattatt gagctcattt   2880
agttcagaca atcttacagc aattgaagaa gaccctgatg caaacaacct ccagattgca   2940
gtgactagaa ttaaaaggg aataaattat gtgaaacaaa ccttacgtga atttattcta   3000
aaagcatttt ccaaaagcc aaagatttcc agggagataa gacaagcaga agatctgaat   3060
actaagaagg aaaactatat ttctaaccat acacttgctg aaatgagcaa aggtcacaat   3120
ttcctcaagg aaaagataa aatcagtggt tttggaagca gcgtggacaa acacttgatg   3180
gaagacagtg atggtcaatc atttattcac aatcccagcc tcacagtgac agtgccaatt   3240
gcacctgggg aatccgattt ggaaaatatg aatgctgagg aacttagcag tgattcggat   3300
```

```
agtgaataca gcaaagtgag attaaaccgg tcaagctcct cagagtgcag cacagttgat    3360 aacccttttgc ctggagaagg agaagaagca gaggctgaac ctatgaattc cgatgagcca   3420
gaggcctgtt tcacagatgg ttgtgtacgg aggttctcat gctgccaagt taacatagag   3480
tcagggaaag gaaaaatctg gtggaacatc aggaaaacct gctacaagat tgttgaacac   3540
agttggtttg aaagcttcat tgtcctcatg atcctgctca gcagtggtgc cctggctttt   3600
gaagatattt atattgaaag gaaaaagacc attaagatta tcctggagta tgcagacaag   3660
atcttcactt acatcttcat tctgaaatg cttctaaaat ggatagcata tggttataaa    3720
acatatttca ccaatgcctg tgtgttggctg gatttcctaa ttgttgatgt ttctttggtt   3780
actttagtgg caaacactct tggctactca gatcttggcc ccattaaatc ccttcggaca   3840
ctgagagctt taagacctct aagagcctta tctagatttg aaggaatgag ggtcgttgtg   3900
aatgcactca taggagcaat tccttccatc atgaatgtgc tacttgtgtg tcttatattc   3960
tggctgatat tcagcatcat gggagtaaat ttgtttgctg gcaagttcta tgagtgtatt   4020
aacaccacag atgggtcacg gtttcctgca agtcaagttc caaatcgttc cgaatgtttt   4080
gcccttatga atgttagtca aaatgtgcga tggaaaaacc tgaaagtgaa ctttgataat   4140
gtcggacttg gttacctatc tctgcttcaa gttgcaactt ttaagggatg gacgattatt   4200
atgtatgcag cagtggattc tgttaatgta gacaagcagc ccaaatatga atatagcctc   4260
tacatgtata tttatttgt cgtctttatc atctttgggt cattcttcac tttgaacttg   4320
ttcattggtg tcatcataga taatttcaac caacagaaaa agaagcttgg aggtcaagac   4380
atctttatga cagaagaaca gaagaaatac tataatgcaa tgaaaaagct ggggtccaag   4440
aagccacaaa agccaattcc tcgaccaggg aacaaaatcc aaggatgtat atttgaccta   4500
gtgacaaatc aagcctttga tattagtatc atggttctta tctgtctcaa catggtaacc   4560
atgatggtag aaaaggaggg tcaaagtcaa catatgactg aagttttata ttggataaat   4620
gtggttttta atcctttt cactggagaa tgtgtgctaa actgatctc cctcagacac     4680 tactacttca ctgtaggatg gaatattttt gattttgtgg ttgtgattat ctccattgta   4740
ggtatgtttc tagctgattt gattgaaacg tattttgtgt cccctaccct gttccgagtg   4800
atccgtcttg ccaggattgg ccgaatccta cgtctagtca aaggagcaaa ggggatccgc   4860
acgctgctct ttgctttgat gatgtccctt cctgcgttgt taacatcgg cctcctgctc    4920 ttcctggtca tgttcatcta cgccatcttt ggaatgtcca actttgccta tgttaaaaag   4980
gaagatggaa ttaatgacat gttcaatttt gagacctttg gcaacagtat gatttgcctg   5040
ttccaaatta caacctctgc tggctgggat ggattgctag cacctattct taacagtaag   5100
ccacccgact gtgacccaaa aaaagttcat cctggaagtt cagttgaagg agactgtggt   5160
aacccatctg ttggaatatt ctactttgtt agttatatca tcatatcctt cctggttgtg   5220
gtgaacatgt acattgcagt catactggag aattttagtg ttgccactga agaaagtact   5280
gaacctctga gtgaggatga ctttgagatg ttctatgagg tttgggagaa gtttgatccc   5340
gatgcgaccc agtttataga gttctctaaa ctctctgatt ttgcagctgc cctggatcct   5400
cctcttctca tagcaaaacc caacaaagtc cagctcattg ccatggatct gcccatggtt   5460
agtggtgacc ggatccattg tcttgacatc ttatttgctt ttacaaagcg tgttttgggt   5520
gagagtgggg agatggattc tcttcgttca cagatggaag aaaggttcat gtctgcaaat   5580
ccttccaaag tgtcctatga acccatcaca accacactaa aacggaaaca agaggatgtg   5640
```

-continued

| | |
|---|---|
| tctgctactg tcattcagcg tgcttataga cgttaccgct taaggcaaaa tgtcaaaaat | 5700 |
| atatcaagta tatacataaa agatggagac agagatgatg atttactcaa taaaaaagat | 5760 |
| atggcttttg ataatgttaa tgagaactca agtccagaaa aaacagatgc cacttcatcc | 5820 |
| accacctctc caccttcata tgatagtgta acaaagccag acaaagagaa atatgaacaa | 5880 |
| gacagaacag aaaaggaaga caaagggaaa gacagcaagg aaagcaaaaa atag | 5934 |

<210> SEQ ID NO 10
<211> LENGTH: 5934
<212> TYPE: DNA
<213> ORGANISM: Artificial Sequence
<220> FEATURE:
<223> OTHER INFORMATION: Description of Artificial Sequence:/note = synthetic construct

<400> SEQUENCE: 10

| | |
|---|---|
| atggcaatgt tgcctccccc aggacctcag agctttgtcc atttcacaaa acagtctctt | 60 |
| gccctcattg aacaacgcat tgctgaaaga aaatcaaagg aacccaaaga agaaaagaaa | 120 |
| gatgatgatg aagaagcccc aaagccaagc agtgacttgg aagctggcaa acaactgccc | 180 |
| ttcatctatg gggacattcc tcccggcatg gtgtcagagc ccctggagga cttggacccc | 240 |
| tactatgcag acaaaaagac tttcatagta ttgaacaaag ggaaaacaat cttccgtttc | 300 |
| aatgccacac ctgctttata tatgctttct cctttcagtc ctctaagaag aatatctatt | 360 |
| aagatttttag tacactcctt attcagcatg ctcatcatgt gcactattct gacaaactgc | 420 |
| atatttatga ccatgaataa cccgccggac tggaccaaaa atgtcgagta cacttttact | 480 |
| ggaatatata cttttgaatc acttgtaaaa atccttgcaa gaggcttctg tgtaggagaa | 540 |
| ttcactttc ttcgtgaccc gtggaactgg ctggattttg tcgtcattgt ttttgcgtat | 600 |
| ttaacagaat tgtaaaccct aggcaatgtt tcagctcttc gaactttcag agtattgaga | 660 |
| gctttgaaaa ctatttctgt aatcccaggc ctgaagacaa ttgtagggggc tttgatccag | 720 |
| tcagtgaaga agcttctctga tgtcatgatc ctgactgtgt tctgtctgag tgtgtttgca | 780 |
| ctaattggac tacagctgtt catgggaaac ctgaagcata aatgttttcg aaattcactt | 840 |
| gaaaataatg aaacattaga agcataatg aatacccctag agagtgaaga agactttaga | 900 |
| aaatattttt attacttgga aggatccaaa gatgctctcc tttgtggttt cagcacagat | 960 |
| tcaggtcagt gtccagaggg gtacacctgt gtgaaaattg gcagaaaccc tgattatggc | 1020 |
| tacacgagct ttgacacttt cagctgggcc ttcttagcct tgtttaggct aatgacccaa | 1080 |
| gattactggg aaaaccttta ccaacagacg ctgcgtgctg ctggcaaaac ctacatgatc | 1140 |
| ttctttgtcg tagtgatttt cctgggctcc ttttatctaa taaacttgat cctggctgtg | 1200 |
| gttgccatgg catatgaaga acagaaccag gcaaacattg aagaagctaa acagaaagaa | 1260 |
| ttagaatttc aacagatgtt agaccgtctt aaaaaagagc aagaagaagc tgaggcaatt | 1320 |
| gcagcggcag cggctgaata tacaagtatt aggagaagca gaattatggg cctctcagag | 1380 |
| agttcttctg aaacatccaa actgagctct aaaagtgcta agaaagaag aaacagaaga | 1440 |
| aagaaaaaga atcaaaagaa gctctccagt ggagaggaaa agggagatgc tgagaaattg | 1500 |
| tcgaaatcag aatcagagga cagcatcaga agaaaaagtt ccacccttgg tgtcgaaggg | 1560 |
| cataggcgag cacatgaaaa gaggttgtct acccccaatc agtcaccact cagcattcgt | 1620 |
| ggctccttgt tttctgcaag gcgaagcagc agaacaagtc ttttttagttt caaaggcaga | 1680 |
| ggaagagata taggatctga gactgaattt gccgatgatg agcacagcat ttttggagac | 1740 |

-continued

```
aatgagagca gaaggggctc actgtttgtg ccccacagac cccaggagcg acgcagcagt    1800
aacatcagcc aagccagtag gtccccacca atgctgccgg tgaacgggaa aatgcacagt    1860
gctgtggact gcaacggtgt ggtctccctg gttgatggac gctcagccct catgctcccc    1920
tatggacagc ttctgccaga gggcacgacc aatcaaatac acaagaaaag gcgttgtagt    1980
tcctatctcc tttcagagga tatgctgaat gatcccaacc tcagacagag agcaatgagt    2040
agagcaagca tattaacaaa cactgtggaa gaacttgaag agtccagaca aaaatgtcca    2100
ccttggtggt acagatttgc acacaaattc ttgatctgga attgctctcc atattggata    2160
aaattcaaaa agtgtatcta ttttattgta atggatcctt ttgtagatct tgcaattacc    2220
atttgcatag ttttaaacac attatttatg gctatggaac accacccaat gactgaggaa    2280
ttcaaaaatg tacttgctat aggaaatttg gtctttactg gaatctttgc agctgaaatg    2340
gtattaaaac tgattgccat ggatccatat gagtatttcc aagtaggctg gaatattttt    2400
gacagcctta ttgtgacttt aagtttagtg gagctctttc tagcagatgt ggaaggattg    2460
tcagttctgc gatcattcag actgctccga gtcttcaagt tggcaaaatc ctggccaaca    2520
ttgaacatgt tgattaagat cattggtaac tcagtagggg ctctaggtaa cctcaccttg    2580
gtgttggcca tcatcgtctt cattttttgct gtggtcggca tgcagctctt tggtaagagc    2640
tacaaagaat gtgtctgcaa gatcaatgat gactgtacgc tcccacggtg gcacatgaac    2700
gacttcttcc actccttcct gattgtgttc cgcgtgctgt gtggagagtg gatagagacc    2760
atgtgggact gtatggaggt cgctggtcaa gctatgtgcc ttattgttta catgatggtc    2820
atggtcattg gaaacctggt ggtcctaaac ctatttctgg ccttattatt gagctcattt    2880
agttcagaca atcttacagc aattgaagaa gaccctgatg caaacaacct ccagattgca    2940
gtgactagaa ttaaaaaggg aataaattat gtgaaacaaa ccttacgtga atttattcta    3000
aaagcatttt ccaaaaagcc aaagatttcc agggagataa gacaagcaga agatctgaat    3060
actaagaagg aaaactatat ttctaaccat acacttgctg aaatgagcaa aggtcacaat    3120
ttcctcaagg aaaaagataa aatcagtggt tttggaagca gcgtggacaa acacttgatg    3180
gaagacagtg atggtcaatc atttattcac aatcccagcc tcacagtgac agtgccaatt    3240
gcacctgggg aatccgattt ggaaaatatg aatgctgagg aacttagcag tgattcggat    3300
agtgaataca gcaaagtgag attaaaccgg tcaagctcct cagagtgcag cacagttgat    3360
aaccctttgc ctggagaagg agaagaagca gaggctgaac ctatgaattc cgatgagcca    3420
gaggcctgtt tcacagatgg ttgtgtacgg aggttctcat gctgccaagt taacatagag    3480
tcagggaaag gaaaaatctg gtggaacatc aggaaaacct gctacaagat tgttgaacac    3540
agttggtttg aaagcttcat tgtcctcatg atcctgctca gcagtggtgc cctggctttt    3600
gaagatattt atattgaaag gaaaagacc attaagatta tcctggagta tgcagacaag    3660
atcttcactt acatcttcat tctgaaatg cttctaaaat ggatagcata tggttataaa    3720
acatatttca ccaatgcctg gtgttggctg gatttcctaa ttgttgatgt ttctttggtt    3780
actttagtgg caaacactct tggctactca gatcttggcc ccattaaatc ccttcggaca    3840
ctgagagctt taagacctct aagagcctta tctagatttg aaggaatgag ggtcgttgtg    3900
aatgcactca ggagcaat tccttccatc atgaatgtgc tacttgtgtg tcttatattc    3960
tggctgatat tcagcatcat gggagtaaat ttgtttgctg gcaagttcta tgagtgtatt    4020
aacaccacag atgggtcacg gtttcctgca agtcaagttc caaatcgttc cgaatgtttt    4080
gcccttatga atgttagtca aaatgtgcga tggaaaaacc tgaaagtgaa ctttgataat    4140
```

-continued

```
gtcggacttg gttacctatc tctgcttcaa gttgcaactt ttaagggatg gacgattatt    4200
atgtatgcag cagtggattc tgttaatgta gacaagcagc ccaaatatga atatagcctc    4260
tacatgtata tttattttgt cgtctttatc atctttgggt cattcttcac tttgaacttg    4320
ttcattggtg tcatcataga taatttcaac caacagaaaa agaagcttgg aggtcaagac    4380
atctttatga cagaagaaca gaagaaatac tataatgcaa tgaaaaagct ggggtccaag    4440
aagccacaaa agccaattcc tcgaccaggg aacaaaatcc aaggatgtat atttgaccta    4500
gtgacaaatc aagcctttga tattagtatc atggttctta tctgtctcaa catggtaacc    4560
atgatggtag aaaaggaggg tcaaagtcaa catatgactg aagttttata ttggataaat    4620
gtggttttta taatcctttt cactggagaa tgtgtgctaa aactgatctc cctcagacac    4680
tactacttca ctgtaggatg gaatattttt gattttgtgg ttgtgattat ctccattgta    4740
ggtatgtttc tagctgattt gattgaaacg tattttgtgt ccctaccct gttccgagtg    4800
atccgtcttg ccaggattgg ccgaatccta cgtctagtca aaggagcaaa ggggatccgc    4860
acgctgctct ttgctttgat gatgtcccct cctgcgttgt ttaacatcgg cctcctgctc    4920
ttcctggtca tgttcatcta cgccatcttt ggaatgtcca actttgccta tgttaaaaag    4980
gaagatggaa ttaatgacat gttcaatttt gagacctttg gcaacagtat gatttgcctg    5040
ttccaaatta caacctctgc tggctgggat ggattgctag cacctattct taacagtaag    5100
ccacccgact gtgacccaaa aaagttcat cctggaagtt cagttgaagg agactgtggt    5160
aacccatctg ttgaatatat ctactttgtt agttatatca tcatatcctt cctggttgtg    5220
gtgaacatgt acattgcagt catactggag aattttagtg ttgccactga agaaagtact    5280
gaacctctga gtgaggatga ctttgagatg ttctatgagg tttgggagaa gtttgatccc    5340
gatgcgaccc agtttataga gttctctaaa ctctctgatt ttgcagctgc cctggatcct    5400
cctcttctca tagcaaaacc caacaaagtc cagctcattg ccatggatct gcccatggtt    5460
agtggtgacc ggatccattg tcttgacatc ttatttgctt ttacaaagcg tgttttgggt    5520
gagagtgggg agatggattc tcttcgttca cagatggaag aaaggttcat gtctgcaaat    5580
ccttccaaag tgtcctatga acccatcaca accacactaa aacggaaaca agaggatgtg    5640
tctgctactg tcattcagcg tgcttataga cgttaccgct taaggcaaaa tgtcaaaaat    5700
atatcaagta tatacataaa agatggagac agagatgatg atttactcaa taaaaaagat    5760
atggcttttg ataatgttaa tgagaactca agtccagaaa aaacagatgc cacttcatcc    5820
accacctctc caccttcata tgatagtgta acaaagccag acaaagagaa atatgaacaa    5880
gacagaacag aaaaggaaga caaagggaaa gacagcaagg aaagcaaaaa atag           5934
```

<210> SEQ ID NO 11
<211> LENGTH: 5934
<212> TYPE: DNA
<213> ORGANISM: Artificial Sequence
<220> FEATURE:
<223> OTHER INFORMATION: Description of Artificial Sequence:/note = synthetic construct

<400> SEQUENCE: 11

```
atggcaatgt tgcctccccc aggacctcag agctttgtcc atttcacaaa acagtctctt      60
gccctcattg aacaacgcat tgctgaaaga aaatcaaagg aacccaaaga agaaaagaaa     120
gatgatgatg aagaagcccc aaagccaagc agtgacttgg aagctggcaa acaactgccc     180
ttcatctatg gggacattcc tcccggcatg gtgtcagagc ccctggagga cttggacccc     240
```

-continued

```
tactatgcag acaaaaagac tttcatagta ttgaacaaag ggaaaacaat cttccgtttc      300
aatgccacac ctgctttata tatgctttct cctttcagtc ctctaagaag aatatctatt      360
aagattttag tacactcctt attcagcatg ctcatcatgt gcactattct gacaaactgc      420
atatttatga ccatgaataa cccgccggac tggaccaaaa atgtcgagta cacttttact      480
ggaatatata cttttgaatc acttgtaaaa atccttgcaa gaggcttctg tgtaggagaa      540
ttcactttc ttcgtgaccc gtggaactgg ctggattttg tcgtcattgt ttttgcgtat       600
ttaacagaat tgtaaaacct aggcaatgtt tcagctcttc gaactttcag agtattgaga      660
gctttgaaaa ctatttctgt aatcccaggc ctgaagacaa ttgtaggggc tttgatccag      720
tcagtgaaga agctttctga tgtcatgatc ctgactgtgt tctgtctgag tgtgtttgca      780
ctaattggac tacagctgtt catgggaaac ctgaagcata aatgttttcg aaattcactt      840
gaaaataatg aaacattaga aagcataatg aatacctag agagtgaaga agactttaga       900
aaatattttt attacttgga aggatccaaa gatgctctcc tttgtggttt cagcacagat      960
tcaggtcagt gtccagaggg gtacacctgt gtgaaaattg cagaaaccc tgattatggc      1020
tacacgagct ttgacacttt cagctgggcc ttcttagcct tgtttaggct aatgacccaa      1080
gattactggg aaaaccttta ccaacagacg ctgcgtgctg ctggcaaaac ctacatgatc      1140
ttctttgtcg tagtgatttt cctgggctcc ttttatctaa taaacttgat cctggctgtg      1200
gttgccatgg catatgaaga acagaaccag gcaaacattg aagaagctaa acagaaagaa      1260
ttagaatttc aacagatgtt agaccgtctt aaaaaagagc aagaagaagc tgaggcaatt      1320
gcagcggcag cggctgaata tacaagtatt aggagaagca gaattatggg cctctcagag      1380
agttcttctg aaacatccaa actgagctct aaaagtgcta agaaagaag aaacagaaga      1440
aagaaaaaga atcaaaagaa gctctccagt ggagaggaaa agggagatgc tgagaaattg      1500
tcgaaatcag aatcagagga cagcatcaga agaaaaagtt ccaccttggg tgtcgaaggg      1560
cataggcgag cacatgaaaa gaggttgtct accccaatc agtcaccact cagcattcgt       1620
ggctccttgt tttctgcaag gcgaagcagc agaacaagtc tttttagttt caaaggcaga      1680
ggaagagata taggatctga gactgaattt gccgatgatg agcacagcat ttttggagac      1740
aatgagagca gaaggggctc actgtttgtg ccccacagac cccaggagcg acgcagcagt      1800
aacatcagcc aagccagtag gtccccacca atgctgccgg tgaacgggaa aatgcacagt      1860
gctgtggact gcaacggtgt ggtctccctg gttgatggac gctcagccct catgctcccc      1920
aatggacagc ttctgccaga gggcacgacc aatcaaatac acaggaaaag gcgttgtagt      1980
tcctatctcc tttcagagga tatgctgaat gatcccaacc tcagacagag agcaatgagt      2040
agagcaagca tattaacaaa cactgtggaa gaacttgaag agtccagaca aaaatgtcca      2100
ccttggtggt acagatttgc acacaaattc ttgatctgga attgctctcc atattggata      2160
aaattcaaaa agtgtatcta ttttattgta atggatcctt ttgtagatct tgcaattacc      2220
atttgcatag ttttaaacac attatttatg gctatggaac accacccaat gactgaggaa      2280
ttcaaaaatg tacttgctat aggaaatttg gtctttactg gaatctttgc agctgaaatg      2340
gtattaaaac tgattgccat ggatccatat gagtatttcc aagtaggctg gaatattttt      2400
gacagcctta ttgtgacttt aagtttagtg gagctctttc tagcagatgt ggaaggattg      2460
tcagttctgc gatcattcag actgctccga gtcttcaagt tggcaaaatc ctggccaaca      2520
ttgaacatgc tgattaagat cattggtaac tcagtagggg ctctaggtaa cctcacctta      2580
```

```
gtgttggcca tcatcgtctt catttttgct gtggtcggca tgcagctctt tggtaagagc    2640
tacaaagaat gtgtctgcaa gatcaatgat gactgtacgc tcccacggtg gcacatgaac    2700
gacttcttcc actccttcct gattgtgttc cgcgtgctgt gtggagagtg gatagagacc    2760
atgtgggact gtatggaggt cgctggtcaa gctatgtgcc ttattgttta catgatggtc    2820
atggtcattg gaaacctggt ggtcctaaac ctatttctgg ccttattatt gagctcattt    2880
agttcagaca atcttacagc aattgaagaa gaccctgatg caaacaacct ccagattgca    2940
gtgactagaa ttaaaaaggg aataaattat gtgaaacaaa ccttacgtga atttattcta    3000
aaagcatttt ccaaaaagcc aaagatttcc agggagataa gacaagcaga agatctgaat    3060
actaagaagg aaaactatat ttctaaccat acacttgctg aaatgagcaa aggtcacaat    3120
ttcctcaagg aaaaagataa aatcagtggt tttggaagca gcgtggacaa acacttgatg    3180
gaagacagtg atggtcaatc atttattcac aatcccagcc tcacagtgac agtgccaatt    3240
gcacctgggg aatccgattt ggaaaatatg aatgctgagg aacttagcag tgattcggat    3300
agtgaataca gcaaagtgag attaaaccgg tcaagctcct cagagtgcag cacagttgat    3360
aaccctttgc ctggagaagg agaagaagca gaggctgaac ctatgaattc cgatgagcca    3420
gaggcctgtt tcacagatgg ttgtgtacgg aggttctcat gctgccaagt taacatagag    3480
tcagggaaag gaaaaatctg gtggaacatc aggaaaacct gctacaagat tgttgaacac    3540
agttggtttg aaagcttcat tgtcctcatg atcctgctca gcagtggtgc cctggctttt    3600
gaagatattt atattgaaag gaaaaagacc attaagatta tcctggagta tgcagacaag    3660
atcttcactt acatcttcat tctggaaatg cttctaaaat ggatagcata tggttataaa    3720
acatatttca ccaatgcctg gtgttggctg gatttcctaa ttgttgatgt ttctttggtt    3780
actttagtgg caaacactct tggctactca gatcttggcc ccattaaatc ccttcggaca    3840
ctgagagctt taagacctct aagagcctta tctagatttg aaggaatgag ggtcgttgtg    3900
aatgcactca taggagcaat tccttccatc atgaatgtgc tacttgtgtg tcttatattc    3960
tggctgatat tcagcatcat gggagtaaat ttgtttgctg gcaagttcta tgagtgtatt    4020
aacaccacag atgggtcacg gtttcctgca agtcaagttc caaatcgttc cgaatgtttt    4080
gcccttatga atgttagtca aaatgtgcga tggaaaaacc tgaaagtgaa ctttgataat    4140
gtcggacttg gttacctatc tctgcttcaa gttgcaactt ttaagggatg gacgattatt    4200
atgtatgcag cagtggattc tgttaatgta gacaagcagc ccaaatatga atatagcctc    4260
tacatgtata tttattttgt cgtctttatc atctttgggt cattcttcac tttgaacttg    4320
ttcattggtg tcatcataga taatttcaac caacagaaaa agaagcttgg aggtcaagac    4380
atctttatga cagaagaaca gaagaaatac tataatgcaa tgaaaagct ggggtccaag    4440 aagccacaaa agccaattcc tcgaccaggg aacaaaatcc aaggatgtat atttgaccta    4500
gtgacaaatc aagcctttga tattagtatc atggttctta tctgtctcaa catggtaacc    4560
atgatggtag aaaaggaggg tcaaagtcaa catatgactg aagtttata ttggataaat    4620 gtggtttta taatccttt cactggagaa tgtgtgctaa aactgatctc cctcagacac    4680
tactacttca ctgtaggatg gaatatttt gattttgtgg ttgtgattat ctccattgta    4740
ggtatgtttc tagctgattt gattgaaacg tattttgtgt cccctaccct gttccgagtg    4800
atccgtcttg ccaggattgg ccgaatccta cgtctagtca aaggagcaaa ggggatccgc    4860
acgctgctct ttgctttgat gatgtccctt cctgcgttgt taacatcgg cctcctgctc    4920 ttcctggtca tgttcatcta cgccatcttt ggaatgtcca actttgccta tgttaaaaag    4980
```

-continued

```
gaagatggaa ttaatgacat gttcaatttt gagacctttg caacagtat gatttgcctg     5040 ttccaaatta caacctctgc tggctgggat ggattgctag cacctattct aacagtaag     5100 ccacccgact gtgacccaaa aaaagttcat cctggaagtt cagttgaagg agactgtggt    5160
aacccatctg ttggaatatt ctactttgtt agttatatca tcatatcctt cctggttgtg    5220
gtgaacatgt acattgcagt catactggag aattttagtg ttgccactga agaaagtact    5280
gaacctctga gtgaggatga ctttgagatg ttctatgagg tttgggagaa gtttgatccc    5340
gatgcgaccc agtttataga gttctctaaa ctctctgatt ttgcagctgc cctggatcct    5400
cctcttctca tagcaaaacc caacaaagtc cagctcattg ccatggatct gcccatggtt    5460
agtggtgacc ggatccattg tcttgacatc ttatttgctt ttacaaagcg tgttttgggt    5520
gagagtgggg agatggattc tcttcgttca cagatggaag aaaggttcat gtctgcaaat    5580
ccttccaaag tgtcctatga acccatcaca accacactaa acggaaaaca agaggatgtg    5640
tctgctactg tcattcagcg tgcttataga cgttaccgct taaggcaaaa tgtcaaaaat    5700
atatcaagta tatacataaa agatggagac agagatgatg atttactcaa taaaaaagat    5760
atggcttttg ataatgttaa tgagaactca agtccagaaa aaacagatgc cacttcatcc    5820
accacctctc caccttcata tgatagtgta acaaagccag acaaagagaa atatgaacaa    5880
gacagaacag aaaaggaaga caaagggaaa gacagcaagg aaagcaaaaa atag           5934
```

<210> SEQ ID NO 12
<211> LENGTH: 5934
<212> TYPE: DNA
<213> ORGANISM: Artificial Sequence
<220> FEATURE:
<223> OTHER INFORMATION: Description of Artificial Sequence:/note = synthetic construct

<400> SEQUENCE: 12

```
atggcaatgt tgcctccccc aggacctcag agctttgtcc atttcacaaa acagtctctt      60
gccctcattg caacacgcat tgctgaaaga aaatcaaagg aacccaaaga agaaaagaaa     120
gatgatgatg aagaagcccc aaagccaagc agtgacttgg aagctggcaa acaactgccc     180
ttcatctatg gggacattcc tcccggcatg gtgtcagagc ccctggagga cttggacccc     240
tactatgcag acaaaaagac tttcatagta ttgaacaaag ggaaaacaat cttccgtttc     300
aatgccacac ctgctttata tatgctttct cctttcagtc ctctaagaag aatatctatt     360 aagatttttag tacactcctt attcagcatg ctcatcatgt gcactattct gacaaactgc     420
atatttatga ccatgaataa cccgccggac tggaccaaaa atgtcgagta cacttttact     480
ggaatatata cttttgaatc acttgtaaaa atccttgcaa gaggcttctg tgtaggagaa     540
ttcacttttc ttcgtgaccc gtggaactgg ctggattttg tcgtcattgt ttttgcgtat     600
ttaacagaat ttgtaaacct aggcaatgtt tcagctcttc gaactttcag agtattgaga     660
gctttgaaaa ctatttctgt aatcccaggc ctgaagacaa ttgtaggggc tttgatccag     720
tcagtgaaga agctttctga tgtcatgatc ctgactgtgt tctgtctgag tgtgtttgca     780
ctaattggac tacagctgtt catgggaaac ctgaagcata atgttttcg aaattcactt     840 gaaaataatg aaacattaga aagcataatg aatacctag agagtgaaga agactttaga     900
aaatattttt attacttgga aggatccaaa gatgctctcc tttgtggttt cagcacagat     960
tcaggtcagt gtccagaggg gtacacctgt gtgaaaattg cagaaaaccc tgattatggc    1020
tacacgagct ttgacacttt cagctgggcc ttcttagcct tgtttaggct aatgacccaa    1080
```

```
gattactggg aaaacccttta ccaacagacg ctgcgtgctg ctggcaaaac ctacatgatc   1140
ttctttgtcg tagtgatttt cctgggctcc ttttatctaa taaacttgat cctggctgtg   1200
gttgccatgg catatgaaga acagaaccag gcaaacattg aagaagctaa acagaaagaa   1260
ttagaatttc aacagatgtt agaccgtctt aaaaaagagc aagaagaagc tgaggcaatt   1320
gcagcggcag cggctgaata tacaagtatt aggagaagca gaattatggg cctctcagag   1380
agttcttctg aaacatccaa actgagctct aaaagtgcta agaaagaag aaacagaaga    1440 aagaaaaaga atcaaaagaa gctctccagt ggagaggaaa agggagatgc tgagaaattg   1500
tcgaaatcag aatcagagga cagcatcaga agaaaaagtt tccaccttgg tgtcgaaggg   1560
cataggcgag cacatgaaaa gaggttgtct accccccaatc agtcaccact cagcattcgt   1620
ggctccttgt tttctgcaag gcgaagcagc agaacaagtc tttttagttt caaaggcaga   1680
ggaagagata taggatctga gactgaattt gccgatgatg agcacagcat ttttggagac   1740
aatgagagca gaaggggctc actgtttgtg ccccacagac cccaggagcg acgcagcagt   1800
aacatcagcc aagccagtag gtccccacca atgctgccgg tgaacgggaa aatgcacagt   1860
gctgtggact gcaacggtgt ggtctccctg gttgatggac gctcagccct catgctcccc   1920
aatggacagc ttctgccaga gggcacgacc aatcaaatac aagaaaaag gcgttgtagt   1980 tcctatctcc tttcagagga tatgctgaat gatcccaacc tcagacagag agcaatgagt   2040
agagcaagca tattaacaaa cactgtggaa gaacttgaag agtccagaca aaaatgtcca   2100
ccttggtggt acagatttgc acacaaattc ttgatctgga attgctctcc atattggata   2160
aaattcaaaa agtgtatcta ttttattgta atggatcctt ttgtagatct tgcagttacc   2220
atttgcatag ttttaaacac attatttatg gctatggaac accacccaat gactgaggaa   2280
ttcaaaaatg tacttgctat aggaaatttg gtctttactg gaatctttgc agctgaaatg   2340
gtattaaaac tgattgccat ggatccatat gagtatttcc aagtaggctg gaatattttt   2400
gacagcctta ttgtgacttt aagtttagtg gagctctttc tagcagatgt ggaaggattg   2460
tcagttctgc gatcattcag actgctccga gtcttcaagt tggcaaaatc ctggccaaca   2520
ttgaacatgc tgattaagat cattggtaac tcagtagggg ctctaggtaa cctcacctta   2580
gtgttggcca tcatcgtctt cattttgct gtggtcggca tgcagctctt tggtaagagc   2640
tacaaagaat gtgtctgcaa gatcaatgat gactgtacgc tcccacggtg gcacatgaac   2700
gacttcttcc actccttcct gattgtgttc cgcgtgctgt gtggagagtg gatagagacc   2760
atgtgggact gtatggaggt cgctggtcaa gctatgtgcc ttattgttta catgatggtc   2820
atggtcattg gaaacctggt ggtcctaaac ctatttctgg ccttattatt gagctcatt    2880 agttcagaca atcttacagc aattgaagaa gaccctgatg caaacaacct ccagattgca   2940
gtgactagaa ttaaaaaggg aataaattat gtgaaacaaa ccttacgtga atttattcta   3000
aaagcatttt ccaaaagcc aaagatttcc agggagataa gacaagcaga agatctgaat   3060
actaagaagg aaaactatat ttctaaccat acacttgctg aaatgagcaa aggtcacaat   3120
ttcctcaagg aaaaagataa aatcagtggt tttggaagca gcgtggacaa acacttgatg   3180
gaagacagtg atggtcaatc atttattcac aatcccagcc tcacagtgac agtgccaatt   3240
gcacctgggg aatccgattt ggaaaatatg aatgctgagg aacttagcag tgattcggat   3300
agtgaataca gcaaagtgag attaaaccgg tcaagctcct cagagtgcag cacagttgat   3360
aaccccttgc ctggagaagg agaagaagca gaggctgaac ctatgaattc cgatgagcca   3420
```

```
gaggcctgtt tcacagatgg ttgtgtacgg aggttctcat gctgccaagt taacatagag   3480
tcagggaaag gaaaaatctg gtggaacatc aggaaaacct gctacaagat tgttgaacac   3540
agttggtttg aaagcttcat tgtcctcatg atcctgctca gcagtggtgc cctggctttt   3600
gaagatattt atattgaaag gaaaaagacc attaagatta tcctggagta tgcagacaag   3660
atcttcactt acatcttcat tctgaaatgc ttctaaaat ggatagcata tggttataaa    3720
acatatttca ccaatgcctg tgttggctg gatttcctaa ttgttgatgt ttctttggtt    3780
actttagtgg caaacactct tggctactca gatcttggcc ccattaaatc ccttcggaca   3840
ctgagagctt taagacctct aagagcctta tctagatttg aaggaatgag ggtcgttgtg   3900
aatgcactca taggagcaat tccttccatc atgaatgtgc tacttgtgtg tcttatattc   3960
tggctgatat tcagcatcat gggagtaaat ttgtttgctg gcaagttcta tgagtgtatt   4020
aacaccacag atgggtcacg gtttcctgca agtcaagttc caaatcgttc cgaatgtttt   4080
gcccttatga atgttagtca aaatgtgcga tggaaaaacc tgaaagtgaa ctttgataat   4140
gtcggacttg gttacctatc tctgcttcaa gttgcaactt ttaagggatg gacgattatt   4200
atgtatgcag cagtggattc tgttaatgta gacaagcagc ccaaatatga atatagcctc   4260
tacatgtata tttatttgt cgtctttatc atctttgggt cattcttcac tttgaacttg   4320
ttcattggtg tcatcataga taatttcaac caacagaaaa agaagcttgg aggtcaagac   4380
atctttatga cagaagaaca gaagaaatac tataatgcaa tgaaaaagct ggggtccaag   4440
aagccacaaa agccaattcc tcgaccaggg aacaaaatcc aaggatgtat atttgaccta   4500
gtgacaaatc aagcctttga tattagtatc atggttctta tctgtctcaa catggtaacc   4560
atgatggtag aaaaggaggg tcaaagtcaa catatgactg aagttttata ttggataaat   4620
gtggttttta taatccttttt cactggagaa tgtgtgctaa aactgatctc cctcagacac   4680
tactacttca ctgtaggatg gaatattttt gattttgtgg ttgtgattat ctccattgta   4740
ggtatgtttc tagctgattt gattgaaacg tattttgtgt cccctaccct gttccgagtg   4800
atccgtcttg ccaggattgg ccgaatccta cgtctagtca aaggagcaaa ggggatccgc   4860
acgctgctct ttgctttgat gatgtccctt cctgcgttgt ttaacatcgg cctcctgctc   4920
ttcctggtca tgttcatcta cgccatcttt ggaatgtcca actttgccta tgttaaaaag   4980
gaagatggaa ttaatgacat gttcaatttt gagacctttg caacagtat gatttgcctg    5040 ttccaaatta caacctctgc tggctgggat ggattgctag cacctattct taacagtaag   5100
ccacccgact gtgacccaaa aaagttcat cctggaagtt cagttgaagg agactgtggt   5160
aacccatctg ttggaatatt ctactttgtt agttatatca tcatatcctt cctggttgtg   5220
gtgaacatgt acattgcagt catactggag aattttagtg ttgccactga agaaagtact   5280
gaacctctga gtgaggatga ctttgagatg ttctatgagg tttgggagaa gtttgatccc   5340
gatgcgaccc agtttataga gttctctaaa ctctctgatt ttgcagctgc cctggatcct   5400
cctcttctca tagcaaaacc caacaaagtc cagctcattg ccatggatct gcccatggtt   5460
agtggtgacc ggatccattg tcttgacatc ttatttgctt ttacaaagcg tgttttgggt   5520
gagagtgggg agatggattc tcttcgttca cagatggaag aaaggttcat gtctgcaaat   5580
ccttccaaag tgtcctatga acccatcaca accacactaa aacggaaaca agaggatgtg   5640
tctgctactg tcattcagcg tgcttataga cgttaccgct taaggcaaaa tgtcaaaaat   5700
atatcaagta tatacataaa agatggagac agagatgatg atttactcaa taaaaaagat   5760
atggcttttg ataatgttaa tgagaactca agtccagaaa aaacagatgc cacttcatcc   5820
```

```
accacctctc caccttcata tgatagtgta acaaagccag acaaagagaa atatgaacaa    5880
gacagaacag aaaaggaaga caaagggaaa gacagcaagg aaagcaaaaa atag          5934
```

<210> SEQ ID NO 13
<211> LENGTH: 5934
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 13

```
atggcaatgt tgcctccccc aggacctcag agctttgtcc atttcacaaa acagtctctt      60
gccctcattg aacaacgcat tgctgaaaga aaatcaaagg aacccaaaga agaaaagaaa     120
gatgatgatg aagaagcccc aaagccaagc agtgacttgg aagctggcaa acaactgccc     180
ttcatctatg gggacattcc tcccggcatg tgtcagagc ccctggagga cttggacccc      240
tactatgcag acaaaaagac tttcatagta ttgaacaaag ggaaaacaat cttccgtttc     300
aatgccacac ctgctttata tgctttct cctttcagtc ctctaagaag aatatctatt       360
aagattttag tacactcctt attcagcatg ctcatcatgt gcactattct gacaaactgc     420
atatttatga ccatgaataa cccgccggac tggaccaaaa atgtcgagta cacttttact     480
ggaatatata cttttgaatc acttgtaaaa atccttgcaa gaggcttctg tgtaggagaa     540 ttcactttc ttcgtgaccc gtggaactgg ctggattttg tcgtcattgt ttttgcgtat      600
ttaacagaat ttgtaaacct aggcaatgtt tcagctcttc gaactttcag agtattgaga     660
gctttgaaaa ctatttctgt aatcccaggc ctgaagacaa ttgtagggc tttgatccag      720 tcagtgaaga agctttctga tgtcatgatc ctgactgtgt tctgtctgag tgtgtttgca     780
ctaattggac tacagctgtt catgggaaac ctgaagcata atgtttcg aaattcactt       840 gaaaataatg aaacattaga aagcataatg aatacctag agagtgaaga agactttaga     900
aaatattttt attacttgga aggatccaaa gatgctctcc tttgtggttt cagcacagat     960
tcaggtcagt gtccagaggg gtacacctgt gtgaaaattg gcagaaaccc tgattatggc    1020
tacacgagct ttgacacttt cagctgggcc ttcttagcct tgtttaggct aatgacccaa    1080
gattactggg aaaacctttta ccaacagacg ctgcgtgctg ctggcaaaac ctacatgatc    1140
ttctttgtcg tagtgatttt cctgggctcc ttttatctaa taaacttgat cctggctgtg    1200
gttgccatgg catatgaaga acagaaccag gcaaacattg aagaagctaa acagaaagaa    1260
ttagaatttc aacagatgtt agaccgtctt aaaaaagagc aagaagaagc tgaggcaatt    1320
gcagcggcag cggctgaata tacaagtatt aggagaagca gaattatggg cctctcagag    1380
agttcttctg aaacatccaa actgagctct aaaagtgcta agaaagaag aaacagaaga    1440 aagaaaaaga atcaaaagaa gctctccagt ggagaggaaa agggagatgc tgagaaattg    1500
tcgaaatcag aatcagagga cagcatcaga agaaaaagtt ccaccttgg tgtcgaaggg    1560 cataggcgag cacatgaaaa gaggttgtct acccccaatc agtcaccact cagcattcgt    1620
ggctccttgt tttctgcaag gcgaagcagc agaacaagtc tttttagttt caaaggcaga    1680
ggaagagata taggatctga gactgaattt gccgatgatg agcacagcat ttttggagac    1740
aatgagagca aaggggctc actgtttgtg ccccacagac cccaggagcg acgcagcagt    1800
aacatcagcc aagccagtag gtccccacca atgctgccgg tgaacgggaa aatgcacagt    1860
gctgtggact gcaacggtgt ggtctccctg gttgatggac gctcagccct catgctcccc    1920
```

```
aatggacagc ttctgccaga gggcacgacc aatcaaatac acaagaaaag gcgttgtagt   1980
tcctatctcc tttcagagga tatgctgaat gatcccaacc tcagacagag agcaatgagt   2040
agagcaagca tattaacaaa cactgtggaa gaacttgaag agtccagaca aaaatgtcca   2100
ccttggtggt acagatttgc acacaaattc ttgatctgga attgctctcc atattggata   2160
aaattcaaaa agtgtatcta ttttattgta atggatcctt tgtagatct tgcaattacc    2220
atttgcatag ttttaaacac attatttatg gctatggaac accacccaat gactgaggaa   2280
ttcaaaaatg tacttgctat aggaaatttg gtctttactg gaatctttgc agctgaaatg   2340
gtattaaaac tgattgccat ggatccatat gagtatttcc aagtaggctg gaatattttt   2400
gacagcctta ttgtgacttt aagtttagtg gagctctttc tagcagatgt ggaaggattg   2460
tcagttctgc gatcattcag actgctccga gtcttcaagt tggcaaaatc ctggccaaca   2520
ttgaacatgc tgattaagat cattggtaac tcagtagggg ctctaggtaa cctcaccttta  2580
gtgttggcca tcatcgtctt cattttttgct gtggtcggca tgcagctctt tggtaagagc  2640
tacaaagaat gtgtctgcaa gatcaatgat gactgtacgc tcccacggtg gcacatgaac   2700
gacttcttcc actccttcct gattgtgttc cgcgtgctgt gtggagagtg gatagagacc   2760
atgtgggact gtatggaggt cgctggtcaa gctatgtgcc ttattgttta catgatggtc   2820
atggtcattg gaaacctggt ggtcctaaac ctatttctgg ccttattatt gagctcattt   2880
agttcagaca atcttacagc aattgaagaa gaccctgatg caaacaacct ccagattgca   2940
gtgactagaa ttaaaagggg aataaattat gtgaaacaaa ccttacgtga atttattcta   3000
aaagcatttt ccaaaaagcc aaagatttcc agggagataa gacaagcaga agatctgaat   3060
actaagaagg aaaactatat ttctaaccat acacttgctg aaatgagcaa aggtcacaat   3120
ttcctcaagg aaaagataa aatcagtggt tttggaagca gcgtggacaa acacttgatg    3180
gaagacagtg atggtcaatc atttattcac aatcccagcc tcacagtgac agtgccaatt   3240
gcacctgggg aatccgattt ggaaaatatg aatgctgagg aacttagcag tgattcggat   3300
agtgaataca gcaaagtgag attaaaccgg tcaagctcct cagagtgcag cacagttgat   3360
aaccctttc ctggagaagg agaagaagca gaggctgaac ctatgaattc cgatgagcca    3420
gaggcctgtt tcacagatgg ttgtgtacgg aggttctcat gctgccaagt taacatagag   3480
tcagggaaag gaaaaatctg gtggaacatc aggaaaacct gctacaagat tgttgaacac   3540
agttggtttg aaagcttcat tgtcctcatg atcctgctca gcagtggtgc cctggctttt   3600
gaagatattt atattgaaag gaaaaagacc attaagatta tcctggagta tgcagacaag   3660
atcttcactt acatcttcat tctgaaatg cttctaaaat ggatagcata tggttataaa   3720
acatatttca ccaatgcctg tgtgttggctg gatttcctaa ttgttgatgt ttctttggtt  3780
actttagtgg caaacactct tggctactca gatcttggcc ccattaaatc ccttcggaca   3840
ctgagagctt taagacctct aagagcctta tctagatttg aaggaatgag ggtcgttgtg   3900
aatgcactca taggagcaat tccttccatc atgaatgtgc tacttgtgtg tcttatattc   3960
tggctgatat tcagcatcat gggagtaaat ttgtttgctg gcaagttcta tgagtgtatt   4020
aacaccacag atgggtcacg gtttcctgca agtcaagttc caaatcgttc gaatgttttt   4080
gcccttatga atgttagtca aaatgtgcga tggaaaaacc tgaaagtgaa ctttgataat   4140
gtcggacttg gttacctatc tctgcttcaa gttgcaactt ttaagggatg gacgattatt   4200
atgtatgcag cagtggattc tgttaatgta gacaagcagc ccaaatatga atatagcctc   4260
```

```
tacatgtata tttattttgt cgtctttatc atctttgggt cattcttcac tttgaacttg   4320
ttcattggtg tcatcataga taatttcaac caacagaaaa agaagcttgg aggtcaagac   4380
atctttatga cagaagaaca gaagaaatac tataatgcaa tgaaaaagct ggggtccaag   4440
aagccacaaa agccaattcc tcgaccaggg aacaaaatcc aaggatgtat atttgaccta   4500
gtgacaaatc aagcctttga tattagtatc atggttctta tctgtctcaa catggtaacc   4560
atgatggtag aaaaggaggg tcaaagtcaa catatgacta agttttata ttggataaat    4620 gtggttttta taatccttt cactggagaa tgtgtgctaa aactgatctc cctcagacac    4680
tactacttca ctgtaggatg aatattttt gattttgtgg ttgtgattat ctccattgta    4740
ggtatgtttc tagctgattt gattgaaacg tattttgtgt ccctaccct gttccgagtg    4800 atccgtcttg ccaggattgg ccgaatccta cgtctagtca aggagcaaa ggggatccgc    4860 acgctgctct ttgctttgat gatgtcccTT cctgcgttgt ttaacatcgg cctcctgctc    4920
ttcctggtca tgttcatcta cgccatcttt ggaatgtcca actttgccta tgttaaaaag   4980
gaagatggaa ttaatgacat gttcaatttt gagacctttg caacagtat gatttgcctg    5040 ttccaaatta caacctctgc tggctgggat ggattgctag cacctattct taacagtaag   5100
ccacccgact gtgacccaaa aaaagttcat cctggaagtt cagttgaagg agactgtggt   5160
aacccatctg ttggaatatt ctactttgtt agttatatca tcatatcctt cctggttgtg   5220
gtgaacatgt acattgcagt catactggag aattttagtg ttgccactga agaaagtact   5280
gaacctctga gtgaggatga ctttgagatg ttctatgagg tttgggagaa gtttgatccc   5340
gatgcgaccc agtttataga gttctctaaa ctctctgatt ttgcagctgc cctggatcct   5400
cctcttctca tagcaaaacc caacaaagtc cagctcattg ccatggatct gcccatggtt   5460
agtggtgacc ggatccattg tcttgacatc ttatttgctt ttacaaagcg tgttttgggt   5520
gagagtgggg agatggattc tcttcgttca cagatggaag aaaggttcat gtctgcaaat   5580
ccttccaaag tgtcctatga acccatcaca accacactaa aacggaaaca agaggatgtg   5640
tctgctactg tcattcagcg tgcttataga cgttaccgct taaggcaaaa tgtcaaaaat   5700
atatcaagta tatacataaa agatggagac agagatgatg atttactcaa taaaaaagat   5760
atggcttttg ataatgttaa tgagaactca agtccagaaa aacagatgc cacttcatcc    5820 accacctctc caccttcata tgatagtgta acaaagccag acaaagagaa atatgaacaa   5880
gacagaacag aaaaggaaga caagggaaa gacagcaagg aaagcaaaaa atag          5934

<210> SEQ ID NO 14
<211> LENGTH: 15
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 14
gcccttcatc tatgg                                                      15

<210> SEQ ID NO 15
<211> LENGTH: 15
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 15
```
aacccgccgg actgg                                            15

<210> SEQ ID NO 16
<211> LENGTH: 15
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 16
gctccccaat ggaca                                            15

<210> SEQ ID NO 17
<211> LENGTH: 15
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 17
atacacaaga aaagg                                            15

<210> SEQ ID NO 18
<211> LENGTH: 15
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 18
tcttgcaatt accat                                            15

<210> SEQ ID NO 19
<211> LENGTH: 15
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 19
accctttgcc tggag                                            15

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 20
gtcccgccca ttgcctgaca c                                     21

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 21

```
ttctggtcat gatatggtta ttcac                                           25
```

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 22

```
tgatagatgc gttgatgaca ttgg                                            24
```

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 23

```
ttcataaatg cagtaacttc ctgg                                            24
```

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 24

```
tgtttctttt aagtcagtac agag                                            24
```

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 25

```
agagccattc acaagaccag ag                                              22
```

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 26

```
actcagaaag gcagagaggt g                                               21
```

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 27

```
ttgccatgtt atcaatgtct gtg                                             23
```

```
<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 28
gactgatttg tatctggtta ggag                                          24

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 29
gcaatgtaat taggaaggtg tgag                                          24

<210> SEQ ID NO 30
<211> LENGTH: 26
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 30
tttgaatgaa ctctaaatga actacc                                        26

<210> SEQ ID NO 31
<211> LENGTH: 25
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 31
taagtattag gcgttaagac aaacc                                         25

<210> SEQ ID NO 32
<211> LENGTH: 5
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 32

Pro Phe Val Tyr Gly
 1               5

<210> SEQ ID NO 33
<211> LENGTH: 5
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 33

Asn Pro Gln Asp Trp
```

```
<210> SEQ ID NO 34
<211> LENGTH: 5
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 34

Leu Pro Tyr Gly Gln
 1               5

<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 35

Ile His Arg Lys Arg
 1               5

<210> SEQ ID NO 36
<211> LENGTH: 5
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 36

Leu Ala Val Thr Ile
 1               5

<210> SEQ ID NO 37
<211> LENGTH: 5
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 37

Asn Pro Phe Pro Gly
 1               5

<210> SEQ ID NO 38
<211> LENGTH: 1977
<212> TYPE: PRT
<213> ORGANISM: Homo Sapien

<400> SEQUENCE: 38

Met Ala Met Leu Pro Pro Pro Gly Pro Gln Ser Phe Val His Phe Thr
 1               5                  10                  15

Lys Gln Ser Leu Ala Leu Ile Glu Gln Arg Ile Ala Glu Arg Lys Ser
            20                  25                  30

Lys Glu Pro Lys Glu Glu Lys Lys Asp Asp Asp Glu Glu Ala Pro Lys
        35                  40                  45

Pro Ser Ser Asp Leu Glu Ala Gly Lys Gln Leu Pro Phe Ile Tyr Gly
    50                  55                  60

Asp Ile Pro Pro Gly Met Val Ser Glu Pro Leu Glu Asp Leu Asp Pro
```

-continued

```
                65                  70                  75                  80
Tyr Tyr Ala Asp Lys Lys Thr Phe Ile Val Leu Asn Lys Gly Lys Thr
                    85                  90                  95
Ile Phe Arg Phe Asn Ala Thr Pro Ala Leu Tyr Met Leu Ser Pro Phe
                100                 105                 110
Ser Pro Leu Arg Arg Ile Ser Ile Lys Ile Leu Val His Ser Leu Phe
                115                 120                 125
Ser Met Leu Ile Met Cys Thr Ile Leu Thr Asn Cys Ile Phe Met Thr
                130                 135                 140
Met Asn Asn Pro Pro Asp Trp Thr Lys Asn Val Glu Tyr Thr Phe Thr
145                 150                 155                 160
Gly Ile Tyr Thr Phe Glu Ser Leu Val Lys Ile Leu Ala Arg Gly Phe
                    165                 170                 175
Cys Val Gly Glu Phe Thr Phe Leu Arg Asp Pro Trp Asn Trp Leu Asp
                    180                 185                 190
Phe Val Val Ile Val Phe Ala Tyr Leu Thr Glu Phe Val Asn Leu Gly
                    195                 200                 205
Asn Val Ser Ala Leu Arg Thr Phe Arg Val Leu Arg Ala Leu Lys Thr
                    210                 215                 220
Ile Ser Val Ile Pro Gly Leu Lys Thr Ile Val Gly Ala Leu Ile Gln
225                 230                 235                 240
Ser Val Lys Lys Leu Ser Asp Val Met Ile Leu Thr Val Phe Cys Leu
                    245                 250                 255
Ser Val Phe Ala Leu Ile Gly Leu Gln Leu Phe Met Gly Asn Leu Lys
                    260                 265                 270
His Lys Cys Phe Arg Asn Ser Leu Glu Asn Asn Glu Thr Leu Glu Ser
                    275                 280                 285
Ile Met Asn Thr Leu Glu Ser Glu Glu Asp Phe Arg Lys Tyr Phe Tyr
                290                 295                 300
Tyr Leu Glu Gly Ser Lys Asp Ala Leu Leu Cys Gly Phe Ser Thr Asp
305                 310                 315                 320
Ser Gly Gln Cys Pro Glu Gly Tyr Thr Cys Val Lys Ile Gly Arg Asn
                    325                 330                 335
Pro Asp Tyr Gly Tyr Thr Ser Phe Asp Thr Phe Ser Trp Ala Phe Leu
                    340                 345                 350
Ala Leu Phe Arg Leu Met Thr Gln Asp Tyr Trp Glu Asn Leu Tyr Gln
                    355                 360                 365
Gln Thr Leu Arg Ala Ala Gly Lys Thr Tyr Met Ile Phe Phe Val Val
                370                 375                 380
Val Ile Phe Leu Gly Ser Phe Tyr Leu Ile Asn Leu Ile Leu Ala Val
385                 390                 395                 400
Val Ala Met Ala Tyr Glu Glu Gln Asn Gln Ala Asn Ile Glu Glu Ala
                    405                 410                 415
Lys Gln Lys Glu Leu Glu Phe Gln Gln Met Leu Asp Arg Leu Lys Lys
                    420                 425                 430
Glu Gln Glu Glu Ala Glu Ala Ile Ala Ala Ala Ala Ala Glu Tyr Thr
                    435                 440                 445
Ser Ile Arg Arg Ser Arg Ile Met Gly Leu Ser Glu Ser Ser Ser Glu
                    450                 455                 460
Thr Ser Lys Leu Ser Ser Lys Ser Ala Lys Glu Arg Arg Asn Arg Arg
465                 470                 475                 480
Lys Lys Lys Asn Gln Lys Lys Leu Ser Ser Gly Glu Glu Lys Gly Asp
                    485                 490                 495
```

```
Ala Glu Lys Leu Ser Lys Ser Glu Ser Glu Asp Ser Ile Arg Arg Lys
            500                 505                 510

Ser Phe His Leu Gly Val Glu Gly His Arg Arg Ala His Glu Lys Arg
            515                 520                 525

Leu Ser Thr Pro Asn Gln Ser Pro Leu Ser Ile Arg Gly Ser Leu Phe
            530                 535                 540

Ser Ala Arg Arg Ser Ser Arg Thr Ser Leu Phe Ser Phe Lys Gly Arg
545                 550                 555                 560

Gly Arg Asp Ile Gly Ser Glu Thr Glu Phe Ala Asp Asp Glu His Ser
                565                 570                 575

Ile Phe Gly Asp Asn Glu Ser Arg Arg Gly Ser Leu Phe Val Pro His
            580                 585                 590

Arg Pro Gln Glu Arg Arg Ser Ser Asn Ile Ser Gln Ala Ser Arg Ser
            595                 600                 605

Pro Pro Met Leu Pro Val Asn Gly Lys Met His Ser Ala Val Asp Cys
            610                 615                 620

Asn Gly Val Val Ser Leu Val Asp Gly Arg Ser Ala Leu Met Leu Pro
625                 630                 635                 640

Asn Gly Gln Leu Leu Pro Glu Gly Thr Thr Asn Gln Ile His Lys Lys
            645                 650                 655

Arg Arg Cys Ser Ser Tyr Leu Leu Ser Glu Asp Met Leu Asn Asp Pro
            660                 665                 670

Asn Leu Arg Gln Arg Ala Met Ser Arg Ala Ser Ile Leu Thr Asn Thr
            675                 680                 685

Val Glu Glu Leu Glu Glu Ser Arg Gln Lys Cys Pro Pro Trp Trp Tyr
            690                 695                 700

Arg Phe Ala His Lys Phe Leu Ile Trp Asn Cys Ser Pro Tyr Trp Ile
705                 710                 715                 720

Lys Phe Lys Lys Cys Ile Tyr Phe Ile Val Met Asp Pro Phe Val Asp
                725                 730                 735

Leu Ala Ile Thr Ile Cys Ile Val Leu Asn Thr Leu Phe Met Ala Met
            740                 745                 750

Glu His His Pro Met Thr Glu Glu Phe Lys Asn Val Leu Ala Ile Gly
            755                 760                 765

Asn Leu Val Phe Thr Gly Ile Phe Ala Ala Glu Met Val Leu Lys Leu
            770                 775                 780

Ile Ala Met Asp Pro Tyr Glu Tyr Phe Gln Val Gly Trp Asn Ile Phe
785                 790                 795                 800

Asp Ser Leu Ile Val Thr Leu Ser Leu Val Glu Leu Phe Leu Ala Asp
                805                 810                 815

Val Glu Gly Leu Ser Val Leu Arg Ser Phe Arg Leu Leu Arg Val Phe
            820                 825                 830

Lys Leu Ala Lys Ser Trp Pro Thr Leu Asn Met Leu Ile Lys Ile Ile
            835                 840                 845

Gly Asn Ser Val Gly Ala Leu Gly Asn Leu Thr Leu Val Leu Ala Ile
            850                 855                 860

Ile Val Phe Ile Phe Ala Val Val Gly Met Gln Leu Phe Gly Lys Ser
865                 870                 875                 880

Tyr Lys Glu Cys Val Cys Lys Ile Asn Asp Asp Cys Thr Leu Pro Arg
                885                 890                 895

Trp His Met Asn Asp Phe Phe His Ser Phe Leu Ile Val Phe Arg Val
            900                 905                 910
```

```
Leu Cys Gly Glu Trp Ile Glu Thr Met Trp Asp Cys Met Glu Val Ala
    915                 920                 925
Gly Gln Ala Met Cys Leu Ile Val Tyr Met Met Val Met Val Ile Gly
    930                 935                 940
Asn Leu Val Val Leu Asn Leu Phe Leu Ala Leu Leu Leu Ser Ser Phe
945                 950                 955                 960
Ser Ser Asp Asn Leu Thr Ala Ile Glu Glu Asp Pro Asp Ala Asn Asn
                965                 970                 975
Leu Gln Ile Ala Val Thr Arg Ile Lys Lys Gly Ile Asn Tyr Val Lys
                980                 985                 990
Gln Thr Leu Arg Glu Phe Ile Leu Lys Ala Phe Ser Lys Lys Pro Lys
                995                 1000                1005
Ile Ser Arg Glu Ile Arg Gln Ala Glu Asp Leu Asn Thr Lys Lys Glu
    1010                1015                1020
Asn Tyr Ile Ser Asn His Thr Leu Ala Glu Met Ser Lys Gly His Asn
1025                1030                1035                1040
Phe Leu Lys Glu Lys Asp Lys Ile Ser Gly Phe Gly Ser Ser Val Asp
                1045                1050                1055
Lys His Leu Met Glu Asp Ser Asp Gly Gln Ser Phe Ile His Asn Pro
                1060                1065                1070
Ser Leu Thr Val Thr Val Pro Ile Ala Pro Gly Glu Ser Asp Leu Glu
                1075                1080                1085
Asn Met Asn Ala Glu Glu Leu Ser Ser Asp Ser Asp Ser Glu Tyr Ser
                1090                1095                1100
Lys Val Arg Leu Asn Arg Ser Ser Ser Ser Glu Cys Ser Thr Val Asp
1105                1110                1115                1120
Asn Pro Leu Pro Gly Glu Gly Glu Glu Ala Glu Ala Glu Pro Met Asn
                1125                1130                1135
Ser Asp Glu Pro Glu Ala Cys Phe Thr Asp Gly Cys Val Arg Arg Phe
                1140                1145                1150
Ser Cys Cys Gln Val Asn Ile Glu Ser Gly Lys Gly Lys Ile Trp Trp
                1155                1160                1165
Asn Ile Arg Lys Thr Cys Tyr Lys Ile Val Glu His Ser Trp Phe Glu
    1170                1175                1180
Ser Phe Ile Val Leu Met Ile Leu Leu Ser Ser Gly Ala Leu Ala Phe
1185                1190                1195                1200
Glu Asp Ile Tyr Ile Glu Arg Lys Lys Thr Ile Lys Ile Ile Leu Glu
                1205                1210                1215
Tyr Ala Asp Lys Ile Phe Thr Tyr Ile Phe Ile Leu Glu Met Leu Leu
                1220                1225                1230
Lys Trp Ile Ala Tyr Gly Tyr Lys Thr Tyr Phe Thr Asn Ala Trp Cys
                1235                1240                1245
Trp Leu Asp Phe Leu Ile Val Asp Val Ser Leu Val Thr Leu Val Ala
                1250                1255                1260
Asn Thr Leu Gly Tyr Ser Asp Leu Gly Pro Ile Lys Ser Leu Arg Thr
1265                1270                1275                1280
Leu Arg Ala Leu Arg Pro Leu Arg Ala Leu Ser Arg Phe Glu Gly Met
                1285                1290                1295
Arg Val Val Val Asn Ala Leu Ile Gly Ala Ile Pro Ser Ile Met Asn
                1300                1305                1310
Val Leu Leu Val Cys Leu Ile Phe Trp Leu Ile Phe Ser Ile Met Gly
                1315                1320                1325
Val Asn Leu Phe Ala Gly Lys Phe Tyr Glu Cys Ile Asn Thr Thr Asp
```

```
            1330                1335                1340
Gly Ser Arg Phe Pro Ala Ser Gln Val Pro Asn Arg Ser Glu Cys Phe
1345                1350                1355                1360

Ala Leu Met Asn Val Ser Gln Asn Val Arg Trp Lys Asn Leu Lys Val
                1365                1370                1375

Asn Phe Asp Asn Val Gly Leu Gly Tyr Leu Ser Leu Leu Gln Val Ala
                1380                1385                1390

Thr Phe Lys Gly Trp Thr Ile Ile Met Tyr Ala Ala Val Asp Ser Val
                1395                1400                1405

Asn Val Asp Lys Gln Pro Lys Tyr Glu Tyr Ser Leu Tyr Met Tyr Ile
                1410                1415                1420

Tyr Phe Val Val Phe Ile Ile Phe Gly Ser Phe Phe Thr Leu Asn Leu
1425                1430                1435                1440

Phe Ile Gly Val Ile Ile Asp Asn Phe Asn Gln Gln Lys Lys Lys Leu
                1445                1450                1455

Gly Gly Gln Asp Ile Phe Met Thr Glu Glu Gln Lys Lys Tyr Tyr Asn
                1460                1465                1470

Ala Met Lys Lys Leu Gly Ser Lys Lys Pro Gln Lys Pro Ile Pro Arg
                1475                1480                1485

Pro Gly Asn Lys Ile Gln Gly Cys Ile Phe Asp Leu Val Thr Asn Gln
                1490                1495                1500

Ala Phe Asp Ile Ser Ile Met Val Leu Ile Cys Leu Asn Met Val Thr
1505                1510                1515                1520

Met Met Val Glu Lys Glu Gly Gln Ser Gln His Met Thr Glu Val Leu
                1525                1530                1535

Tyr Trp Ile Asn Val Val Phe Ile Ile Leu Phe Thr Gly Glu Cys Val
                1540                1545                1550

Leu Lys Leu Ile Ser Leu Arg His Tyr Tyr Phe Thr Val Gly Trp Asn
                1555                1560                1565

Ile Phe Asp Phe Val Val Val Ile Ser Ile Val Gly Met Phe Leu
                1570                1575                1580

Ala Asp Leu Ile Glu Thr Tyr Phe Val Ser Pro Thr Leu Phe Arg Val
1585                1590                1595                1600

Ile Arg Leu Ala Arg Ile Gly Arg Ile Leu Arg Leu Val Lys Gly Ala
                1605                1610                1615

Lys Gly Ile Arg Thr Leu Leu Phe Ala Leu Met Met Ser Leu Pro Ala
                1620                1625                1630

Leu Phe Asn Ile Gly Leu Leu Leu Phe Leu Val Met Phe Ile Tyr Ala
                1635                1640                1645

Ile Phe Gly Met Ser Asn Phe Ala Tyr Val Lys Lys Glu Asp Gly Ile
                1650                1655                1660

Asn Asp Met Phe Asn Phe Glu Thr Phe Gly Asn Ser Met Ile Cys Leu
1665                1670                1675                1680

Phe Gln Ile Thr Thr Ser Ala Gly Trp Asp Gly Leu Leu Ala Pro Ile
                1685                1690                1695

Leu Asn Ser Lys Pro Pro Asp Cys Asp Pro Lys Lys Val His Pro Gly
                1700                1705                1710

Ser Ser Val Glu Gly Asp Cys Gly Asn Pro Ser Val Gly Ile Phe Tyr
                1715                1720                1725

Phe Val Ser Tyr Ile Ile Ile Ser Phe Leu Val Val Val Asn Met Tyr
                1730                1735                1740

Ile Ala Val Ile Leu Glu Asn Phe Ser Val Ala Thr Glu Glu Ser Thr
1745                1750                1755                1760
```

```
Glu Pro Leu Ser Glu Asp Asp Phe Glu Met Phe Tyr Glu Val Trp Glu
            1765            1770            1775

Lys Phe Asp Pro Asp Ala Thr Gln Phe Ile Glu Phe Ser Lys Leu Ser
            1780            1785            1790

Asp Phe Ala Ala Ala Leu Asp Pro Pro Leu Leu Ile Ala Lys Pro Asn
            1795            1800            1805

Lys Val Gln Leu Ile Ala Met Asp Leu Pro Met Val Ser Gly Asp Arg
            1810            1815            1820

Ile His Cys Leu Asp Ile Leu Phe Ala Phe Thr Lys Arg Val Leu Gly
1825            1830            1835            1840

Glu Ser Gly Glu Met Asp Ser Leu Arg Ser Gln Met Glu Glu Arg Phe
            1845            1850            1855

Met Ser Ala Asn Pro Ser Lys Val Ser Tyr Glu Pro Ile Thr Thr Thr
            1860            1865            1870

Leu Lys Arg Lys Gln Glu Asp Val Ser Ala Thr Val Ile Gln Arg Ala
            1875            1880            1885

Tyr Arg Arg Tyr Arg Leu Arg Gln Asn Val Lys Asn Ile Ser Ser Ile
            1890            1895            1900

Tyr Ile Lys Asp Gly Asp Arg Asp Asp Leu Leu Asn Lys Lys Asp
1905            1910            1915            1920

Met Ala Phe Asp Asn Val Asn Glu Asn Ser Ser Pro Glu Lys Thr Asp
            1925            1930            1935

Ala Thr Ser Ser Thr Thr Ser Pro Pro Ser Tyr Asp Ser Val Thr Lys
            1940            1945            1950

Pro Asp Lys Glu Lys Tyr Glu Gln Asp Arg Thr Glu Lys Glu Asp Lys
            1955            1960            1965

Gly Lys Asp Ser Lys Glu Ser Lys Lys
            1970            1975
```